US005635356A

United States Patent [19]
Packard et al.

[11] Patent Number: 5,635,356
[45] Date of Patent: Jun. 3, 1997

[54] ANTI-ONCOIMMUNIN-M ANTIBODIES AND USES THEREOF

[75] Inventors: Beverly Packard; Akira Komoriya, both of Rockville, Md.

[73] Assignee: The United States of America as represented by the Department of Health and Human Services, Washington, D.C.

[21] Appl. No.: 218,023

[22] Filed: Mar. 22, 1994

Related U.S. Application Data

[63] Continuation-in-part of Ser. No. 764,695, Sep. 23, 1991, Pat. No. 5,364,619, which is a continuation-in-part of Ser. No. 707,136, May 31, 1991, abandoned.

[51] Int. Cl.$^6$ .......................... C07K 16/24; C07K 14/52; C12P 21/08; G01N 33/53
[52] U.S. Cl. .................. 435/7.1; 530/387.7; 530/388.23; 530/387.3; 530/350; 530/351
[58] Field of Search .................. 530/388.1, 388.2, 530/387.7, 388.23, 387.3, 350, 351; 435/7.1, 7.21, 975

[56] References Cited

U.S. PATENT DOCUMENTS

| | | | |
|---|---|---|---|
| 4,496,658 | 1/1985 | Kondo et al. | 436/510 |
| 4,863,727 | 9/1989 | Zimmerman | 424/85.2 |
| 5,154,921 | 10/1992 | Sager et al. | 424/93 |
| 5,364,619 | 11/1994 | Packard et al. | 424/85.1 |
| 5,370,991 | 12/1994 | Remold-O'Donnell | 435/6 |

OTHER PUBLICATIONS

Packard, B.S., et al., "Identification of a New Growth Factor for Lymphocytes: Mitogenic Stimulation of Lymphocytes by Tumor Cell Lines," Federation of American Society of Experimental Biology, (Apr. 1991) Atlanta, GA.

Packard, B.S., "Identification of a New Class of Growth Factors: Tumor-Derived Lymphocytes Mitogens," Biophysical Society of America, (Feb. 1991) San Francisco, CA.

Packard, B.S., "Mitogenic Stimulation of Human T Cells by Solid Tumor Lines Mediated by Secreted Proteins," Biophysical Society of America, (Feb. 1990) Baltimore, MD.

Packard, B.S., "Mitogenic Stimulation of Human Tumor Infiltrating Lymphocytes by Human Cell Lines," American Assoc. of Cancer Research, (May 1990) Washington, D.C.

Packard, B.S., et al., "Mitogenic Stimulation of Human Tumor Infiltrating Lymphocytes by Human Cell Lines," (Mar. 1990) Florence, Italy.

Packard, B.S., "A New Mitogen Derived From a Tumor Cell Line for Tumor Infiltrating Lymphocytes (TILS)," American Society of Cell Biology, (Nov. 1989) Houston, TX.

Packard, B.S., "A New Mitogen for Tumor Infiltrating Lymphocytes (TILS) Derived From a Tumor Cell Line," (Nov. 1989) Hilton Head, SC.

Packard, B.S., "Mitogenic Stimulation of Human T Cells by Solid Tumor Lines Mediated by Secreted Proteins," (Jul. 1989) Berlin, West Germany.

Treves, A. J. et al., "Immunotherapy of Lethal Metastases by Lymphocytes Sensitized Against Tumor Cells In Vitro", *J. Natl. Cancer Inst.* 54: 777–780 (1975).

Lee, S.K., et al., "Autologous Leukemia-Specific T-Cell-Mediated Lymphocytotoxicity in Patients with Acute Myelogenous Leukemia," *J. Exp. Med.* 147: 912–922 (1978).

Zarling, J.M., et al., "Continuous Culture of T Cells Cytotoxic for Autologous Human Leukemia Cells," *Nature (London)*, 280: 685–687 (1979).

Vose, B.M., et al., "Human Tumour Antigens Defined by Cytotoxicity and Proliferative Responses of Cultured Lymphoid Cells," *Nature (London)*, 296: 359–361 (1982).

Vose, B.M., et al., "Specific Cytotoxicity Against Autologous Tumour and Proliferative Responses of Human Lymphocytes Grown in Interleukin 2," *Inst. J. Cancer,* 29: 33–39 (1982).

Vanky, F., et al., "Lysis Tumor Biopsy Cells by Autologous T Lymphocytes Activated in Mixed Cultures and Propagated with T Cell Growth Factor," *J. Exp. Med.,* 155: 83–95 (1982).

Mitsuya, et al., "Generation of an HLA-Restricted Cytotoxic T Cell Line Reactive Against Cultured Tumor Cells From a Patient Infected with Human T Cell Leukemia/Lymphoma Virus," *J. Exp. Med.,* 158: 994–999 (1983).

De Vries, J.E., et al., "Cloned Human Cytotoxic T Lymphocyte (CTL) Lines Reactive With Autologous Melanoma Cells," *J. Immunol.,* 132: 510–519 (1984).

Slovin, S.F., et al., "Cellular Immune Response to Human Sarcomas: Cytotoxic T. Cell Clones Reactive with Autologous Sarcomas," *J. Immunol.,* 137: 3042–3048 (1986).

Itoh, K., et al., "Interleukin 2 Activation of Cytotoxic T-Lymphocytes Infiltrating into Human Metastatic Melanomas," *Cancer Res.* 46: 3011–3017 (1986).

Rosenberg, et al., "A New Approach to the Adoptive Immunotherapy of Cancer with Tumor-Infiltrating Lymphocytes," *Science* 233: 1318–1321 (1986).

Rabinowich, H., et al., "Functional Analysis of Mononuclear Cells Infiltrating into Tumors: Lysis of Autologous Human Tumor Cells by Cultured Infiltrating Lymphocytes," *Cancer Res.* 47: 173–177 (1987).

Miescher, T., et al., "Clonal and Frequency Analyses of Tumor-Infiltrating T Lymphocytes From Human Solid Tumors," *J. Immunol.* 138: 4004–4011 (1987).

Kradin, R.L., et al., "Tumor-Derived Interleukin-2-Dependent Lymphocytes in Adoptive Immunotherapy of Lung Cancer," *Cancer Immunol. Immunother.* 24: 76–85 (1987).

*Primary Examiner*—Lila Feisee
*Assistant Examiner*—John Lucas
*Attorney, Agent, or Firm*—Townsend and Townsend and Crew

[57] ABSTRACT

The present invention relates, in general, to oncoimmunins. In particular, the present invention relates to antibodies that specifically bind to a tumor-derived Oncoimmunin-myeloid (OI-M) factor that induces differentiation of myeloid cells. The invention also provides methods of detecting OI-M factors utilizing OI-M specific antibodies and immunodetection kits.

3 Claims, 25 Drawing Sheets

OTHER PUBLICATIONS

Rosenberg, S.A., et al., "Use of Tumor–Infiltrating Lymphocytes and Interleukin–2 in the Immunotherapy of Patients with Metastatic Melanoma," *New Engl. J. Med.* 319: 1676–1680 (1988).

Smith, K.A., "Interleukin–2: Inception, Impact, and Implications," *Science*, 240: 1169–1176 (1988).

Topalian, S.L., et al., "Expansion of Human Tumor Infiltrating Lymphocytes for Use in Immunotherapy Trials," *J. Immunol. Meth.* 102: 127–141 (1987).

Packard, B.S., "Identification of a Synthetic Nonapeptide Sequence that Inhibits Motility in Culture of a Melanoma Subclone that Possesses a High Metastatic Potential," *Proc. Natl. Acad. Sci. USA*, Cell Biology, 84: 9015–9019 (1987).

Kirnbauer, R., et al., "IFN–β2 Cell Differentiation Factor 2, or Hybridoma Growth Factor (IL–6) is Expressed and Released by Human Epidermal Cells and Epidermoid Carc" *J. Immunol.*, 142: 1922–1928 (1989).

Packard, B.S., "The Use of Tumor–Infiltrating Lymphocytes in Cancer Therapy", *Progress in Regional Cancer Therapy*, Jackez, R. et al., eds., Springer, Heidelberg, (1990) pp. 293–303.

Smith, K.A., "The Interleukin 2 Reporter," *Adv. Immunol.*, 42: 165–179 (1988).

Quinan, C.V., "Points to Consider in the Collection, Processing, and Testing of Ex Vivo Activated Mononuclear Leukocytes for Administration to Humans", *Publication of Center for Biologics Evaluation and Research*, Food and Drug Administration (1989).

Andreesen, R., et al., *Pathobiology*, 59: 259–263 (1991).

Bartholeyns, et al., *Anticancer Res.* 11: 1201–1204 (1991).

Andreesen, et al., *Cancer Detection and Prevention*, 15: 413–421 (1991).

Packard, B.Z. et al., *Journal of Biological Chemistry*, 268:9 6356–6363 (Mar. 25, 1993).

Remold–O'Donnell, E., et al., *Proc. Natl. Acad. Sci. USA*, Biochemistry, : 5635–5639 (Jun. 1992).

Zou, Z. et al., *Science*, 263: 526–529 (Jan. 28, 1994).

Packard, B.S., "Mitogenic Stimulation of Human Tumor–Infiltrating Lymphocytes by Secreted Factor(s) from Human Tumor Cell Lines," *Proc. Natl. Acad. Sci. USA*, (1990) vol. 87, pp. 4058–4062.

Packard, B.Z., et al., "Oncoimmunin–L, A 45–Kilodalton Protein with Lymphoid Immunomodulatory Activity: Mitogenic Stimulation of Human Tumor Infiltrating Lymphyocytes," *FASEB Journal* 8:(7) (Apr. 1994): p. A1460.

Packard, B.Z., "Induced Integrin Cell Surface Expression and Chemotactic Responsiveness by Oncoimmunin–M," *Biophysical Journal* 66(2, part 2):A172, 1994.

Packard, B.Z., et al., "Immunotherapy Without MHC Restriction," Growth Factors and Medical Oncology, Rimini, Italy (Jun. 1993).

Packard, B.Z., et al., "Oncoimmunin–M (OI–M) Induces Human Leukemic Cell (HL–60) Motility to Human C5a," Biophysical J. 64(2 part 2): A368, 1993.

Packard, B.S., et al., "Oncoimmunins: New Tumor–Derived Factors with Potential Immunomodulatory Activities," Am. Soc. Hematol. (Dec. 1992).

Packard, B.Z., "Oncoimmunins: New Tumor–Derived Cytokines with Immunomodulatory Activity," Am. Assoc. Immunol., Anaheim, CA (Apr. 1992).

Packard, B.Z., "Oncoimmunins: New Tumor–Derived Cytokines with Immunomodulatory Activity," Biophysical J. 61(2 part 2):A48, 1992.

Packard, B.Z., "Oncoimmunin: A New Tumor–Derived Cytokine with Immunostimulatory Activity," J. Cell. Biol. 115(3, part 2):423A, 1991.

Packard, B.S., et al., "Oncoimmunins: New Tumor–Derived Factors with Immunomodulatory Activity," FASEB J. 6(5):A1695, 1992.

Roitt (1991) "Essential Immunology", Blackwell Scientific Publication, Oxford, pp. 65–68 & 74.

Sass et al (1989) J. Biol. Chem. 264(7): 4076–4081.

Intelligenetics Fast DB 5.4 Sequence Comparison, PIR 43 Databank, #A 32957.

Pan et al (1989) Histochemical J. 21: 638–644.

Cuhhajlani et al (1984) Leukemia Res. 8(6): 985–995.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
    ( A ) LENGTH: 16 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:1:

Gly Val His Pro Leu Ser Cys His Gly Xaa Val Leu Gly Glu His Gly
1               5                   10                  15

( 2 ) INFORMATION FOR SEQ ID NO:2:

( i ) SEQUENCE CHARACTERISTICS:
    ( A ) LENGTH: 10 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:2:

Ser Ala Asp Thr Leu Trp Gly Ile Gln Lys
1               5                   10

( 2 ) INFORMATION FOR SEQ ID NO:3:

( i ) SEQUENCE CHARACTERISTICS:
    ( A ) LENGTH: 13 amino acids
    ( B ) TYPE: amino acid
    ( D ) TOPOLOGY: unknown ( i i ) MOLECULE TYPE: peptide ( x i ) SEQUENCE DESCRIPTION: SEQ ID NO:3:

Thr Phe His Phe Asn Thr Val Glu Glu Val His Ser Arg
1               5                   10

( 2 ) INFORMATION FOR SEQ ID NO:4:

( i ) SEQUENCE CHARACTERISTICS:
    ( A ) LENGTH: 14 amino acids
    ( B ) TYPE: amino acid
    ( D ) TOPOLOGY: unknown (ii) MOLECULE TYPE: peptide (xi) SEQUENCE DESCRIPTION: SEQ ID NO:4:

```
Thr Tyr Asn Phe Leu Pro Glu Phe Leu Val Ser Thr Gln Lys
1               5                   10
```

(2) INFORMATION FOR SEQ ID NO:5:

(i) SEQUENCE CHARACTERISTICS:
        (A) LENGTH: 18 amino acids
        (B) TYPE: amino acid
        (D) TOPOLOGY: unknown (ii) MOLECULE TYPE: peptide (xi) SEQUENCE DESCRIPTION: SEQ ID NO:5:

```
Thr Tyr Gly Ala Asp Leu Ala Ser Val Asp Phe Gln His Ala Glu Asp
1               5                   10                  15
Ala Arg
```

(2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: unknown (ii) MOLECULE TYPE: peptide (xi) SEQUENCE DESCRIPTION: SEQ ID NO:6:

```
Phe Ala Tyr Gly Tyr Ile Glu Asp Leu Lys
1               5                   10
```

(2) INFORMATION FOR SEQ ID NO:7:

(i) SEQUENCE CHARACTERISTICS:
        (A) LENGTH: 29 amino acids
        (B) TYPE: amino acid
        (D) TOPOLOGY: unknown (ii) MOLECULE TYPE: peptide (xi) SEQUENCE DESCRIPTION: SEQ ID NO:7:

```
Val Leu Glu Leu Pro Tyr Gln Gly Glu Leu Ser Met Val Ile Leu
1               5                   10                  15
Leu Pro Asp Asp Ile Glu Asp Glu Ser Thr Gly Leu Lys
                20                  25
```

(2) INFORMATION FOR SEQ ID NO:8:

(i) SEQUENCE CHARACTERISTICS:
        (A) LENGTH: 20 amino acids
        (B) TYPE: amino acid
        (D) TOPOLOGY: unknown (ii) MOLECULE TYPE: peptide (xi) SEQUENCE DESCRIPTION: SEQ ID NO:8:

```
Leu His Glu Trp Thr Lys Pro Glu Asn Leu Asp Phe Ile Glu Val Asn
1               5                   10                  15
Val Xaa Leu Pro
                20
```

(2) INFORMATION FOR SEQ ID NO:9:

(i) SEQUENCE CHARACTERISTICS:

(A) LENGTH: 11 amino acids
(B) TYPE: amino acid
(D) TOPOLOGY: unknown (i i) MOLECULE TYPE: peptide (x i) SEQUENCE DESCRIPTION: SEQ ID NO:9:

| Leu | Gly | Val | Gln | Asp | Leu | Phe | Asn | Ser | Ser | Lys |
|-----|-----|-----|-----|-----|-----|-----|-----|-----|-----|-----|
| 1   |     |     |     | 5   |     |     |     |     | 10  |     |

ANTI-ONCOIMMUNIN-M ANTIBODIES AND USES THEREOF

CROSS-REFERENCE TO RELATED APPLICATIONS

This application is a continuation-in-part application of U.S. application Ser. No. 07/764,695, filed Sep. 23, 1991, U.S. Pat. No. 5,364,619 which was a continuation-in-part application of then U.S. application Ser. No. 07/707,136, filed on May 31, 1991, now abandoned.

FIELD OF THE INVENTION

The present invention relates, in general, to Oncoimmunins. In particular, the present invention relates to Oncoimmunin-lymphoid factor and Oncoimmunin-myeloid factor, pharmaceutical compositions of said factors, and methods of use of said factors.

BACKGROUND INFORMATION

The idea that the tumor environment is intrinsically immunogenic and, therefore, contains cells capable of mounting an immune response and inducing tumor regression has served as the basis for many immunotherapeutic clinical trials. (Treves, A. J. et al., *J. Natl. Cancer Inst.* 54:777–780 (1975); Lee, et al., *J. Exp. Med.* 147:912–922 (1978); Zarling, et al., *Nature* (London), 280:685–687 (1979); Vose, et al., *Nature* (London), 296:359–361 (1982); Vose, et al., *Int. J. Cancer*, 29:33–39 (1982); Vanky, et al., *J. Exp. Med.*, 155:83–95 (1982); Mitsuya, et al., *J. Exp. Med.*, 158:994–999 (1983); De Vries, et al., *J. Immunol.*, 132:510–519 (1984); Slovin, S. F. et al., *J. Immunol.*, 137:3042–3048 (1986); Itoh, K. et al., *Cancer Res.* 46:3011–3017 (1986); Rosenberg, et al., *Science* 233:1318–1321 (1986); Rabinowich, et al., *Cancer Res.* 47: 173–177 (1987); Miescher, et al., *J. Immunol.* 138:4004–4011 (1987); Kradin, et al., *Cancer Immunol. Immunother.* 24:76–85 (1987)). In particular, this approach has led to the use of tumor-infiltrating lymphocytes (TILs) in clinical trials (Id.). In this procedure lymphocytes, isolated from tumors, are grown ex vivo in the presence of the lymphokine interleukin-2 (IL-2). The patients are then reinfused with their TILs after the latter have been expanded in culture for several weeks.

Although adoptive immunotherapy using TILs appears highly efficacious (in the largest study to date, regression of tumors was observed in 40% to 60% of metastatic melanoma patients (Rosenberg, et al., *New Engl. J. Med.* 319:1676–1680 (1988))), the particular characteristics of the tumor environment that produce TILs in vivo remain unclear. Two classes of stimuli, one derived from cell-cell contact between tumor cells and immunocytes and the other from soluble factors may influence activation, homing and proliferation of lymphoid and/or myeloid cells (two basic host defense systems) in vivo.

While interleukin-2 is a soluble factor that acts as a potent mitogen for T-cells (members of the first host defense system) and may induce proliferation of T-cells that specifically home to the tumor, its biosynthesis appears to be confined to immunocytes (Smith, K. A. *Science*, 240:1169–1176 (1988)) and its presence is not characteristic of the tumor environment. Interleukin-2 is generally nonselective in activating T-cells as all lymphocytes have IL-2 receptors. Thus, while IL-2 is a potent mitogen, it does not specifically select and induce proliferation of the TIL phenotype.

The second important host defense system against tumor growth is the myeloid mononuclear phagocyte system. Mononuclear phagocytes need to be differentiated into mature macrophages and activated to acquire cytotoxic activity before they may be successfully used in the treatment of tumors (Bartholeyns, et al., *Anticancer Res.* 11:1201–1204 (1991)). This differentiation and activation may occur through modulation by endogenous signals in the tumor environment inducing them to secrete growth factors.

It is thus desirable to specifically recruit lymphocytes to mount an immune response against a targeted tumor. This may be accomplished by providing factors that specifically act to select and proliferate tumor infiltrating lymphocytes or by providing factors that specifically act to induce differentiation and activation of mononuclear macrophages. It is most likely that such factors may be derived from the tumor environment. However no such factors have been previously identified.

SUMMARY OF THE INVENTION

The present invention provides for two novel soluble factors, Oncoimmunin-lymphoid factor (designated Oncoimmunin-L or OI-L) and Oncoimmunin-myeloid factor (designated Oncoimmunin-M or OI-M) derived from tumors. The factors act to induce T-cell proliferation and macrophage differentiation respectively.

Thus, in one embodiment, the present invention provides for a substantially pure Oncoimmunin-lymphoid factor derived from a tumor cell line having a molecular weight of about 45 kDa by SDS-PAGE analysis and having the ability to stimulate T-lymphocyte mitogenesis in an interleukin-2 and interleukin-4 free, serum-free medium. This Oncoimmunin-lymphoid factor may be recombinantly produced.

The invention provides for both a method of purifying the Oncoimmunin-lymphoid factor from an interleukin-2 and interleukin-4 free, serum-free, conditioned medium of a tumor cell line, and the substantially pure Oncoimmunin-lymphoid factor produced by the purification where the purification comprises the steps of:

a) subjecting the medium to an ion exchange chromatography, b) selecting from the chromatography, the late eluting fractions displaying bioactivity;

c) subjecting the late eluting fractions selected in step (b) to a gel filtration chromatography;

d) selecting the fractions from gel filtration showing bioactivity;

e) subjecting the fractions selected in step (d) to an anion exchange chromatography;

f) selecting the fractions from anion exchange chromatography showing bioactivity; and g) subjecting the fractions selected in step (f) to a reverse phase high performance liquid chromatography; resulting in the purification of said factor; wherein said bioactivity is measured as an increase in [$^3$H]-thymidine incorporation by a tumor infiltrating lymphocyte line.

The substantially pure Oncoimmunin-lymphoid factor of the present invention comprises an amino acid sequence having at least 80%, preferably at least 90%, and still more preferably at least 95% sequence identity with a sequence selected from the group consisting of Seq ID No: 3, Seq ID No: 4, Seq ID No: 5, Seq ID No: 6, Seq ID No: 7, Seq ID No: 8, and Seq ID No: 9. Preferably, the substantially pure Oncoimmunin-lymphoid factor of the present invention comprises an amino acid sequence selected from the group consisting of the following: Seq ID No: 3, Seq ID No: 4, Seq ID No: 5, Seq ID No: 6, Seq ID No: 7, Seq ID No: 8, and Seq ID No: 9.

Alternatively, the Oncoimmunin-lymphoid of this invention comprises a first amino acid sequence having at least 80%, preferably at least 90%, and still more preferably at least 95% sequence identity with a second amino acid sequence, said second amino acid sequence comprising Seq ID No: 3, Seq ID No: 4, Seq ID No: 5, Seq ID No: 6, Seq ID No: 7, Seq ID No: 8, and Seq ID No: 9. Preferably, the substantially pure Oncoimmunin-myeloid factor of the present invention comprises Seq ID No: 3, Seq ID No: 4, Seq ID No: 5, Seq ID No: 6, Seq ID No: 7, Seq ID No: 8, and Seq ID No: 9.

In another embodiment, this invention provides for a method of stimulating human T-lymphocyte mitogenesis in a mammal, more particularly a human. The method comprises administering to the mammal a substantially pure Oncoimmunin-lymphoid factor in an amount sufficient to stimulate T-lymphocyte mitogenesis. Even more particularly, the stimulated T-lymphocyte is a tumor infiltrating lymphocyte.

In yet another embodiment, the present invention provides a method of expanding tumor infiltrating lymphocytes ex vivo by culturing them with a substantially pure Oncoimmunin-lymphoid factor.

In still another embodiment, this invention provides for an antibody, more particularly a monoclonal antibody, or binding fragment thereof, having a binding affinity for the substantially pure Oncoimmunin-lymphoid factor.

This invention also provides for a method of detecting Oncoimmunin-lymphoid factor in a target sample, where the method comprises contacting the target sample with the above-described antibody and detecting the binding of the antibody to the target sample.

In another embodiment, this invention provides for diagnostic kits. A diagnostic kit comprises (i) the antibody or binding fragment described above; and (ii) a conjugate comprising a binding partner of said antibody. The diagnostic kit further comprises a label for detecting the conjugate.

This invention also provides for a pharmaceutical composition comprising substantially pure Oncoimmunin-lymphoid factor in an amount effective to stimulate human T-lymphocyte mitogenesis, and a pharmaceutically acceptable diluent, carrier, or excipient.

This invention also provides for methods of treating cancer in a patient. On one method comprises administering to the patient an effective amount of the pharmaceutical composition described above. Another method comprises reinfusing into the patient an amount of tumor infiltrating lymphocytes, wherein the tumor infiltrating lymphocytes have been expanded ex vivo by culturing them with a substantially pure Oncoimmunin-lymphoid factor.

In another embodiment the present invention also provides for a substantially pure Oncoimmunin-myeloid factor, derived from a tumor cell line, said factor having a molecular weight of about 36 kDa by SDS-PAGE analysis and having the ability to inhibit growth in a myeloid cell line or induce differentiation of a myeloid cell line, more particularly a human myeloid leukemic cell line HL-60, in an interleukin-2 and interleukin-4 free, serum-free medium. The inhibition of growth in a myeloid cell line is measured as a decrease in [$^3$H]-thymidine uptake by said myeloid cell line, while the differentiation of the myeloid cell line is measured as an increase in CD11b and CD11c integrins.

Even more particularly, the Oncoimmunin-myeloid factor also induces migration of myeloid cells to recombinant human C5a. This Oncoimmunin-myeloid factor may be recombinantly produced.

The invention provides for both a method of purifying the Oncoimmunin-myeloid factor from an interleukin-2 and interleukin-4 free, serum-free, conditioned medium of a tumor cell line, and the substantially pure Oncoimmunin-myeloid factor produced by the purification where the purification comprises the steps of:

a) subjecting the medium to an ion exchange chromatography, b) selecting from the chromatography, the early eluting fractions displaying bioactivity;

c) subjecting the early eluting fractions selected in step (b) to a hydrophobic interaction chromatography;

d) selecting the fractions from the hydrophobic interaction chromatography showing bioactivity; and e) subjecting the fractions selected in step (d) to a gel filtration chromatography; resulting in the purification of said factor;

wherein said bioactivity is measured as a decrease in the [$^3$H]-thymidine incorporation by a myeloid cell line and an increase in cell surface expression of CD11b integrin.

The substantially pure Oncoimmunin-myeloid factor comprises an amino acid sequence having at least 80%, preferably at least 90%, and still more preferably at least 95% sequence identity with an amino acid sequence selected from the group consisting of: Seq ID No: 1 and Seq ID No: 2. Even more preferably, the substantially pure Oncoimmunin-myeloid factor comprises an amino acid sequence selected from the group consisting of Seq ID No: 1 and Seq ID No: 2.

Alternatively, the substantially pure Oncoimmunin-myeloid factor comprises a first amino acid sequence having at least 80%, preferably at least 90%, and still more preferably at least 95% sequence identity with a second amino acid sequence, said second sequence comprising Seq ID No: 1 and Seq ID No: 2. Preferably the substantially pure Oncoimmunin-myeloid factor comprises the amino acid sequence shown in Seq. Id No: 1 and the amino acid sequence shown in Seq. Id No: 2.

In yet another embodiment, this invention provides a method of inhibiting growth of a myeloid cells or inducing differentiation of myeloid cells in a mammal, more particularly a human, where the method comprises administering to the mammal a substantially pure Oncoimmunin-myeloid factor in an amount sufficient to inhibit growth or induce differentiation of the myeloid cells.

This invention also provides for a method of inducing differentiation of myeloid cells ex vivo by culturing the myeloid cells with the substantially pure Oncoimmunin-myeloid factor.

This invention provides for an antibody, or binding fragment thereof, more particularly a monoclonal antibody, having a binding affinity for Oncoimmunin-myeloid factor.

According to the present invention, these antibodies may be used in a method of detecting Oncoimmunin-myeloid factors in a target sample. The method comprises contacting the target sample with the antibody and detecting binding between the antibody and the target sample.

In another embodiment, this invention provides for a diagnostic kit comprising an antibody or antibody binding fragment and a conjugate comprising a binding partner of the antibody. Preferably, the kit further comprises a label for detecting the conjugate.

In still yet another embodiment, this invention provides for an Oncoimmunin-myeloid pharmaceutical composition comprising substantially pure Oncoimmunin-myeloid factor and a pharmaceutically acceptable diluent, carrier, or excipient.

This invention also provides a method for treating cancer in a patient by administering to the patient the Oncoimmunin-myeloid pharmaceutical composition in an amount effective to induce myeloid differentiation. Additionally, the invention provides a method for treating opportunistic infections associated with AIDS or other immuno-compromised conditions in a patient comprising administering to the patient the Oncoimmunin-myeloid pharmaceutical composition in an amount effective to induce myeloid differentiation.

Alternatively, this invention also provides a method for treating cancer in a patient by reinfusing into the patient, myeloid cells differentiated ex vivo by culturing the myeloid cells with the substantially pure Oncoimmunin-myeloid factor. This invention also provides a method of treating opportunistic infections associated with AIDS or other immunosuppressed conditions in a patient by reinfusing into the patient, myeloid cells differentiated ex vivo by culturing the myeloid cells with the substantially pure Oncoimmunin-myeloid factor.

In yet another embodiment, this invention provides for a fusion protein comprising a substantially pure Oncoimmunin-lymphoid factor, derived from a tumor cell line, having a molecular weight of about 45 kDa by SDS-PAGE analysis and having the ability to stimulate T-lymphocyte mitogenesis in an interleukin-2 and interleukin-4 free, serum-free medium and a substantially pure Oncoimmunin-myeloid factor, derived from a tumor cell line, said factor having a molecular weight of about 36 kDa by SDS-PAGE analysis and having the ability to inhibit growth in a myeloid cell line or induce differentiation of a myeloid cell line in an interleukin-2 and interleukin-4 free, serum-free medium.

In another embodiment, this invention provides a method of activating, inducing differentiation and proliferation of lymphoid and/or myeloid cells ex vivo, by culturing the lymphoid and/or myeloid cells with a substantially pure Oncoimmunin-lymphoid factor, derived from a tumor cell line, having a molecular weight of about 45 kDa by SDS-PAGE analysis and having the ability to stimulate T-lymphocyte mitogenesis in an interleukin-2 and interleukin-4 free, serum-free medium and a substantially pure Oncoimmunin-myeloid factor, derived from a tumor cell line, having a molecular weight of about 36 kDa by SDS-PAGE analysis and having the ability to inhibit growth in a myeloid cell line or induce differentiation of a myeloid cell line in an interleukin-2 and interleukin-4, serum-free medium.

Alternatively this invention provides method of activating, inducing differentiation and proliferation of lymphoid and/or myeloid cells ex vivo, comprising culturing the lymphoid and/or myeloid cells with the above-described fusion protein.

Further objects and advantages of the present invention will be clear from the description that follows.

Figure 1A:
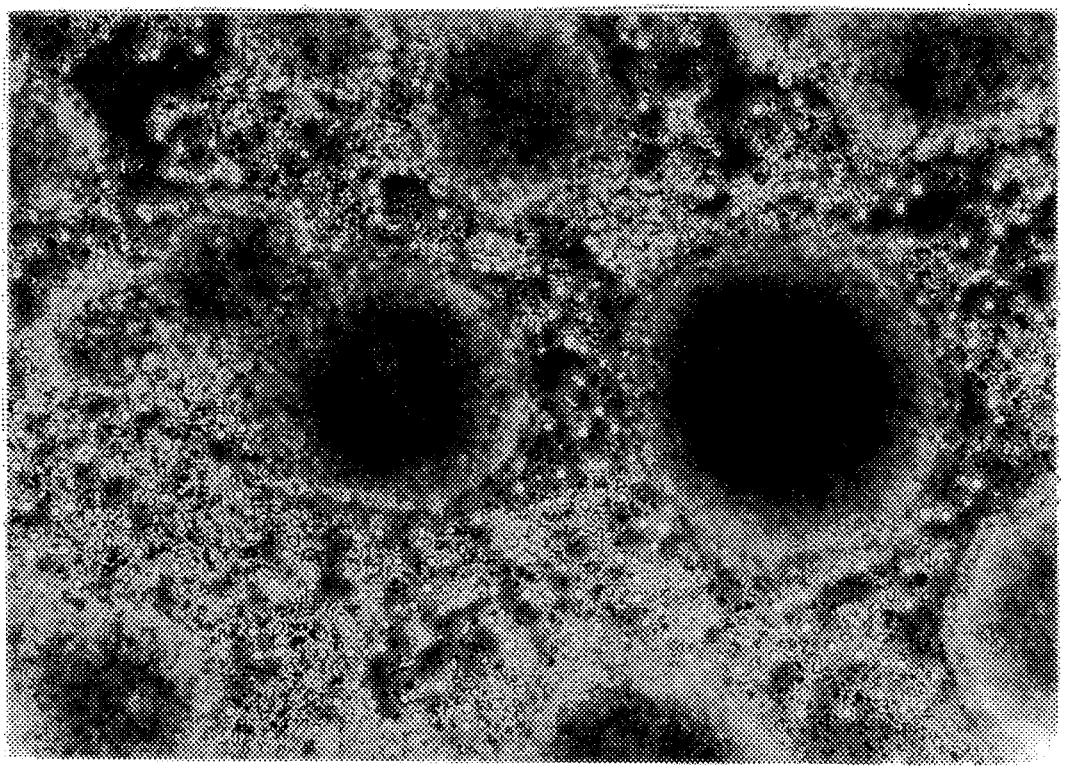
FIG. 1. Tumor infiltrating lymphocytes (TILs) growing in the absence (a) and presence (b) of 618 melanoma tumor cells. (Magnification: 110x).

FITC-antibody. (a) Oncoimmunin-M treated HL-60 cells. (b) Control (untreated) HL-60 cells. The enhanced expression of CD41 on HL-60 cells treated with Oncoimmunin-M is indicated by the observed increased binding of antibody to CD41 (a), as compared to the untreated control HL-60 cells (b).

FIG. 21. Flow cytometry FACScan histogram analysis showing leukocyte expression on Oncoimmunin-M treated HL-60 cells. Cells were labeled with FITC and PE fluorescent labeled antibodies specific to various leukocyte integrins. Labeled antibodies were: (A) CD18-FITC, (B) CD11a-FITC, (C) CD11b-PE, (D) CD11c-PE. (E) Leukocyte integrin expression on Oncoimmunin-M-treated and untreated HL-60 cells exposed to IgG antibodies to determine the autofluorescence level of the HL-60 cells. Ten thousand cells per sample were analyzed with a FACScan flow cytometer (Becton Dickinson, Mountain View, Calif., U.S.A.). All experiments were performed a minimum of three times.

FIG. 22. Migratory responses of Oncoimmunin-M-treated and control HL-60 cells to: (A) recombinant human C5a ($10^{-12}$ to $10^{-7}$ M); (B) recombinant interleukin-8 ($10^{-2}$ to $10^{-4}$ ng/ml); and (C) f-Met-Leu-Phe peptide ($10^{-10}$ to $10^{-6}$ M). Chemotaxis was assayed in multiwell chemotaxis chambers. The data represent the total number of migrating cells per square millimeter of filter surface, and are presented as the mean ± 1 SD of triplicate assays from individual experiments. The values of each assay represent the means of five measurements in each assay (5 fields×3 assays=15 fields). Experiments were performed eight times. The total Oncoimmunin-M-treated population showed from 10% to 35% migration.

FIG. 23. Myeloid integrin expression on motile (shaded areas) and nonmotile (nonshaded areas) subpopulations of Oncoimmunin-M treated HL-60 cells. Antibodies used are listed in the legend of FIG. 21. The nonmotile subpopulation exhibited homogeneous distributions of CD18 and CD11a, and heterogenous expression of CD11b and CD11c. In contrast, the motile subpopulation exhibited homogeneous, high expression of CD11b and CD11c, while the CD11a and CD18 levels remained homogeneous. These findings suggest that expression levels of the two myeloid integrin subunits (i.e., CD11b and CD11c) or the conformational determinants of epitopes for the antibodies used in this Example are differentially modulated on motile and nonmotile cells as a function of Oncoimmunin-M treatment.

DETAILED DESCRIPTION OF THE INVENTION

Definitions

As used herein the term "Oncoimmunin" refers to a soluble factor derived from a solid tumor with immunomodulatory activity. The type of immunomodulatory activity depends both on the particular Oncoimmunin and the particular target cell. Thus immunomodulatory activity of Oncoimmunin-lymphoid factors includes mitogenic activity for lymphocytes, while immunomodulatory activity for Oncoimmunin-myeloid factors includes reduction of [$^3$H]-thymidine incorporation, induction of chemotactic activity, and the expression of cell surface integrins by myeloid cells.

The term "interleukin-free" as used herein, refers to a medium in which the interleukin in question cannot be detected using a standard assay for the presence of that interleukin. Thus, for example, a medium is interleukin-2 and interleukin-4 free when these interleukins cannot be detected by an enzyme-linked immunosorbent assay (ELISA).

The term "having a binding affinity" refers to the propensity of a molecule to preferentially bind or attach to a specific "target" molecule. Thus antibodies raised against a specific antigen have a binding affinity for that antigen. They tend to bind or attach to that antigen and not to other molecules that may be present.

The term "growth" as used herein refers either to the metabolic rate of a cell and/or its propensity to multiply or proliferate. Growth may be measured by recording the change in cell size, number, or metabolic activity over time. Metabolic activity is often the most convenient measure of growth and may be assayed by the rate of incorporation of a metabolic substrate (e.g., [$^3$H]-thymidine) or by measuring the amount of metabolic substrate incorporated in a given time. Thus growth inhibition may be assayed as a decrease in [$^3$H]-thymidine incorporation by a cell, while proliferation, mitogenesis or growth increase may be assayed as an increase in [$^3$H]-thymidine incorporation by a cell The phrase "displaying bioactivity" refers to the properties of a composition observed by its effect on living cells. Thus a composition displaying bioactivity in the present invention may induce cell proliferation, increase or decrease cell metabolic rate as measured by the rate of incorporation of [$^3$H]-thymidine, induce differentiation (e.g., the expression of particular cell surface markers), or induce a behavioral response such as chemotaxis.

The expression "inducing differentiation" is used herein to refer to the induction of the appearance of cell surface markers present on cells generally described as more differentiated then similar cells lacking those markers. Thus, in the present invention, myeloid cells are considered further differentiated when the expression of integrins (e.g. CD11b, CD11c) is increased on the cell surface.

"Isolated" or "biologically pure" or "substantially pure" refers to material which is purified to homogeneity or essentially free from components which normally accompany it as found in its native state. Thus, the purified Oncoimmunins of the present invention do not contain materials normally associated with their in situ environment.

The term "mitogenic" refers to the ability of a composition to induce cell mitosis and consequent proliferation of that cell type.

The term "conditioned" when used herein to describe media, refers to medium wherein tumor cells have been cultured. Thus, in addition to components of the base medium, conditioned medium also comprises compounds resulting from the tumor cell culture. Such compounds may be secreted by the cells or may result from cell lysis, or may result from the interaction of components of the base medium and the above compounds.

The term "recombinant protein" or "recombinantly produced protein" refers to a peptide or protein produced using cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The term "antibody", as used herein, includes various forms of modified or altered antibodies, such as an intact immunoglobulin, an Fv fragment containing only the light and heavy chain variable regions, a Fab or (Fab)'2 fragment containing the variable regions and parts of the constant regions, a single-chain antibody and the like (Bird et al., Science, 242:424–426 (1988); Huston et al., *Proc. Natl. Acad. Sci. USA*, 85:5879–5883 (1988)). The antibody may be of animal (especially mouse or rat) or human origin or may be chimeric (Morrison et al., *Proc Nat. Acad. Sci. USA*, 81: 6851–6855 (1984)) or humanized (Jones et al., *Nature*, 321: 522–525 (1986), and published UK patent application #8707252). Methods of producing antibodies suitable for use in the present invention are well known to those skilled in the art and can be found described in such publications as Harlow & Lane, *Antibodies: A Laboratory Manual*, Cold Spring Harbor Laboratory (1988), and Asai, *Methods in Cell Biology Vol. 37: Antibodies in Cell Biology*, Academic Press, Inc. N.Y. (1993).

DESCRIPTION OF THE PREFERRED EMBODIMENTS

The idea that the tumor environment contains lymphocytes which may exhibit antitumor activity was the basis for using lymphocytes expanded in culture as therapeutic agents (Treves, A. J. et al., *J. Natl. Cancer Inst.* 54:777–780 (1975); Lee, et al., *J. Exp. Med.* 147:912–922 (1978); Zarling, et al., *Nature* (London), 280:685–687 (1979); Vose, et al., *Nature* (London), 296:359–361 (1982); Vose, et al., *Int. J. Cancer*, 29:33–39 (1982); Vanky, et al., *J. Exp. Med.*, 155:83–95 (1982); Mitsuya, et al., *J. Exp. Med.*, 158:994–999 (1983); De Vries, et al., *J. Immunol.*, 132:510–519 (1984); Slovin, S. F. et al., *J. Immunol.*, 137:3042–3048 (1986); Itoh, K. et al., *Cancer Res.* 46:3011–3017 (1986); Rosenberg, et al., *Science* 233:1318–1321 (1986); Rabinowich, et al., *Cancer Res.* 47:173–177 (1987); Miescher, et al., *J. Immunol.* 138:4004–4011 (1987); Kradin, et al., *Cancer Immunol. Immunother.* 24:76–85 (1987)). Much work supports the concept that an immune response is initiated against tumors via direct tumor cell lymphocyte contact, followed by the secretion of factors mitogenic for lymphocytes from several immunocyte sources.

Initially, the issue of whether a tumor cell line established from a melanoma tumor could stimulate the growth of tumor infiltrating lymphocytes (TILs) derived from melanoma masses was examined. After confirming the mitogenic potential of three melanoma cell lines, a non-melanoma tumor cell line was tested for the same bioactivity and found to be at least as potent a mitogenic source.

Tumor-derived mitogenic activity for TILs could be ascribed to secreted factor(s) as mitogenic activity for TILs was found in the serum free conditioned medium. Immunologic and proliferative assays indicate nonidentity of at least one secreted factor with any previously characterized lymphokine.

Purification of the serum-free conditioned medium revealed two secreted factors. The first, designated Oncoimmunin-lymphoid factor or Oncoimmunin-L, induces proliferation of TILs, while the second, designated Oncoimmunin-myeloid factor or Oncoimmunin-M, induces differentiation of myeloid cells. Thus, the present invention provides Oncoimmunins which are either mitogenic (Oncoimmunin-L) for Tumor-Infiltrating Lymphocytes (TILs) or which induce differentiation in myeloid cells (Oncoimmunin-M).

Detection of Oncoimmunins and Identification of Oncoimmunin Sources

Tumor-infiltrating lymphocytes have shown in vivo antitumor efficacy in both animal and human studies. Functions thought necessary for antitumor activity include cytolysis, homing, and proliferation at tumor sites. TILs which are T-lymphocytes grown ex vivo directly from tumors, bear interleukin-2 (IL-2) receptors capable of transducing the IL-2 mitogenic signal. However, IL-2 is not normally synthesized by solid tumor cells. In order to explore the possible presence of T-cell mitogens of tumor origin, TIL lines, derived from four melanoma patients were assayed for their ability to use the environments of cultured tumor cell lines as mitogenic sources. The presence of four irradiated cultured human tumor cell lines, three of which were derived from the same melanoma patients as the TILs, were found to stimulate proliferation of human TILs in the absence of IL-2. The observed proliferative stimulation by the tumor cell lines was due to secreted factor(s) as mitogenic activity was present in the serum-free tumor cell supernatant. Immunologic analyses of this medium and assays for biological activity showed the presence of two factors: one a T-cell mitogen, and the other, a factor that induces differentiation in myeloid cells.

The Oncoimmunins of the present invention may be derived from media conditioned by the culture of solid tumor cells. These tumor cells may either be commercial cell lines, such as A431 cells easily obtained from a supplier (e.g., American Type Culture Collection (ATCC), Rockville, Md., U.S.A.) or, alternatively, the cells may be obtained directly from mammals bearing melanoma tumors and cultured using standard techniques. Mammalian sources of these tumor cells will generally include those well known in the art, for example, monkey, mouse, rat, and rabbit. Preferably, the tumor cells are human melanoma cells. Techniques for the culture of mammalian tumor cells are well known in the art and described in references such as *Readings in Mammalian Cell Culture*, R. Pollack, ed. Cold Spring Harbor Laboratory Press, Cold Spring Harbor, N.Y. (1981).

Tumor-derived factors may be detected by assaying for biological activity in coculture experiments where the assay cells are cultured together with gamma irradiated tumor cells. Alternatively, medium conditioned by the tumor cells may be screened for activity. The isolated or purified Oncoimmunin-L or Oncoimmunin-M may also be detected by using antibodies against these factors. Finally, DNA encoding Oncoimmunin-L or Oncoimmunin-M may be detected by using hybridization probes specific for the nucleotide sequences encoding the particular Oncoimmunin in question.

The assay conditions are critical in identifying the Oncoimmunin activities. Two days prior to performing the assay, the assay T-cells or myeloid cells must be removed from the IL-2 or serum-containing medium and placed in serum-free medium. Use of cells after one or three days will not lead to the successful detection of activity for Oncoimmunin-L. This optimization time differs from the routine procedure of simply washing the cells and using them immediately or at one day. Optimization of mitogenic activity is at 24 hours after commencement of the assay.

Mitogenic activity of Oncoimmunin-L may be detected through measurement of signals correlated with T-cell activation. Such signals are well known in the art and include such phenomena as up or down regulation of cell surface receptors, increased uptake and incorporation of [$^3$H]-thymidine into DNA, secretion of cytokines, changes in membrane potential or alterations in metabolic rate. These signals may be detected by measuring the binding of monoclonal antibodies to cell receptors and plasma membrane proteins, monitoring transmembrane potential changes with patch clamps or measuring the uptake of labeled metabolic substrates (e.g., labeled nucleotides). In a preferred embodiment, incorporation of [³H]-thymidine into the TIL cell DNA is used as a measure of T-cell proliferation.

Similarly, the activity of Oncoimmunin-M in inducing differentiation of myeloid cells may be determined by monitoring any signal correlated with myeloid cell differentiation. Such signals are well known to those of skill in the art and may include, for example, a decrease in proliferative rate of the cells, or expression of particular cell surface markers. One such marker is a surface molecule recognized by the CD11b antibody. In a preferred embodiment, myeloid differentiation is measured as a decrease in [³]-thymidine uptake into cellular DNA of myeloid cells.

Purification of Oncoimmunins

Oncoimmunins may be purified from the serum-free supernatant by a combination of standard techniques for peptide and protein purification. Such protein purification methods are generally described in a number of references. See, for example, *Methods in Enzymology Volume* 182, *Guide to Protein Purification*, M. Deutscher, ed. Academic Press Inc. N.Y. (1990) and *Methods in Enzymology Volume* 104, *Enzyme Purification and Related Techniques*, W. B. Jakoby, ed. Academic Press Inc. N.Y. (1984). After each purification step, the fractions displaying the desired activity, as determined by the above-mentioned assays, are isolated, and, if necessary, subject to further purification steps.

In a preferred embodiment of this invention, the serum-free conditioned medium is fractionated using an ion exchange (Q-Sepharose Fast Flow) column. Using [³H]-thymidine uptake by TILs as an assay, an early eluting and a late eluting bioactive domain are detected. The late-eluting fractions are then subjected to gel filtration (Sephacryl S-300), another ion exchange chromatography (Mono-Q using FPLC) and $C_4$ reverse phase HPLC to produce Oncoimmunin-L purified to homogeneity.

In another embodiment, the serum-free conditioned medium is fractionated using an ion exchange (Q-Sepharose Fast flow) column. Using [³H]-thymidine uptake by TILs as an assay, an early eluting and a late eluting bioactive domain are detected. The early-eluting fractions are then subject to hydrophobic interaction chromatography (Phenyl Superose) followed by gel filtration chromatography (Sephacryl S-300) to produce Oncoimmunin-M purified to homogeneity. Bioactive fractions from the gel filtration are assayed for inhibition of [³H]-thymidine uptake by myeloid cells (e.g., HL-60 cells).

Recombinant Production of Oncoimmunins

In addition to the methods described above, the present invention also encompasses methods of producing the claimed Oncoimmunins using recombinant DNA technology.

1. Isolation of DNA

The amino acid sequence of part or all of the purified Oncoimmunin-L and Oncoimmunin-M of the present invention may be obtained by methods generally well known in the art. From the partial or entire amino acid sequence, the nucleic acid sequence can be isolated. To accomplish this, regions of low degeneracy (i.e., amino acid sequences wherein substantially every amino acid has only a single codon encoding therefor) may be determined from the amino acid sequence. From these amino acid sequence regions, nucleotide sequences can be predicted for each degenerate form. Because the region was chosen for its low degeneracy, there will be few, or one, possible nucleotide sequence(s) encoding these regions.

Complementary nucleic acid probes are then synthesized using the above predicted sequences by chemical synthesis methods which are generally well known in the art. See, for example, the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Letts.* 22:1859–1862 (1981); and the solid support method of U.S. Pat. No. 4,458,066. Where there is more than a single possible predicted DNA sequence (i.e., the region is "degenerate") probes for each DNA sequence may be synthesized or alternatively degenerate probes may be used (e.g., with inosine substituting for the nucleic acid at each position where there are multiple choices).

A cDNA library may be constructed from human tumor cells by methods generally well known in the art, e.g., in bacteriophage λ, or a plasmid for mammalian cell expression (Sambrook, et al., *Molecular Cloning: A Laboratory Manual* (2d ed.), Vols. 1–3, Cold Spring Harbor Laboratory Press, Cold Spring Harbor, N.Y. (1989) hereinafter referred to as Sambrook, et al.). The above probes may either be used to directly screen the library for exact hybridization to cDNA, or they may be used as primers for PCR amplification, wherein the amplified sequences may be used as probes. Multiple probes from different regions of low degeneracy may be employed to ensure accurate identification of the correct cDNA sequence. Once isolated, the isolated DNA is sequenced to confirm that it encodes the Oncoimmunins of the present invention.

2. Expression of DNA Encoding Oncoimmunins

The nucleic acids isolated using the above methods are useful for making large amounts of the Oncoimmunin factors. The DNA fragment encoding the desired Oncoimmunin, or portions thereof, will be used to prepare an expression construct by methods well known in the art. The expression construct normally comprises one or more DNA sequences encoding the desired Oncoimmunin under the transcriptional control of a native or other promoter. Usually the promoter will be a eukaryotic promoter for expression in a mammalian cell, where the mammalian cell may, or may not, lack the Oncoimmunin factors. The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known (Id.).

Conveniently available expression vectors can be employed, including the replication system and transcriptional and translational regulatory sequences together with the insertion site for the Oncoimmunin DNA sequence. Examples of workable combinations of cell lines and expression vectors are also known (Sambrook, et al.; Metzger, et al., *Nature* 334:31–36 (1988)). In particular, non-fungal promoters will be preferred where expression occurs in non-fungal cells. Occasionally, it might be useful to express the sequences in other types of cells, and appropriate promoters may be selected. In some circumstances, an inducible promoter is preferred. In other circumstances, it will be desired to coexpress a glycosylation enzyme which will provide a glycosylation pattern similar to that provided by a desired cell type.

In cases where one wishes to expand the DNA sequence or produce the Oncoimmunin protein or fragments thereof in a prokaryotic host, a preferred promoter is a prokaryotic promoter, e.g., trp, lac, and lambda. Usually a strong promoter will be employed to provide for high levels of transcription and expression.

The expression construct will often be contained in a vector capable of stable extrachromosomal maintenance in an appropriate cellular host or may be integrated into the host genome. The expression construct can be bordered by sequences which allow for insertion into a host, such as transposon sequences, lysogenic viral sequences, or the like. Normally, markers are provided with the expression construct which allow for selection of host cells containing the construct. The marker can be on the same or a different DNA molecule, preferably on the same DNA molecule.

In mammalian cells, the gene itself can often provide a convenient marker. However, in prokaryotic cells, markers such as a resistance to a cytotoxic agent or antibiotic, complementation of an auxotrophic host to prototrophy, production of a detectable product, etc., will be more convenient.

The expression construct can be joined to a replication system recognized by the intended host cell. Various replication systems include viral replication systems such as retroviruses, simian virus, bovine papilloma virus, or the like. In addition, the construct can be joined to an amplifiable gene, e.g., dihydrofolate reductase (DHFR) gene, so that multiple copies of the desired Oncoimmunin gene can be made (Schimke, R., Cell 37:705–713 (1984); Kaufman, et al., Mol. Cell Biol. 5:1750–1759 (1985)).

Where it is desirable to express Oncoimmunin polypeptide having a mammalian glycosylation pattern, the polypeptide, e.g., an unglycosylated form, can be exposed to appropriate glycosylating proteins introduced into a heterologous expression system. For example, the Oncoimmunin gene can be co-transformed with one or more genes encoding mammalian or other glycosylating enzymes, preferably originating from a non-fungal species, and in some embodiments, non-human species. Using this approach, certain mammalian glycosylation patterns will be achievable in prokaryote or other cells.

A wide variety of hosts will be employed for expression of the Oncoimmunin factors, both prokaryotic and eukaryotic. Useful hosts include bacteria, such as E. coli, yeast, filamentous fungi, insect cells, mammalian cells, typically immortalized, e.g., various mouse cell lines, monkey cell lines, Chinese hamster ovary cell lines, human cell lines, derivatives of them, or the like. In some cases, the cells will be derived from a neoplastic host cell or wild-type cells will be transformed with oncogenes, tumor causing viruses or the like.

The means of introduction of the expression construct into a host cell will vary depending upon the particular construction and the target host. Introduction can be achieved by any convenient means, including fusion, conjugation, transfection, transduction, electroporation, injection, or the like (Sambrook, et al.). Introduction of constructs encoding different forms of the protein into a single host cell is also contemplated. The host cells will normally be immortalized cells, i.e., cells that can be continuously passaged in culture. For the most part, these cells will be convenient mammalian cell lines which are capable of expressing the Oncoimmunins and, where desirable, process the protein so as to provide an appropriate mature protein. By processing is intended glycosylation, ubiquitination, disulfide bond formation, general post-translational modification, or the like. If secretion is desired, a transmembrane sequence, if present in the protein, will generally be deleted or mutated to prevent membrane localization of the protein.

3. Isolation of the Expressed Oncoimmunin

Oncoimmunins produced by prokaryotic cells may not necessarily fold properly. During purification from E. coli, the expressed protein may first be denatured and then renatured. This can be accomplished by solubilizing the bacterially produced proteins in a chaotropic agent such as guanidine HCl and reducing all the cysteine residues with a reducing agent such as beta-mercaptoethanol. The protein is then renatured, either by slow dialysis or by gel filtration. See U.S. Pat. No. 4,511,503.

The polypeptides produced by recombinant DNA technology may be purified by standard techniques well known to those of skill in the art. Recombinantly produced polypeptides can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired polypeptide.

The polypeptides of this invention may be purified to substantial purity by standard techniques well known in the art, including selective precipitation with such substances as ammonium sulfate, column chromatography, immunopurification methods, and others (Scopes, Protein Purification: Principles and Practice, Springer-Verlag: New York (1982)). For example, antibodies may be raised to the Oncoimmunins proteins as described herein. Cell membranes are isolated from a cell line expressing the recombinant protein, the protein is extracted from the membranes and immunoprecipitated. The proteins may then be further purified by standard protein chemistry techniques (e.g., Methods in Enzymology Volume 182, Guide to Protein Purification, M. Deutscher, ed. Academic Press Inc. N.Y. (1990)).

Functionally Equivalent Proteins

Cells transfected, injected, infected or electroporated with DNA or mRNA containing a full length natural Oncoimmunin sequence will often express the native or wild type protein and respond accordingly. Less than full length segments will often have desired equivalent functions.

Proteins which have substantial amino acid sequence identity to Oncoimmunin-M or Oncoimmunin-L are also encompassed within the scope of the present invention. A protein having substantial sequence identity will generally have at least about 30% sequence identity, preferably at least 50% amino acid sequence identity, more preferably from about 70% to about 80% sequence identity, still more preferably at least about 90% sequence identity, and most preferably at least about 95% sequence identity to Oncoimmunin-M or to Oncoimmunin-L of this invention.

Two polypeptides are said to be "identical" if the sequence of amino acid residues in the two sequences is the same when the polypeptides are aligned for maximum correspondence as described below. Identical polypeptides have 100% sequence identity with each other.

Sequence comparisons between two (or more) polypeptides are typically performed by comparing regions of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Percentage of sequence identity is determined by comparing two optimally aligned sequences or subsequences over a comparison window or span, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical subunit (e.g., nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Optimal alignment of sequences for comparison may be conducted by the local homology algorithm of Smith and Waterman, *Adv. Appl. Math.* 2:482 (1981), by the homology alignment algorithm of Needleman and Wunsch *J. Mol. Biol.* 48: 443 (1970), by the search for similarity method of Pearson and Lipman, *Proc. Natl. Acad. Sci. USA* 85:2444 (1988), by computerized implementations of these algorithms (including, but not limited to CLUSTAL in the PC/Gene program by Intelligenetics, Moutain View, Calif., GAP, BESTFIT, FASTA, and TFASTA in the Wisconsin Genetics Software Package, Genetics Computer Group (GCG), 575 Science Dr., Madison, Wis., USA), or by inspection. In particular, methods for aligning sequences using the CLUSTAL program are well described by Higgins and Sharp in *Gene*, 73:237–244 (1988) and in *CABIOS* 5:151–153 (1989)

Specifically embodied within the scope of this invention are variants of the Oncoimmunins herein described, where such variants have mutations in the amino acid sequence. These mutations may include substitution, addition, or deletion of amino acid residues to enhance activity or reduce immunogenicity. Such mutations may be made by random or site directed mutagenesis.

Oncoimmunin Complexes

Various complexes of Oncoimmunin-M and/or Oncoimmunin-L are also embodied within the scope of the present invention. These complexes include monomeric, dimeric, trimeric, tetrameric and even polymeric forms of the Oncoimmunins, both linear or cyclic. The monomeric subunits in such complexes may be linked by disulfide bonds, hydrogen bonds, hydrophobic bonds, ether bonds, peptide bonds, or other known means of linking polypeptides including peptide and carbon chain linkers containing two or more functional groups capable of binding the respective peptides. Further, such complexes may be a result of natural aggregation, or may be produced artificially by generally known methods. Complexes of the Oncoimmunins may increase antigenicity or serum stability and modulate specific activity.

Oncoimmunin Fusion Proteins

In addition to the above complexes, the present invention also encompasses Oncoimmunin-L and Oncoimmunin-M when expressed as fusion proteins, or when produced as conjugates with peptides or other compounds. Expression as a fusion protein or as a conjugate will prolong the serum clearance period or stabilize and protect the Oncoimmunins from protease degradation.

Such fusion proteins generally incorporate the full length Oncoimmunin or a fragment thereof, which is expressed in a single polypeptide chain with additional peptide(s). The additional peptides may include full length proteins which can serve as targets or ligands to aid in purification, labels for the Oncoimmunin, adjuncts useful therapeutic applications, signal peptides for directing the processing of the Oncoimmunin within the expressing host cell, or antibodies or fragments thereof useful in specifically targeting the Oncoimmunins in vivo. Fusion proteins embodied herein can be produced by methods generally well known in the art (Sambrook et al.; *Mol. Biol. of the Cell*, Alberts et al. (eds.), Garland Pub. N.Y., pp. 267–8 (1989)).

Conjugated peptides containing the Oncoimmunins of the present invention will generally include the full length Oncoimmunin or a fragment thereof, coupled to additional compounds, wherein the additional compounds may be labelling compounds, purification targets or ligands, or adjuncts to improve or alter the efficacy of the Oncoimmunin.

Use of Oncoimmunins in Adoptive Immunotherapy

Oncoimmunins may be particularly useful in adoptive immunotherapy for cancer treatment. In a preferred embodiment Oncoimmunin-L may be used in adoptive immunotherapy to expand TILs derived from a melanoma patient ex vivo. Such immunotherapy generally involves removing tumor cells from a patient, culturing these cells in the presence of Oncoimmunin-L to induce TIL proliferation, and harvesting TILs from the culture. The expanded TILs may then be infused back into the patient where they are cytotoxic for the tumor cells. Methods of adoptive immunotherapy using mitogens to induce ex vivo expansion of TILs are well known in the art (Rosenberg, et al., *New Engl. J. Med.* 319:1676–1680 (1988)).

Similarly, in another embodiment, adoptive immunotherapy may be performed using Oncoimmunins to recruit uncommitted myeloid cells via ex vivo activation. As with TILs, the treatment of tumors using activated myeloid cells can be particularly useful (Arjan, et al., *Cancer Immunol. Immunother.*, 34:393–398 (1992); Andreesen, et al., *Pathobiology*, 59:259–263 (1991); Bartholeyns, et al., *Anticancer Res.* 11:1201–1204 (1991); Boccoli, et al., *Cancer Res.* 50:5795–5800 (1990); Andreesen, et al., *Cancer Detection and Prevention*, 15:413–421 (1991)). This immunotherapy has been demonstrated using interferon-gamma or tumor necrosis factor α (TNF-α) to induce differentiation of uncommitted myeloid cells into tumor cytotoxic macrophages.

In this embodiment, mononuclear cells are harvested from a patient, generally from circulating blood or from bone marrow. These cells are activated ex vivo using Oncoimmunin-M to induce differentiation of the myeloid cells into tumor cytotoxic macrophages. These macrophages are then infused back into the patient where they participate in an immune response directed towards the tumors or towards infections.

The quantities of agents (Oncoimmunin-L alone and Oncoimmunin-M alone or combined) necessary for effective ex vivo activation and expansion of target cells in adoptive immunotherapy range from 0.01 nM to 1 µM. Once the cells have been expanded in culture, they are washed, concentrated and reinfused into patients as described in the literature (Rosenberg, et al., *New Engl. J. Med.* 319:1676–1680 (1988); Arjan, et al., *Cancer Immunol. Immunother.*, 34:393–398 (1992); Andreesen, et al., *Pathobiology*, 59:259–263 (1991); Bartholeyns, et al., *Anticancer Res.* 11:1201–1204 (1991); Boccoli, et al., *Cancer Res.* 50:5795–5800 (1990); Andreesen, et al., *Cancer Detection and Prevention*, 15:413–421 (1991)).

The macrophages described above, may also be used as microbicidal cells (Anderson et al., *Ann. Rev. Med.*, 38:175–194 (1987)). Thus induction of myeloid differentiation may also be used in preventing or treating infectious diseases. Such diseases include infections associated with AIDS, SCID, tuberculosis, and inherited immunodeficiency diseases such as Leu-CAM or CD11/CD18 deficiency, etc. (Arnaout, *Blood*, 75: 1037–1050 (1990); Hibbs, et al., *J. Clin. Invest.*, 85:74–681 (1990)). Specifically, such treatment may be used in fighting existing bacterial infections, as in AIDS patients, or to prevent infections in patients during reconstitution after bone marrow ablative chemotherapy, bone marrow transplant associated infections. Similarly, such treatment may serve to accelerate hematopoietic recovery and to prevent opportunistic infections in bone marrow transplant patients.

Pharmacological Compositions

In another embodiment, direct administration of Oncoimmunins, in a pharmacological composition, to human patients will result in in vivo activation of TILs or recruitment and differentiation of macrophages which then participate in an immune response targeting tumors and infections. Such pharmaceutical compositions are particularly useful in the treatment of cancer and infections. Specifically, TILs or tumor specific macrophages can attack a tumor in a cancer patient, and destroy the tumor cells, thus reducing or eliminating the tumor. Additionally, use of Oncoimmunin-L, by reducing the amount of IL-2 required to activate TILs, may reduce the toxic side effects associated with the administration of large doses of IL-2.

The quantities of agents necessary for effective therapy will depend upon many different factors, including means of administration, target site, physiological state of the patient, and other medicants administered. Thus, treatment dosages should be titrated to optimize safety and efficacy. These compounds can be administered to mammals for veterinary use and for clinical use in humans in a manner similar to other therapeutic agents, that is, in a physiologically acceptable carrier. In general, the administration dosage will range from about 0.00001 to 10 mg/kg, and more usually 0.0001 to 0.1 mg/kg of the host body weight. There are a variety of considerations which must be taken into account in determining the precise dosage, and these are generally described in the art (Gilman et al., (eds) Goodman and Gilman's: *The Pharmacological Bases of Therapeutics*, 8th Ed., Pergamon Press (1990); *Remington's Pharmaceutical Sciences*, 17th ed., Mack Publishing Co., Easton, Pa. (1990)).

Pharmaceutically acceptable carriers or diluents will include water, saline, buffers, and other compounds described in the literature (*Merck Index*, Merck & Co., Rahway, N.J.). Slow release formulations, or slow release apparatus will often be utilized for continuous administration.

The pharmaceutical compositions will be administered by parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the Oncoimmunin proteins, when administered orally, must be protected from digestion. This is typically accomplished either by complexing the Oncoimmunin with a composition to render it resistant to acidic and enzymatic hydrolysis or by packaging the protein in an appropriately resistant carrier such as a liposome. Means of protecting proteins from digestion are well known in the art.

The pharmaceutical compositions will often be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.4% saline, and the like. The liquid formulation may contain a reducing agent such as dithiothreitol (0.1 nM to 1 mM), metal chelator (EDTA or EGTA at 0.1 nM to 10 mM), or a stabilizer human serum albumin (0.1 µg/ml to 200 mg/ml). The formulation may also contain a preservative for an injectable vial formulation. These compositions will sometimes be sterilized by conventional, well known sterilization techniques, or can be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

Where the therapeutic composition is a solid, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. Where the therapeutic composition is administered orally, a pharmaceutically acceptable nontoxic composition is formed by incorporating any of the normally employed excipients, such as those carriers previously listed, and generally 0.001 to 10% of active ingredient, preferably about 1% combined with acid neutralizing compounds such as bicarbonates and various lipids.

Production of Antibodies Specific to Oncoimmunins

Full length Oncoimmunins or fragments thereof will be useful for producing antibodies, either polyclonal or monoclonal. Antibodies are produced by immunizing an appropriate vertebrate host, (e.g., a rat, mouse, rabbit or hamster) with the protein or fragment alone or in conjunction with an adjuvant. Usually two or more immunizations will be involved, and the blood or spleen will be harvested a few days after the last injection.

To produce polyclonal antibodies, an appropriate target immune system is selected, typically a mouse or rabbit, although another species sometimes will be substituted for a mouse or rabbit, including goats, sheep, cows, guinea pigs, and rats. The substantially purified antigen is presented to the immune system in a manner determined by methods appropriate for the animal and other parameters well known to immunologists. Typical sites for injection are in the footpads, intramuscularly, intraperitoneally, or intradermally. The immunoglobulins produced by the host can be precipitated, isolated and purified, including affinity purification. Techniques for producing polyclonal antibodies are well known to those of skill in the art (Drenckhahn, et al., pp. 8–54 In: *Antibodies in Cell Biology*, D. J. Asai, ed. Academic Press, Inc. N.Y. (1993)).

To produce monoclonal antibodies, appropriate animals will be selected and the desired immunization protocol followed. After the appropriate period of time, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen. Techniques for producing antibodies are well known to those of skill in the art. See, for example, Goding, et al., *Monoclonal Antibodies: Principles and Practice* (2d ed.) Academic Press, N.Y., Harlow, et al., *Antibodies: A Laboratory Manual*, Cold Spring Harbor Laboratory Press, Cold Spring Harbor, N.Y. (1988), U.S. Pat. Nos. 4,381,292, 4,451,570 and 4,618,577. Other suitable techniques involve in vitro exposure of lymphocytes to the antigenic polypeptides or alternatively to selection of libraries of antibodies in phage or similar vectors (Huse, et al., *Science*, 246:1275–1281 (1989)). Monoclonal antibodies with dissociation constants of $10^{-8}$ M, preferably $10^{-8}$ to $10^{-10}$ M, will typically be made by these standard procedures.

The antibodies specific to Oncoimmunin-M or Oncoimmunin-L can be used for a number of purposes, for example in immunoassays, as probes, for inhibiting Oncoimmunin activity, in diagnostics or therapeutics, or in basic studies seeking to dissect the portions of the proteins responsible for their biological activity or other functions.

An immunological response is usually measured or detected with an immunoassay. Normally such immunoassays involve some purification of a source of antigen, for example, produced by the same cells and in the same manner as the antigen being detected. The immunoassay will, in some instances, be a radioimmunoassay, an enzyme-linked assay (ELISA), a fluorescent assay, an enzyme inhibition assay, or any of many other choices, most of which are functionally equivalent but may exhibit advantages under specific conditions.

The antibodies of the present invention can be used with or without modification. Frequently, the antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277, 437; 4,275,149; and 4,366,241, 4,751,286, 4,889,916; and also recombinant immunoglobulins can be produced, see U.S. Pat. No. 4,816,567.

Chimetic antibodies specific for Oncoimmunin-M or Oncoimmunin-L are also embodied within the present invention. Such chimeric antibodies will generally consist of human constant regions, and variable binding regions from another mammalian antibody, most preferably a mouse antibody. Such chimeric antibodies are generally well known in the art. See, for example, Reichman et al., *Nature*, 332:323–27 (1988) and Boulianne et al., *Nature*, 312:643–46 (1984).

This invention also embodies human and humanized antibodies. Techniques for generation of human monoclonal antibodies have also been described but are generally more onerous than murine techniques and not applicable to all antigens. (See Larrick et al., U.S. Pat. No. 5,001,065 for a review). An alternative approach is the generation of humanized antibodies by linking the CDR regions of non-human antibodies to human constant regions by recombinant DNA techniques. See Queen et al., *Proc. Natl. Acad. Sci. USA* 86: 10029–10033 (1989) and WO 90/07861.

Alternatively, one may isolate DNA sequences which encode a human monoclonal antibody or a binding fragment thereof by screening a DNA library from human B cells according to the general protocol outlined by Huse et al., *Science* 246:1275–1281 (1989), and then cloning and amplifying the sequences which encode the antibody (or binding fragment) of the desired specificity.

Diagnostics to Identify Oncoimmunin Producing Cells

The compositions provided herein can also be used as diagnostics to particularly useful in screening tumor cells for production of Oncoimmunin factors. Such screening methods may serve to identify cells as being of tumor origin, identify tumor cell lines for hyper-production of Oncoimmunins, or assay production of Oncoimmunins in cell cultures. Screening clinical serum samples to determine the serum level of Oncoimmunin-L and Oncoimmunin-M will be useful not only for the detection of tumors, but also for prognosis evaluation after cancer therapy.

Using the compositions of the present invention one may detect Oncoimmunin proteins by any of several methods well known in the art including hybridization techniques for detecting the nucleic acid sequences encoding Oncoimmunins or immunoassays for detecting the Oncoimmunins themselves (Goding, et al., *Monoclonal Antibodies: Principles and Practice* (2d ed.) Academic Press, N.Y.; Harlow, et al., *Antibodies: A Laboratory Manual*, Cold Spring Harbor Laboratory Press, Cold Spring Harbor, N.Y. (1988); Ausubel et al., ed. Greene Publishing and Wiley-Interscience, New York (1987, and periodic updates)). For example, in an immunoassay for detecting or quantitating Oncoimmunin factors in a target sample, one would first combine the target sample with an anti-Oncoimmunin antibody. Then one would detect the binding between the antibody and the target sample by any of a number of means well known to those of skill in the art.

In detecting the presence of nucleic acid sequences having significant similarity to Oncoimmunin-encoding nucleic acids, one would employ any of several methods well known in the art, including Southern blots, Northern blots, plaque lifts, colony hybridization, or PCR or other amplification methods (Metzger, et al., *Nature* 334:31–36 (1988); Ausubel et al., ed. Greene Publishing and Wiley-Interscience, New York (1987, and periodic updates); U.S. Pat. Nos. 4,683,195; 4,683,202; *PCR Technology*, Erlich, ed., Stockton Press, New York (1989); *PCR Protocols: A Guide to Methods and Applications*, Innis et al. eds., Academic Press, San Diego (1990)).

The present invention also provides diagnostic kits for practicing the above described methods. Such kits generally comprise the above described antibodies and nucleic acids, and a label for detecting antibody binding or nucleic acid hybridization. Methods for using such kits are generally well known, and will generally be provided in an instruction manual for use of the kit. Such labels may include radiolabels, fluorescent labels, enzymatic labels, i.e., horseradish peroxidase (HRP), or the like. Further, such labels may be linked directly to the above antibodies or nucleic acids, or may be linked to a compound capable of binding said antibodies or nucleic acids (e.g., another antibody such as rabbit antigoat-HRP, sheep anti-mouse-HRP, or the like).

Screening for Therapeutic ex vivo Cultured Cells

Additionally, the Oncoimmunin factors (Oncoimmunin-L and Oncoimmunin-M) herein described are particularly useful in screening cells for potential cancer treatments. Various tumor masses and biopsies from organs with high lymphoid or myeloid content (e.g., bone marrow) can be treated with these Oncoimmunins, ex vivo, and the response in terms of proliferation or differentiation can be measured as herein described. Various ex vivo expanded cell cultures with different phenotype compositions can be screened to identify those giving a positive response to the Oncoimmunin treatment can then be effectively used in the treatment of cancer.

The following examples are offered to illustrate, but not to limit the present invention.

EXAMPLES

The following protocols and experimental details are referenced in the Examples that follow:

Materials

Dulbecco's modified Eagle's medium (DMEM) (4.5 g of glucose per liter) and Ham's F-12 medium were purchased from Flow Laboratories (Milano, Italy); AIM-V and RPMI 1640 media and fetal calf serum (FCS) were from GIBCO (Grand Island, N.Y., U.S.A.); insulin/transferrin/sodium selenite medium supplement was from Sigma (St. Louis, Mo., U.S.A.); human albumin (Albutein) was from Alpha Therapeutic (Los Angeles, Calif., U.S.A.); and [$^3$H]-thymidine (6.7 Ci/mmol; 1 Ci=37 GBq) was from New England Nuclear (Boston, Mass., U.S.A.). Recombinant human interleukins 4 and 6 (IL-4 and IL-6) and tumor necrosis factor $\alpha$ (TNF-$\alpha$) as well as neutralizing murine monoclonal antibody against human IL-6 (catalog 40028) were from Genzyme Transgenics Corporation (Framingham, Mass., U.S.A.); rabbit anti-human IL-2 IgG antibody (catalog 40012) was from Collaborative Research (Framingham, Mass., U.S.A.); recombinant human transforming growth factor $\beta$ (TGF-$\beta$) was from R and D Systems; and IL-2 came from Cetus Inc. (now Chiron, Inc. Emeryville, Calif. U.S.A.) and Genzyme Transgenics Corporation (Framingham, Mass., U.S.A.). Fluorescein and phycoerythrin labeled antibodies (anti-CD3, -CD4, and -CD8) were from Becton Dickinson (San Jose, Calif., U.S.A.). CD11b-PE and CD11c were also obtained from Becton Dickinson. Anti CD18-FITC and CD11a-FITC were obtained from Gentrak (Plymouth Meeting, Pa., USA) and Biosource (Camarillo, Calif., USA) respectively. Human L-LDH-M$_4$ and mouse anti-human L-LDH-M$_4$ antibodies were obtained from Sigma Chemical Corp. (St. Louis, Mo., U.S.A.).

The clone of A431 cells used in the following examples was from J. E. DeLarco and is also available from the American Type Culture Collection (Rockville, Md., U.S.A.). Dog smooth muscle cells were from T. Innerarity (Gladstone Foundation, University of California, San Francisco, Calif., U.S.A.), Madin-Darby canine kidney (MDBK) cells were from the FDA cell depository, but are also available from the American Type Culture Collection. The 618, 677, and 660 melanoma tumor lines were established from human melanoma tumors by culturing in RPMI 1640/10% human serum. Four T-lymphocyte cell lines, TIL 618, 641, 660 and 677, were established from four human melanoma tumors as described (Topalian et al., *J. Immunol. Meth.* 102:127–141 (1987)). The tumor derived TIL lines 618, 660, and 677 were all deposited according to the terms of the Budapest Treaty with the American Type Culture Collection (ATCC) of 12301 Parklawn Dr., Rockville, Md. USA on Feb. 4, 1994 and assigned Accession Nos.: CRL11545, CRL11546, and CRL11547 respectively.

Figure 4:
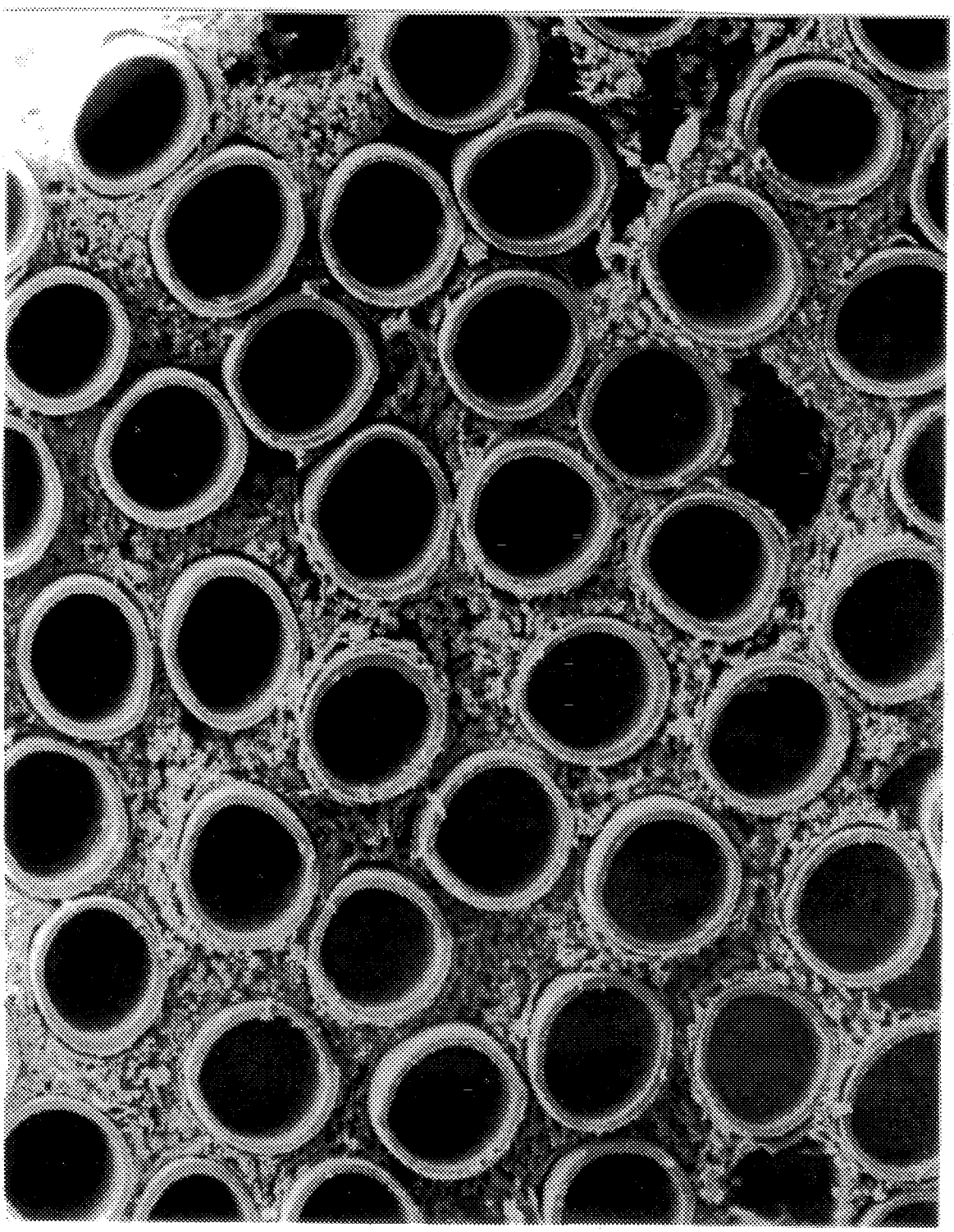
FIG. 4. Scanning electron micrograph (magnification 60x) of A431 cells grown in a hollow fiber bioreactor. Dark insides of hollow fibers that contain reservoir medium (DMEM/2% FCS) are separated from the extracapillary space containing media conditioned by A431 cells (designated extracapillary space media or ECSM), by a membrane with a 10 kDalton (kDa) cutoff.

A bioreactor with a cartridge containing hollow fibers having a molecular-weight cutoff of 10 kDa (Cellco Advanced Bioreactors, Kensington, Md., U.S.A.) was used for the large-scale culture of A431 cells. See FIG. 4 illustrating the hollow fiber with A431 cells growing in the extracapillary space.

ELISA kits for IL-2, IL-4, and IL-6 were from Genzyme (Framingham, Mass., U.S.A.) and a second ELISA kit for IL-2 was from Collaborative Research (Framingham, Mass., U.S.A.).

Q-Sepharose Fast Flow and Sephacryl S-300 resins and Mono-Q (HR 5/5) and Phenyl Superose (HR 5/5) FPLC columns were purchased from LKB-Pharmacia (Piscataway, N.J., U.S.A.). Precast SDS polyacrylamide (8–16% gradient and 12%) and isoelectric focusing (pH3–10) gels were bought from Novex (San Diego, Calif., U.S.A.). Molecular weight and IEF standards were obtained from Sigma Chemical Co. (St. Louis, Mo., U.S.A.) and BioRad (Hercules, Calif., U.S.A.). A C$_4$ reverse phase column (4.6×250 mm) was from SynChrom Inc (Lafayette, Ind., U.S.A.).

Human lymphocyte line, 660 TILs, were derived from a melanoma tumor patient number 660. HL-60, HEL, and K562 cell lines were obtained from the FDA cell repository and these cell lines are also available from the American Type Culture Collection. These three cell lines were derived from a human promyelocytic leukemic (HL-60), erythroleukemic (HEL), and chronic myelogenous leukemic patients (K562).

Cell Culture

All tumor lines (melanoma and A431) were carried in Dulbecco's modified Eagle's Medium (DMEM) 10% fetal calf serum (FCS). The four TIL lines were carried in AIM-V supplemented with IL-2 at 1000 units/milliliter (U/ml). The serum-free medium (SFM) used for proliferation assays was a modification of a serum-free medium used for melanoma cells (Packard, B. S., *Proc. Natl. Acad. Sci. USA*, 84:9015–9019 (1987)) with DMEM/Ham's F-12 at a 1:1 ratio substituting for DMEM alone. Optimum TIL culture may be achieved by utilizing culture plates in which each well contains 8 to 11 ml of medium. The well is preferably dimensioned so that the cross-sectional area of the open face of the well in cm$^2$ is equal to the volume of the medium in ml.

The bioreactor cartridge was seeded with $\approx 5 \times 10^3$ A431 cells in DMEM/10% FCS. After 3 weeks, the medium in the extracapillary space (ECSM) of the cartridge was switched to serum free medium (SFM) and the FCS concentration in the reservoir medium was lowered from 10% to 2%. The ECSM was drained daily from the cartridge, which was then filled with fresh SFM. The conditioned medium (ECSM) was then centrifuged, filtered (0.22 μm), and stored at 4° C.

Phenotyping

Staining was done at 4° C. for 30–60 min in Hank's balanced salt solution (HBSS) containing 10% (v/v) FCS and 0.02% (w/v) NaN$_3$. 0.5–1.0×10$^6$ cells were used per sample. Prior to the addition of fluorescently-labeled antibodies, 100 μg of human IgG was added to the cells. Flow microfluorometric analyses were performed using either a Coulter EPICS flow cytometer or a Becton-Dickinson FACScan instrument (Becton Dickinson, Mountain View, Calif., U.S.A.) in the absence of gates.

Cellular Proliferation Assays

Gama ray irradiated tumor cells at $5 \times 10^4$ cells per well were plated in 96-well flat-bottomed plates. Confluent cultures of tumor cells were gamma ray irradiated (3000 rads) (1 rad=0.01 Gy) just before cocultivation with TILs. Lymphocytes were removed from IL-2 containing AIM-V and placed in the appropriate medium for bioassay 48 hr before commencement of proliferation assays. They were resuspended in SFM or DMEM/10% FCS at $1.25 \times 10^5$ lymphocytes per ml for cocultivation experiments and at $6 \times 10^5$ lymphocytes per ml for experiments in which soluble factors were being assayed; 200 μl of cell suspension was added per well. Cellular proliferation was determined in the presence of conditioned media and cytokines at the indicated concentrations. For experiments in which neutralization by an antibody was being measured, conditioned media were preincubated with the antibody at concentrations up to 10-fold the labeled neutralization capacity for 2.5 hr at 37° C. before the addition of cells.

After 24-or 48-hr stimulation, the level of lymphocyte proliferation was assayed by adding 0.5 μCi of [$^3$H]-thymidine to each well of a 96-well plate for 4 or 18 hr. A Skatron harvester was used to harvest the cells, and the radioactivity was counted by using an LKB β-plate reader (Pharmacia LKB, Piscataway, N.J., U.S.A.). Each measurement was done in sextuplicate; each experiment was repeated at least three times.

The following assay conditions are critical in identifying the tumor-derived activities described.

1. Two days prior to performing the assay, T-cells must be removed from IL-2 containing medium and must be placed in serum-free medium. Use of cells after one or three days will not lead to successful detection of activity.

2. Optimization of mitogenic activity is at 24 hours after commencement of assay.

3. Under serum-free conditions, no other tumor-derived factor is capable of stimulating T-cell growth.

Thymidine incorporation assays for 660 TILs were performed. For hematopoietic lines i.e., HL-60, HEL, and K562, the cells were carried in RPMI with 10% fetal calf serum. Forty-eight hours prior to commencement of proliferation assays, cells were removed from serum-containing medium by washing twice in serum-free medium and culturing for this 48 hour interval in the serum-free medium. For proliferation assays the concentration of hematopoietic cells was $2.7 \times 10^5$ cells/ml.

Example 1

Growth Characteristics of TILs

Melanoma tumor cells (618 melanoma cells) were plated at $5 \times 10^4$ per 0.2 cm$^2$ in Dulbecco's modified Eagle's medium (DMEM)/10% fetal calf serum (FCS). After 1 day the medium was changed to serum-free medium (SFM) and left for at least 48 hr. Tumor infiltrating lymphocytes derived from the same tumor (618 TILs at $1 \times 10^6$ cells per ml) were plated without and with a confluent monolayer of 618 melanoma tumor cells. Twenty-four hours later the cultures were examined and photographed.

Figure 1B:
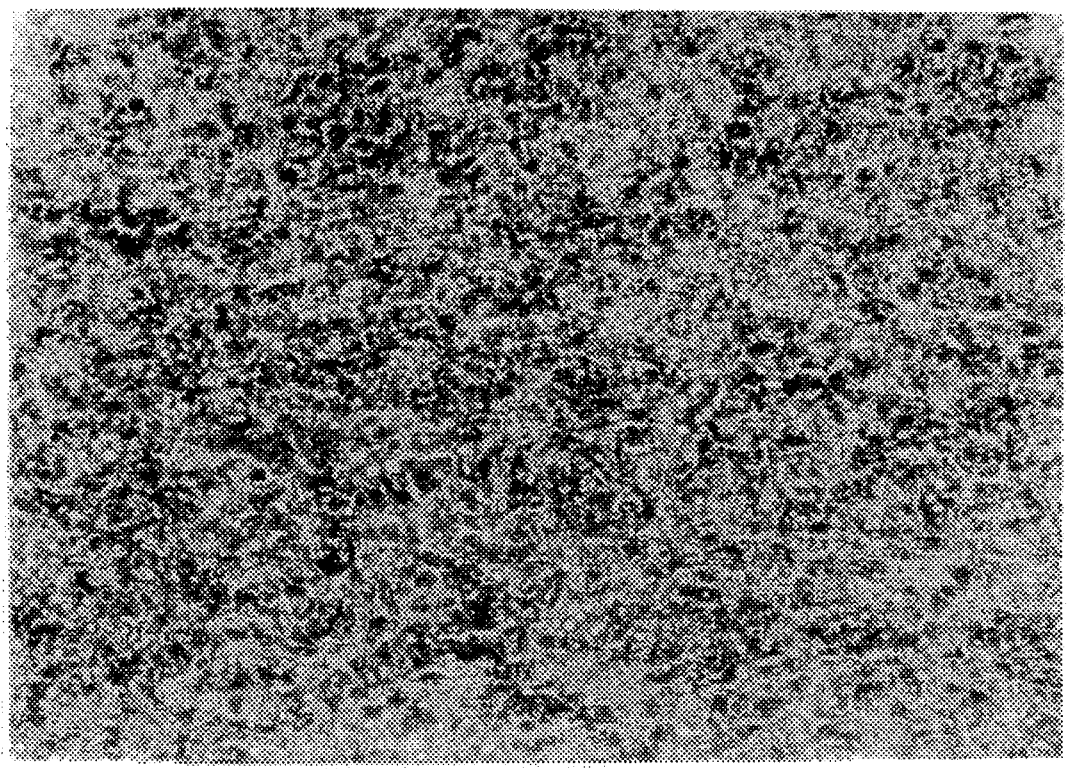

In the absence of 618 melanoma tumor cells (FIG. 1(a)), lymphocytes grow as large clusters in suspension, whereas in the presence of a monolayer of cell line 618 tumor cells, TILs have a spread appearance and grow in tight apposition to the tumor cells. The absence of large clusters of lymphocytes in the presence of 618 melanoma tumor cells (FIG. 1(b)) suggests that cellular heterophilia (i.e., adhesion between lymphocytes and tumor cells) predominates over cellular homophilia (i.e., adhesion among lymphocytes). Thus, tumor cells induced a striking change in the morphology of TIL-TIL interactions.

Although TILs 618, 660, and 677 could lyse autologous tumor cells that had been frozen but never cultured, they showed virtually no lytic capability against any of the cultured tumor lines in the configuration used in this study (i.e., as adherent monolayers). This sharply contrasts with lymphokine-activated killer cells, which effectively lysed all tumor lines used in this work. addressed.

To further investigate these tumor-induced morphological changes, the phenotypes of TILs were measured by tagging the TILs with labeled antibodies specific for cell surface markers (CD3, CD8, and CD4) and then counting the occurrence of each marker using a Becton Dickinson FACScan flow cytometer (Becton Dickinson, Mountain View, Calif., U.S.A.).

Table 1 shows the phenotypes of TILs measured in this manner. The table indicates the percentages of TILs derived from each cell line that show CD3, CD8, and CD4 cell surface markers respectively. The CD3 marker is diagnostic of T-cells and the high percentages observed (95–99%) indicate that the TILs derived from all four cell lines were virtually pure T-cell populations. CD8 is a marker for cytotoxic/suppressor T-cells and CD4 is a marker for helper/inducer T-cells. Thus TIL 677 and TIL 660 are virtually pure cytotoxic T-cell populations whereas TIL 618 is just a predominantly cytotoxic T-cell population. In contrast, the TIL 642 population showed a pure helper/inducer phenotype with about 20% of this population testing double positive for both CD8 and CD4 and therefore showing a mixed helper/inducer and cytotoxic/suppressor phenotype.

TABLE 1

| Phenotypes of TILs measured by flow cytometry | | | |
|---|---|---|---|
| TIL | CD3+ % | CD8+ % | CD4+ % |
| 618 | 97 | 83 | 12 |
| 677 | 99 | 93 | 3 |
| 641 | 97 | 19* | 95 |
| 660 | 98 | 88 | <3 |

*Nineteen percent of 641 TILs were double-positive for both CD8 and CD4; none was singly positive for CD8.

Example 2

TIL Proliferation

To determine whether the altered TIL growth morphology in response to tumor cells seen in Example 1 was a part of an immunostimulatory response, proliferation of four TIL lines was compared in the presence and absence of irradiated tumor cells. Specifically, the cellular proliferation rates of TIL lines derived from four patients (designated 618, 677, 641 and 660) were determined with and without a gamma irradiated tumor cell line established from patient 618. Because all four TIL lines had a culture history of IL-2 dependence, the initial set of experiments were performed both in the presence of IL-2 (1000 U/ml and 2 U/ml) as well as in its absence.

In the presence of IL-2 (1000 U/ml or 2 U/ml), the addition of irradiated 618 tumor cells to the culture did not significantly (by greater than 2 standard deviations) affect the proliferation, as measured by [$^3$H]-thymidine incorporation, of the four TIL lines tested. TIL 677 showed a barely significant increase (just equal to 2 standard deviations) in [$^3$H]-thymidine incorporation in the presence of IL-2 at 2 U/ml.

Figure 2A:
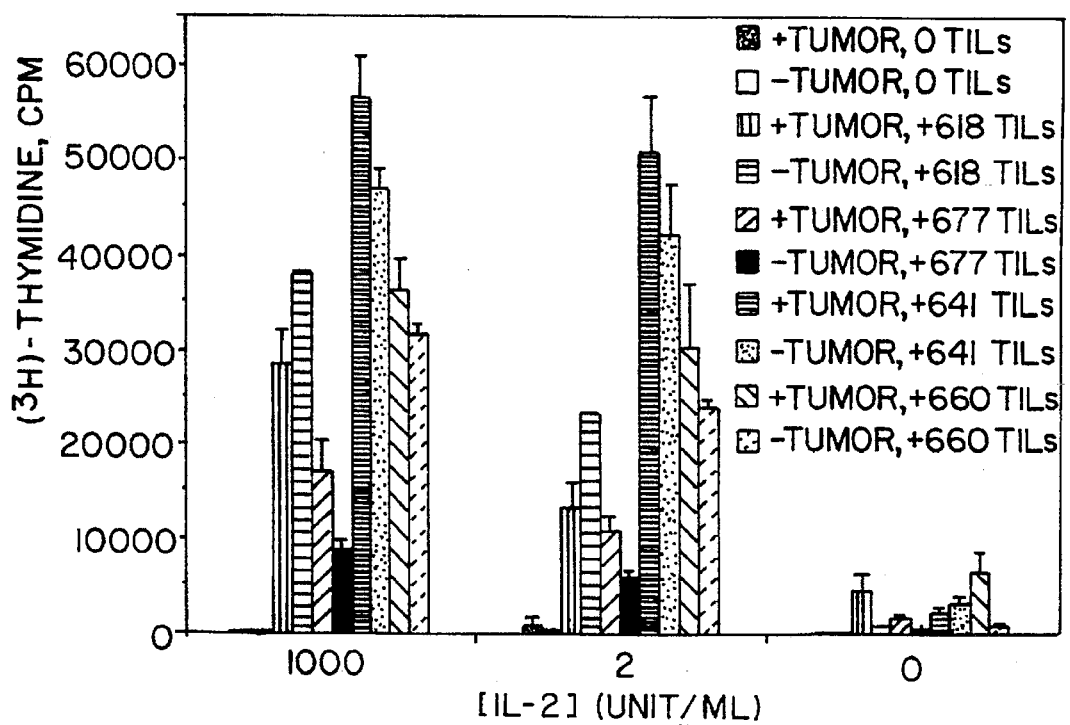
FIG. 2. (a) Effect of gamma ray irradiated 618 melanoma tumor cells on the proliferation of four TIL cell lines at three IL-2 concentrations: 1000 units/ml (U/ml), 2 U/ml and 0 U/ml. (b) Expansion of the right third of (a), proliferation in the absence of IL-2 (0 U/ml). The enhancement of TIL proliferation by the presence of irradiated tumor cells is detectable only in the absence of interleukin-2.
Figure 2B:
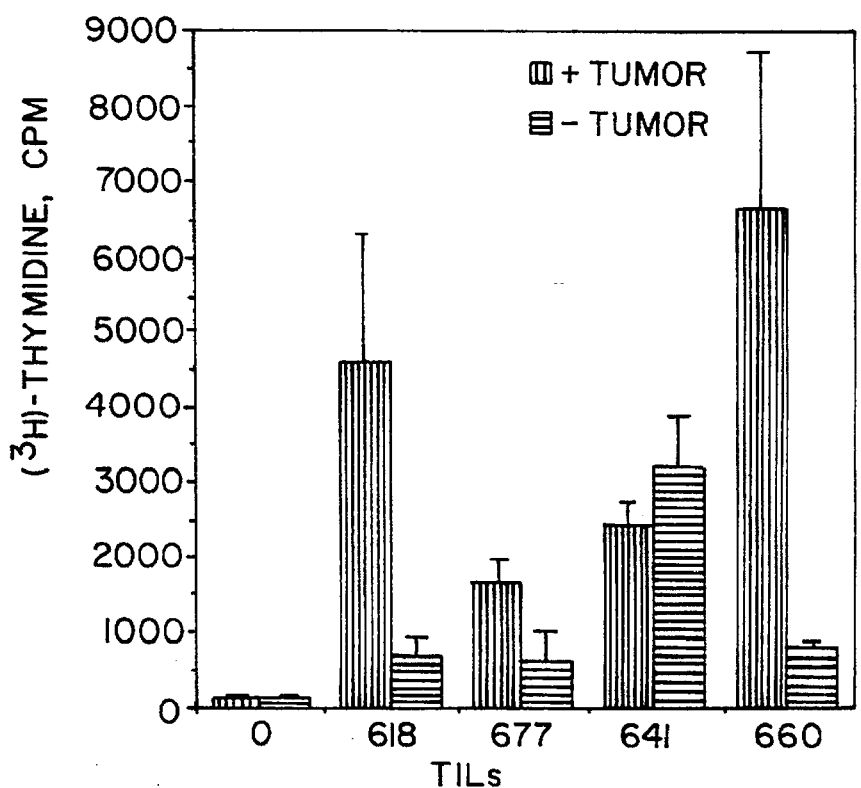

In contrast, the presence of irradiated 618 melanoma tumor cells dramatically increased proliferation of both 618 and 660 TIL cells (FIG. 2(b)). The response of the 677 TIL line was again marginally significant.

The presence of tumor cells had no effect on the proliferation of the 641 TILs, a cell line with a 100% CD4$^+$ phenotype. The three other TIL lines (618, 660, and 677) are composed of, at least, 80% CD8$^+$ cells. Hence, lymphocyte proliferation assays suggested the proliferative potentiation of melanoma tumor cells for CD8$^+$ lymphocytes in the absence of IL-2.

Thus, cultured tumor cells can support T-cell mitogenesis independently of IL-2. This fact may explain the observed differences in phenotypic profiles of TIL cultures at the state of reinfusion into patients with those of starting populations (Rosenberg, et al., *New Engl. J. Med.* 319:1676–1680 (1988); Packard, B. S. pp. 293–303 In: *Progress in Regional Cancer Therapy*. Jakcez, et al., eds., Springer, Heidelberg, (1990)). Because receptors for IL-2 are present on virtually all activated T-cells (Smith, K. A. *Adv. Immunol.*, 42:165–179 (1988)), the T-cell population that will grow ex vivo in the constant presence of this lymphokine is strongly biased toward those cells capable of transducing and using the IL-2 signal most efficiently. Hence, factors from the tumor environment, which may be essential for maintenance of lymphocytes with antitumor activity, may not be retained in long term cultures in which all tumor cells have died and the only exogenous cytokine is the pan T-cell mitogen IL-2.

Example 3

TIL Proliferation Potentiated by Tumors

To determine whether the observed mitogenic stimulation of TILs by irradiated tumor cells was induced by factors of tumor cell origin and not by factors present in the serum, proliferation assays were done in parallel, both in serum-free medium (SFM) and in serum containing medium (DMEM/10% FCS). The TILs were cultured in the presence of gamma ray irradiated A431 cells and proliferation was assayed by measuring the uptake of [$^3$H]-thymidine by the TILs as described above.

Figure 3A:
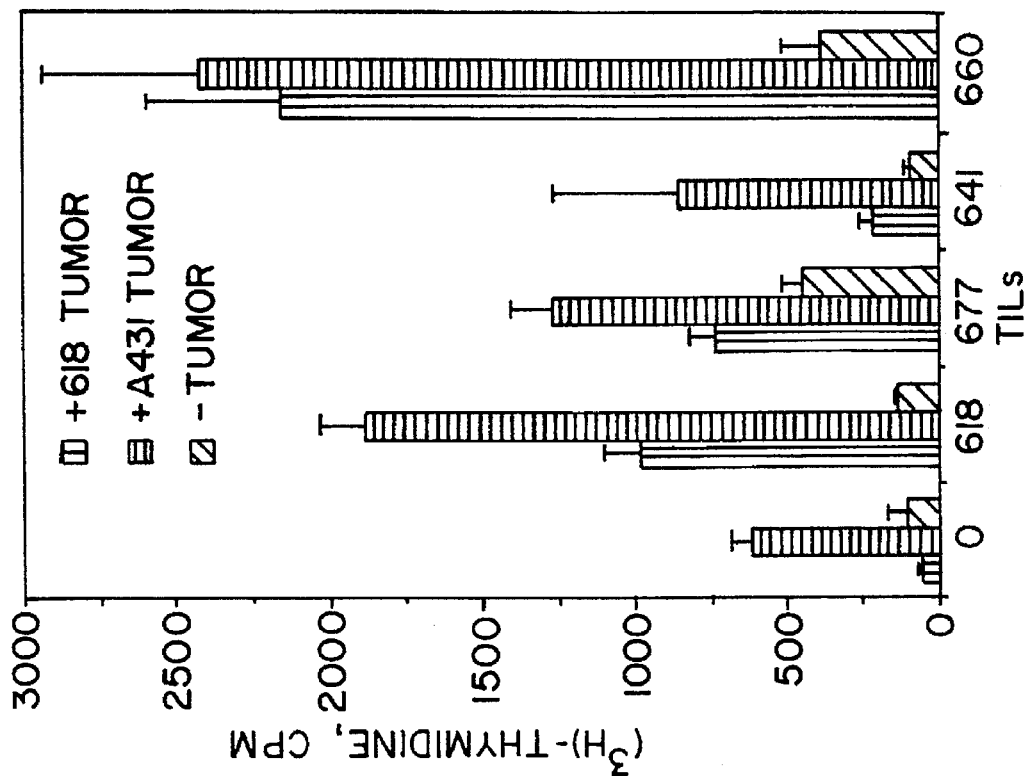
FIG. 3. Effect of serum on tumor-potentiated TIL proliferation. Comparison of enhanced TIL proliferation due to gamma ray irradiated 618 melanoma tumor cells with that from gamma ray irradiated A431 cells in (a) serum-containing and (b) serum-free media. A higher level of radioresistance of the A431 cells resulted in a higher background for the assays in serum-free media. The figures show no significant difference between the enhancement of TIL proliferation in the presence and in the absence of serum. Thus the factors responsible for the observed enhancement of TIL proliferation are derived from the gamma ray irradiated tumor cell lines and not the serum.
Figure 3B:
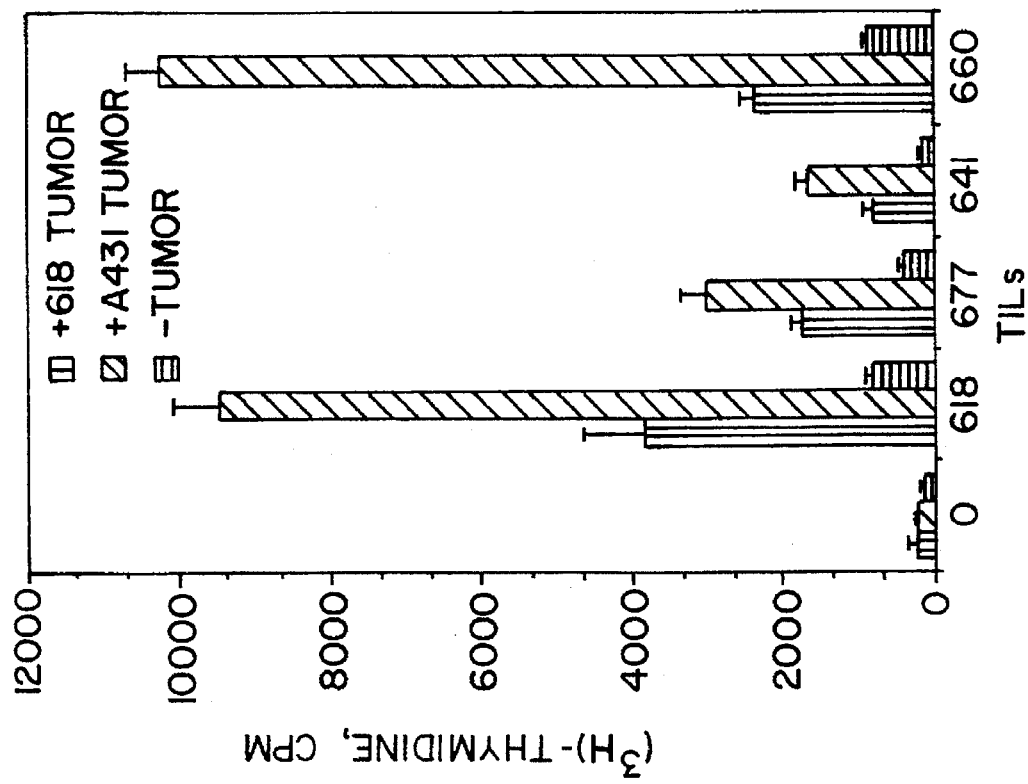

The proliferation levels of both 618 and 660 TILs were significantly increased by 618 tumor cells whether or not serum was present (FIG. 3). The proliferation of 677 TILs was marginally affected (i.e., by not greater than 2 standard deviations) in either medium. 641 TILs showed statistically insignificant changes upon addition of tumor cells. Hence, the results suggested that the enhancement of proliferation of TILs by 618 tumor cells was independent of serum-derived factors.

Example 4

Enhancement of TIL Proliferation

Proliferation of TIL 660, the TIL that showed the greatest proliferation in the presence of the irradiated 618 melanoma tumor cells, was measured in the presence of two additional melanoma tumor lines established from patients 660 and 677 respectively. TIL 660 cells showed a mitogenic response to 660 and 677 melanoma tumor cells similar to that seen with the 618 melanoma tumor cell line. As seen in Table 2, 660 TILs showed a three to fourfold increase in [$^3$H]-thymidine incorporation when cultured in the presence of 660 and 677 melanoma tumor cells. Thus, mitogenic T-cell stimulation by the melanoma tumor cell lines, all of which were derived from unrelated patients, is not major histocompatibility complex-restricted.

TABLE 2

| Proliferation of 660 TILs in SFM in the absence and presence of irradiated melanoma cells lines | |
|---|---|
| Tumor cell line | $^3$H-Thymidine cpm |
| None | 355 ± 54 |
| 618 | 1661 ± 57 |
| 677 | 1289 ± 52 |
| 660 | 1182 ± 154 |

Background counts for tumor alone have been subtracted.

Example 5

Potentiation Specificity

To determine whether tumor cell-induced lymphocyte mitogenicity is characteristic of tumors of a specific embryonic origin, such as the neural crest, which includes melanomas a well as neuroblastomas, a cell line derived from a tumor of epidermal carcinoma origin, the A431 line was used as a source of potentiation of TIL proliferation. Thus gamma-irradiated A431 cells were tested for their ability to potentiate TIL proliferation in both serum-containing and serum-free media.

Proliferation was assayed as an increase in [$^3$H]-thymidine incorporation by 618, 677, 641 and 660 TILs. Irradiated A431 cells potentiated proliferation of all four TIL lines in serum (FIG. 3(a)) and showed effects similar to 618 tumor cells in serum free medium (FIG. 3(b)). Thus, the tumor derived factors that induce proliferation are not specific to the melanoma tumor cells suggesting that tumor-induced immunocyte stimulation may be broadly prevalent.

Example 6

Transformed Cell Line Specificity

In contrast to the transformed melanoma and A431 cell lines tested, irradiated dog smooth muscle cells and MDBK cells, two untransformed cell lines, did not potentiate TIL proliferation (data not shown). This fact, along with stimulation by the murine melanoma B16 line, supports the concept of TIL stimulation by transformed cells, rather than normal cells.

Example 7

Testing of Soluble Factors for Mitogenic Activity

In order to both investigate the effect of concentration of conditioned medium on TIL proliferation, and ascertain the lower size limits of Oncoimmunin factors, [$^3$H]-thymidine incorporation by TILs was measured as a function of concentration of ECSM or reservoir medium from the fiber cartridge bioreactor.

A scanning electron micrograph shows A-431 cells in the hollow fiber cartridge in cross section (FIG. 4). Tumor cells were only seen in the space outside the hollow fibers. The membranes lining these fibers had a molecular mass cutoff of 10 kDa; hence, any factors secreted by the tumor cells with a molecular mass >10 kDa were retained in the ECSM. The medium that circulated inside the hollow fibers was composed of DMEM/2% FCS and was designated as the reservoir. The ECSM was drained daily and assayed for bioactivity.

Figure 5A:
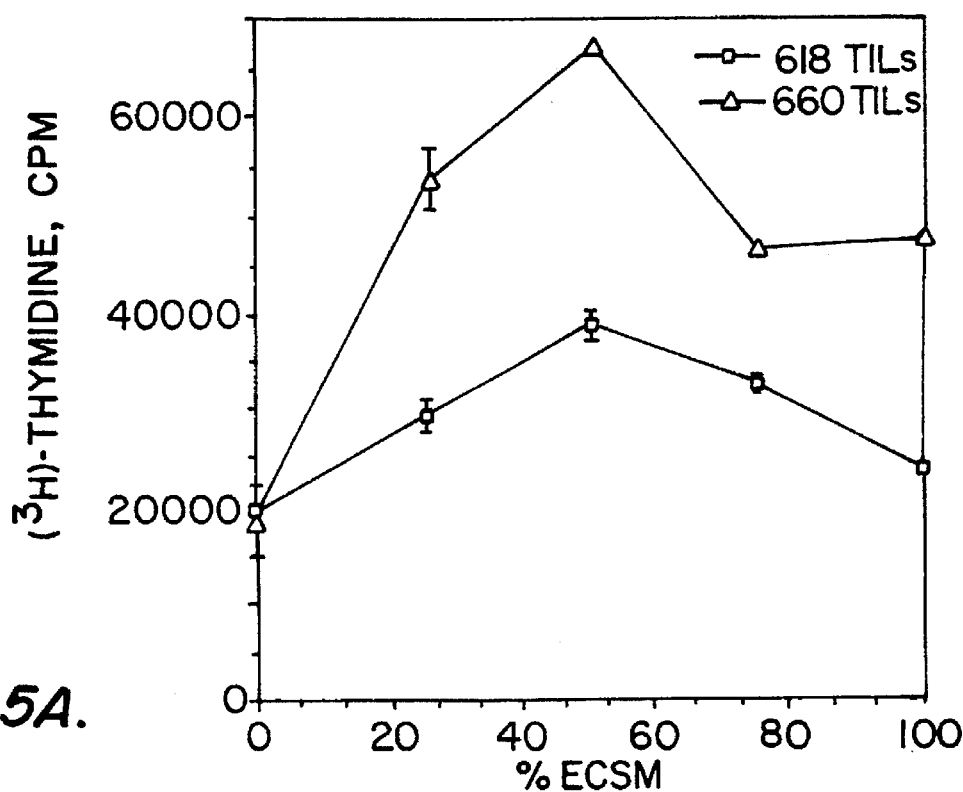
FIG. 5. TIL proliferation assays using media conditioned by A431 cells. (a) Serum-free conditioned medium from the bioreactor extracapillary space (ECSM). (b) Serum-containing medium from the bioreactor reservoir (dark insides of the hollow fibers shown in FIG. 4). Comparison of (a) and (b) indicates that the factors responsible for the observed mitogenic activity are detectable in the serum-free conditioned medium (ECSM) not in the reservoir medium.

The amounts of [$^3$H]-thymidine incorporation into both 618 and 660 TILs as a function of increasing concentrations of ECSM are plotted in FIG. 5(a). There is a dose-dependent increase in proliferative activity up to the assay composition of 50% ECSM for both 618 and 660 TILs. Above this level both curves fall off. These declines may be due to the absence of nutrients in the spent ECSM or the presence of the inhibitory factor(s). Additionally, these curves may also represent behavior similar to that of other known mitogens for which, at high concentrations, proliferative levels are submaximal. In support of the latter hypothesis, when partially purified material was used as the stimulus, the dose-response curve was U-shaped with the maximum observed at ≈1 mg of protein per ml (data not shown).

Figure 5B:
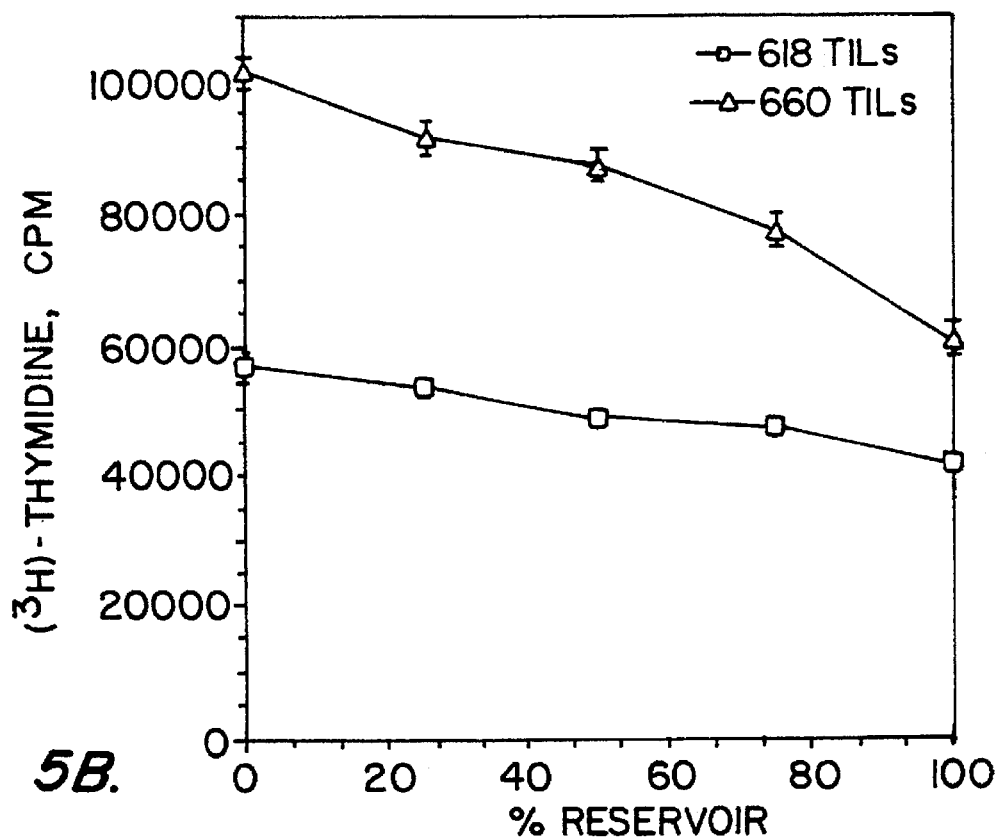

FIG. 5(b) shows the amount of [$^3$H]-thymidine incorporation into both 618 and 660 TILs as a function of increasing concentrations of reservoir medium. No stimulatory activity was detectable. Thus, molecular mass of the mitogenic factor(s) must be at least 10 kDa as no mitogenic activity was associated with factor(s) secreted into the reservoir.

Example 8

T-Cell Proliferation was not Caused by Known Mitogens

To determine whether the mitogenic activity present in ECSM was due to factors that have previously been shown to have direct mitogenic activity for T-cells, three ECSM samples collected at 2-week intervals were tested for IL-2, IL-4, and IL-6 by ELISA.

The presence of neither IL-2 nor IL-4 was measurable at or above detection levels for these two lymphokines (0.4 U/ml and 90 pg/ml, respectively). At these two respective concentration levels no significant proliferative activity above background was detected. However, IL-6 was found to be present at 2 ng/ml. This is consistent with other studies showing the presence of IL-6 in A431 cell supernatants (Kimbauer, et al., *J. Immunol.*, 142:1922–1928 (1989)).

To ascertain whether IL-6 could be a mitogen for TILs under the conditions used in this study, [$^3$H]-thymidine incorporation was measured after culturing 660 TILs for 24 hr in the presence of IL-6 at concentrations ranging from 0.01 to 20 ng/ml. At these concentrations, no [$^3$H]-thymidine incorporation above background was measured. Furthermore, the presence of a neutralizing monoclonal antibody against IL-6 had no effect on the stimulation of [$^3$H]-thymidine incorporation induced by ECSM, whereas mitogenic stimulation by IL-2 standards up to 100 U/ml was completely inhibited by the anti-IL-2 antibody used.

A lack of mitogenic activity for 660 TILs was also seen for TGF-B ($1\times10^{-7,-8,-9,-10,-11, \text{ and } -12}$ M) and TNF-α (1, 10, and 100 ng/ml). In all experiments IL-2 and ECSM served as positive controls. The absence of IL-2 and IL-4 in the ESCM, as determined by ELISA, and the lack of proliferative stimuli from IL-6, TNF-a, and TGF-B under the experimental conditions used suggest the presence of a direct T-cell mitogen not previously characterized.

Example 9

Purification of Oncoimmunin-M and Oncoimmunin-L

A) Purification of Oncoimmunin-M

Serum-free conditioned medium from A431 cells which were grown in a bioreactor was diluted 10-fold with 5 mM potassium phosphate buffer, pH 7.5. This material was loaded onto an ion exchange column (Q-Sepharose Fast Flow column 4.5×17 cm, Pharmacia LKB, Piscataway, N.J., U.S.A.) which had been equilibrated with a 15 mM potassium phosphate buffer, pH 7.5. The sample volume ranged from two to four liters. The column was then washed with 1 liter of 15 mM phosphate buffer, pH 7.5, after the sample loading was completed. This was followed by elution with (i) 400 ml of a 15 mM phosphate buffer containing 35 mM sodium chloride; then (ii) gradient elution with sodium chloride starting with 35 mM and ending with 200 mM sodium chloride, in 15 mM potassium phosphate buffer. Fractions of 150 drops each were collected throughout the gradient.

Figure 8A:
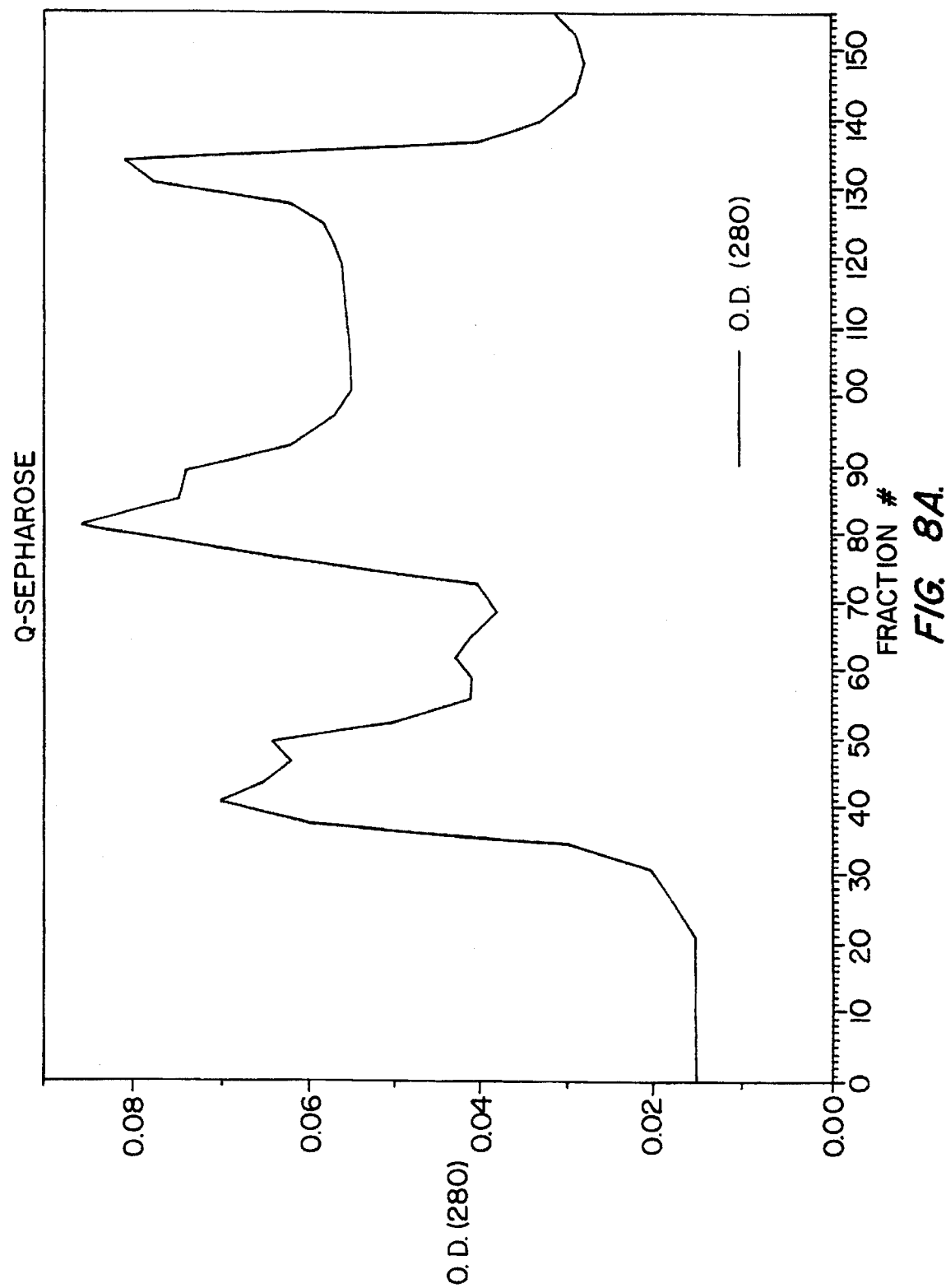
FIG. 8(A). Protein elution profile from ion exchange chromatography, using a Q-Sepharose column, of the serum-free conditioned medium. Protein elution is measured as absorbance at 280 nanometers (nm).
Figure 8B:
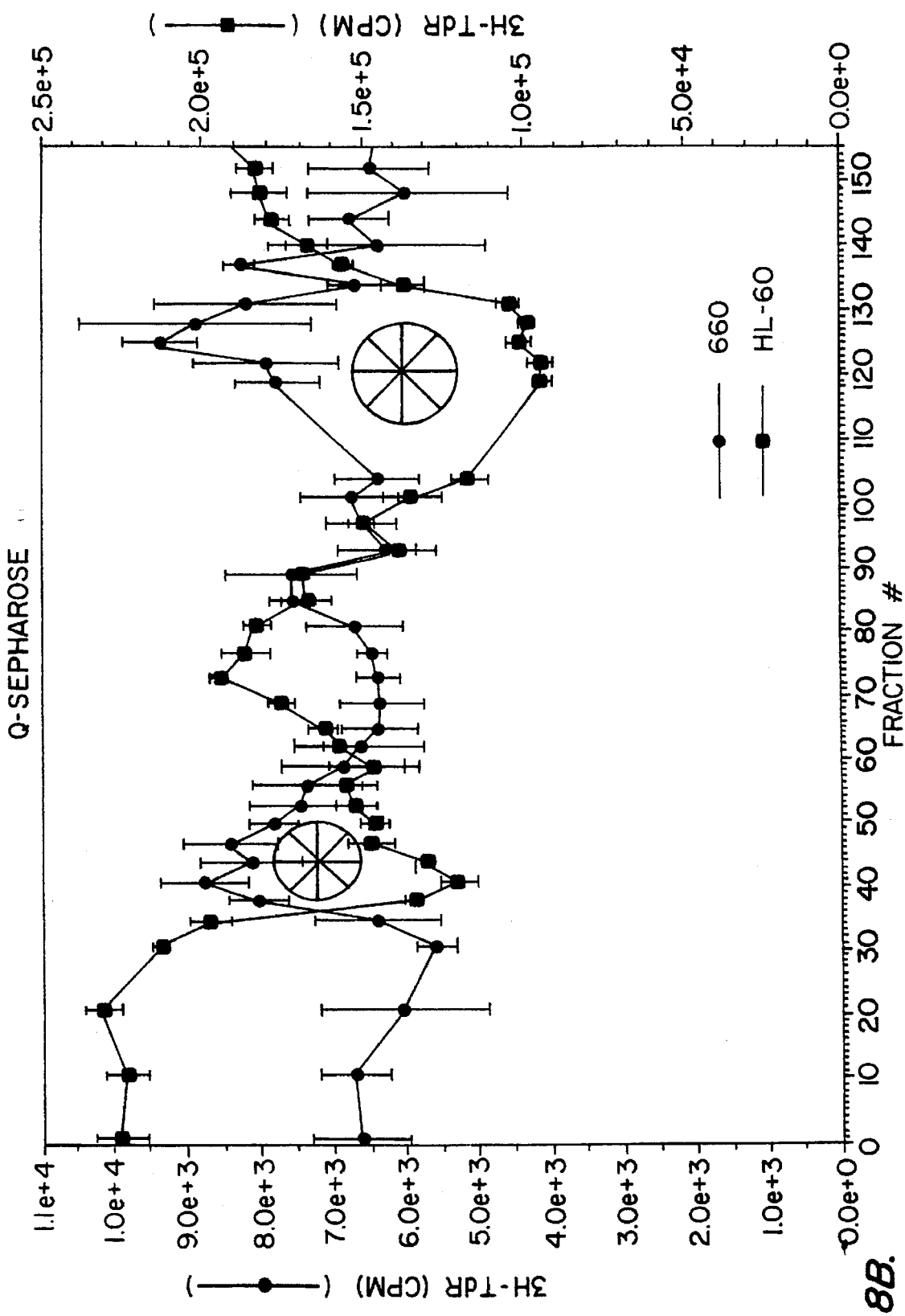
FIG. 8(B). Biological activities of fractions obtained from ion exchange chromatography of the serum-free conditioned medium. Two domains of bioactivity (indicated by the wheel symbol) were observed in fractions from Q-Sepharose chromatography. Oncoimmunin-M activity, present in the first domain ("early-eluting" fractions 30–60), was indicated by a decrease in [$^3$H]-thymidine incorporation in HL-60 myeloid cells. Oncoimmunin-L activity, present in the second domain ("late-eluting" fractions ca. 110–135), was indicated by an increase in [$^3$H]-thymidine incorporation by 660 TILs.
Figure 9:
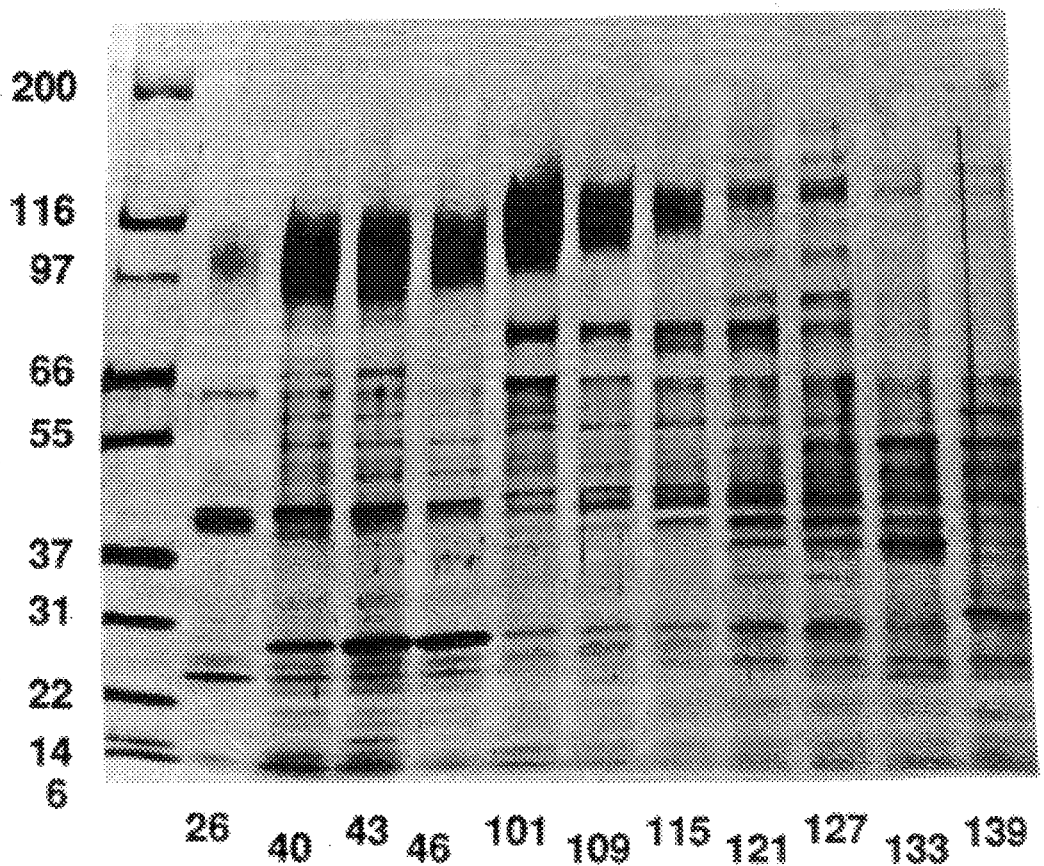
FIG. 9. SDS-PAGE analysis (using an 8% to 16% gradient gel) of the early and late eluting fractions from the ion exchange (Q-Sepharose) chromatography of the serum-free conditioned medium. The gel was stained using the Daiichi-II silver stain kit (Integrated Separation Systems, Framingham, Mass., U.S.A.).

FIG. 8(A) and FIG. 8(B) show the elution in terms of protein concentration (absorption at 280 nanometers (nm)) and in terms of bioactivity respectively. In bioassays performed on fractions 1 through 200, the eluted material was diluted 7.5-fold. The bioactivity elution profile shows two bioactive domains. FIG. 9 shows the protein composition analysis by a silver stained SDS-PAGE of the fractions from the two domains.

A first bioactive domain eluted at about fractions 30 through 60, and was designated the Oncoimmunin-M domain, or the early eluting Q-Sepharose peak. This first domain was also denoted the soluble EGF receptor domain, since the other protein present in this domain, in addition to Oncoimmunin-M, was the soluble epidermal growth factor (EGF) receptor protein with a molecular weight of about 110 kDa as confirmed by Western blotting, EGF binding, and amino acid sequence analysis. The Q-Sepharose purification step provided a 12 fold degree of purification (See Table 3).

A second bioactive domain eluted at about fractions 110–135, and was designated the Oncoimmunin-L domain, or the late eluting Q-Sepharose peak. This material was further purified as described in section B, below.

Active fractions from the Oncoimmunin-M (EGF receptor) domain from the Q-Sepharose column were pooled and placed in a Filtron filter unit with a cutoff of 10 kDa for concentration and equilibration into buffer A (50 mM phosphate, pH7 plus 1.7 M ammonium sulfate).

Figure 10:
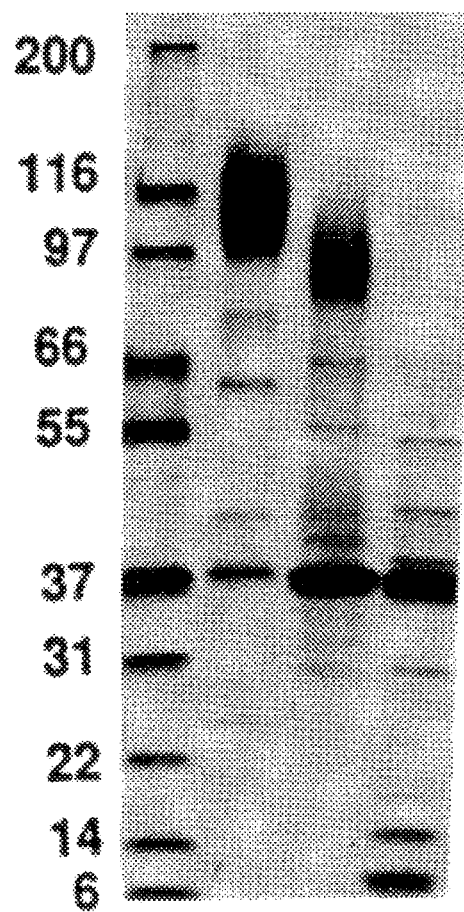
FIG. 10. SDS-PAGE analysis of fractions obtained from hydrophobic interaction chromatography performed on the pooled Oncoimmunin-M containing fractions obtained from ion exchange chromatography illustrated in FIG. 8B. Active fractions from the early eluting EGF receptor domain (showing Oncoimmunin-M activity) from the Q-Sepharose column were pooled and placed in a Filtron filter unit with a cutoff of 10 KDa for concentration and equilibration into buffer A (50 mM phosphate, pH7 plus 1.7 M ammonium sulfate). The equilibrated pool was loaded onto a phenyl superose FPLC column and washed with equilibration buffer A. The column elution was carried out using a step gradient consisting of 35%, 40%, and 100% (v/v) buffer B (50 mM phosphate, pH 7). Lane 1 shows molecular weight standards, while lanes 2, 3 and 4 show fractions eluted in 35%, 40% and 100% buffer B respectively. This 8% to 16% gradient gel was developed with the Daiichi-II silver stain kit.

The equilibrated pool was loaded onto a hydrophobic interaction chromatography column (Phenyl Superose FPLC column, Pharmacia LKB, Piscataway, N.J., U.S.A.) and washed with equilibration buffer A. The column elution was carried out by a series of step gradients (35%, 40%, and 100%) of buffer B (50 mM phosphate, pH 7). Protein compositions of the step gradient elution fractions of 35% B, 40% B and 100% B are shown in FIG. 10. The soluble EGF receptor with molecular mass of about 100 kDa, is removed from the step gradient elution in fractions from 0% to 40% buffer B.

Figure 11:
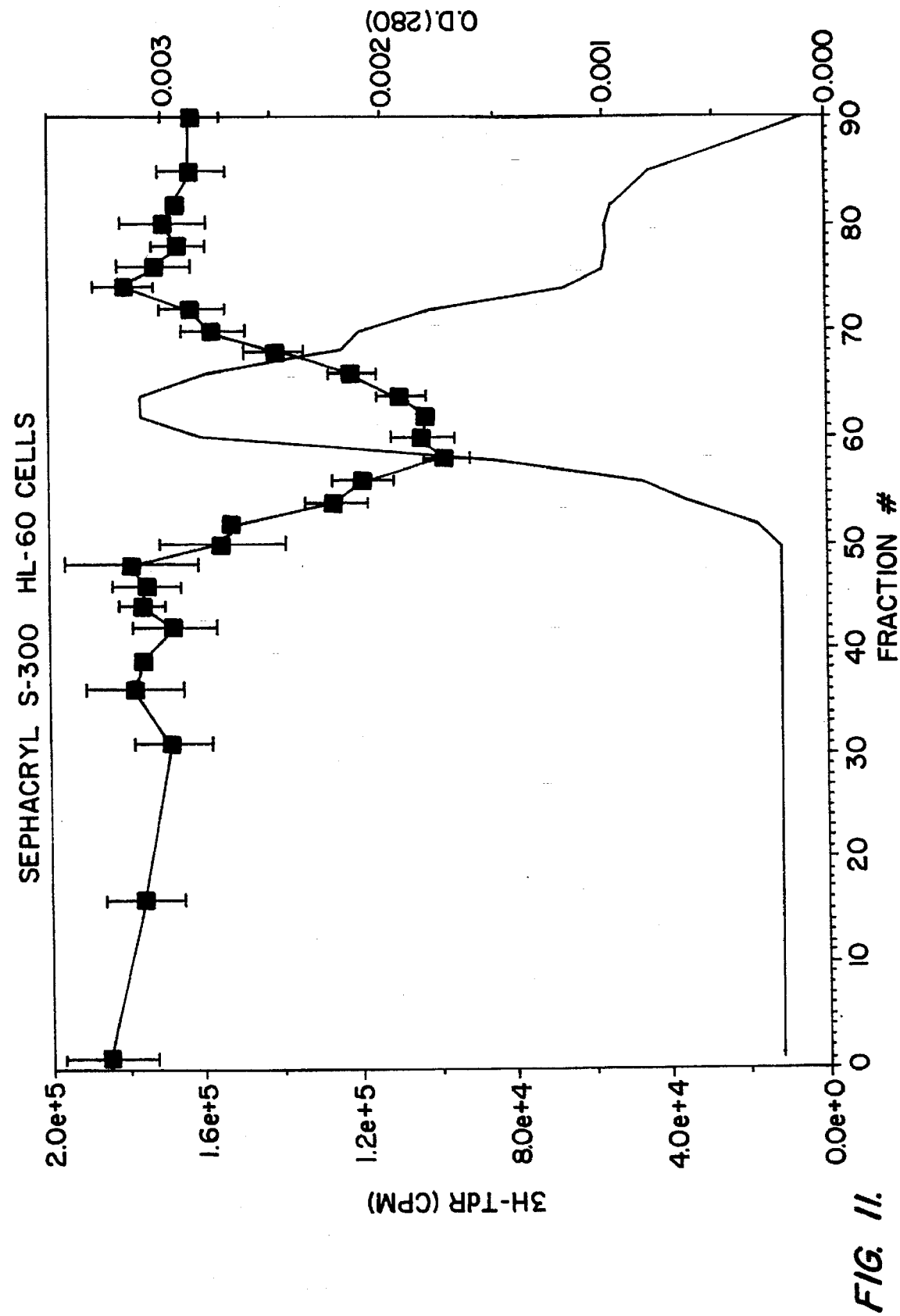
FIG. 11. Biological activity (closed squares) of fractions obtained by gel filtration (Sephacryl S-300) chromatography of Oncoimmunin-M containing fractions obtained from hydrophobic interaction chromatography described in FIG. 10. Biological activity was measured as the inhibition of $[^3H]$-thymidine incorporation into HL-60 cells. Material from the 100% B step of the Phenyl Superose column was loaded onto a Sephacryl S-300 column (2.5×100 cm). Elution was carried out using a 15 mM phosphate buffer, pH 7.4. Fractions of 85 drops were assayed after a 1 to 7.5-fold dilution. Protein concentration, measured as absorbance at 280 nm, is plotted on the same graph (solid line).
Figure 12:
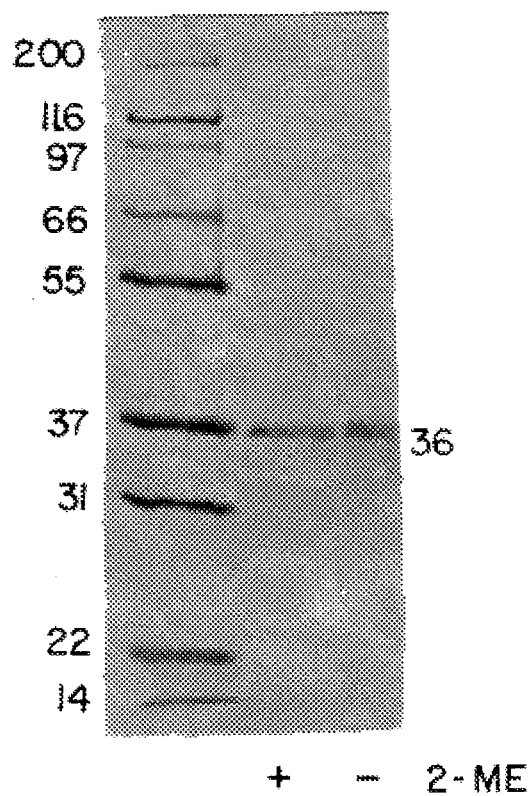
FIG. 12. SDS-PAGE of fractions from the gel filtration described in FIG. 11 showing the highest bioactivity (fractions 59–61 in FIG. 11) as measured by the inhibition of $[^3H]$-thymidine incorporation into HL-60 cells. The left lane provides molecular weight standards as indicated in the left margin. In the middle and right lanes, the samples were analyzed under reducing and non-reducing conditions respectively. The bioactive material runs at an approximate molecular weight of 36 kDa under both reducing and nonreducing conditions. The narrow bands at 36 kDa on this silver-stained gel indicate a protein (Oncoimmunin-M) purified to homogeneity.

The material from the 100% B step of the hydrophobic interaction chromatography was pooled and loaded onto a gel filtration column (Sephacryl S-300 column, 2.5×100 cm, Pharmacia LKB, Piscataway, N.J., U.S.A.). Elution was carried out using a 15 mM phosphate buffer, pH 7.4. Fractions of 85 drops were assayed after a 1 to 7.5-fold dilution. FIG. 11 shows the protein profile (solid line) and the biological activity profile (closed squares) of the fractions. FIG. 12 shows the SDS-PAGE analysis of the Sephacryl S-300 chromatographed fractions that exhibited maximal bioactivity (fractions 59–61 in FIG. 11). The single bands migrating with molecular mass of 36 kDa in the middle and right lanes are the purified Oncoimmunin-M electrophoresed under reducing and non-reducing conditions respectively. The single band in lanes 2 and 3 indicates that the protein has been purified to homogeneity and that the protein is not a disulfide bonded oligomer. This purification represents a 5000 fold increase in the purity of Oncoimmunin-M (See Table 3).

In vitro data indicate this factor's ability to inhibit growth and induce differentiation of myeloid leukemic cell line HL-60. This factor may be useful in treating bone and bone marrow dysfunctions. It may be useful alone or in combination with other colony stimulating factors and interleukins. In addition, because Oncoimmunin-M induces myeloid cell differentiation, it can be used to reduce secondary malignancy due to long-term treatment with carcinogenic chemotherapeutic agents.

TABLE 3

Degree of purification of Oncoimmunin-M obtained at each stage of the purification. Data are provided showing the loading volume, total protein loaded, specific activity ($EC_{50}$), protein yield and degree of purification for each purification stage. $EC_{50}$ was calculated as the amount of material required to provide 50% of the maximum biological activity (inhibition of [$^3$H]-thymidine incorporation by HL-60 cells) inducible by the material at the given stage of purification.

| Purification Stage | Loading volume ml | Total protein loaded mg | $EC_{50}$ | Protein Yield mg | Purif. fold |
| --- | --- | --- | --- | --- | --- |
| ECSM | 200 | 120 | 24 | | |
| Q-Sepharose | 2000 | 120 | 2 | 46.6 | 12 |
| Phenyl-Superose | 45 | 46.6 | ND[a] | ND | ND |
| Sephacryl S-300 | 5 | 1.8 | 4.8 | 0.036 | 5000 |

[a]ND, not determined.

B) Purification of Oncoimmunin-L

Serum-free conditioned medium from A431 cells which were grown in a bioreactor was diluted 10-fold with 5 mM potassium phosphate buffer, pH 7.5. This material was loaded onto an ion exchange column (Q-Sepharose) and eluted as described above. The Q-Sepharose step provided a 7.4 fold purification (see Table 4).

Figure 13:
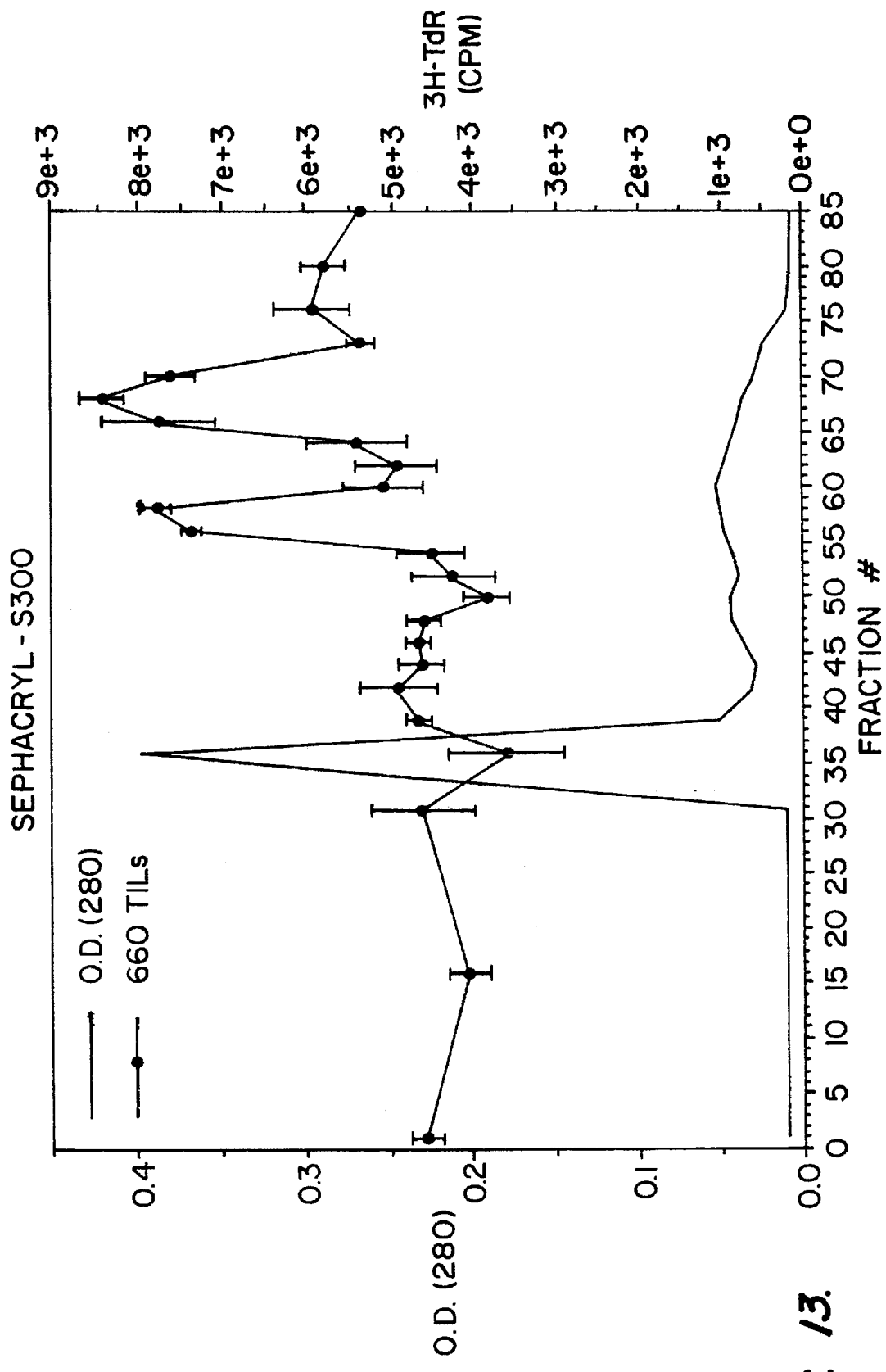
FIG. 13. Biological activity of fractions obtained by gel filtration (using a Sephacryl S-300 column) of the late-eluting (Oncoimmunin-L containing) fractions from Q-Sepharose chromatography of the serum-free conditioned medium. Fractions from the second bioactive domain of the Q-Sepharose column (Oncoimmunin-L) were pooled, concentrated in a Filtron filter unit, and then loaded onto a Sephacryl S-300 (2.5×100 cm) column. Elution was performed with a 15 mM phosphate buffer, pH 7.4. Biological activity was measured as the stimulation of $[^3H]$-thymidine incorporation into 660 TILs. Two bioactive domains appeared: fractions 49–61 and 63–71. Protein concentration, measured as absorbance at 280 nm, is plotted on the same graph.

Fractions from the second bioactive (Oncoimmunin-L) domain of the Q-Sepharose column (fractions 110–135 in FIG. 8B) were pooled, concentrated in a Filtron filter unit, and then loaded onto a gel filtration column (Sephacryl S-300, 2.5× 100 cm, Pharmacia LKB, Piscataway, N.J., U.S.A.). Elution was performed with a 15 mM phosphate buffer, pH 7.4. The elution profile of the gel filtration column is shown in FIG. 13. The purification through the gel filtration step resulted in a 38.6 fold increase in the purity of Oncoimmunin-L (see Table 4).

Figure 14:
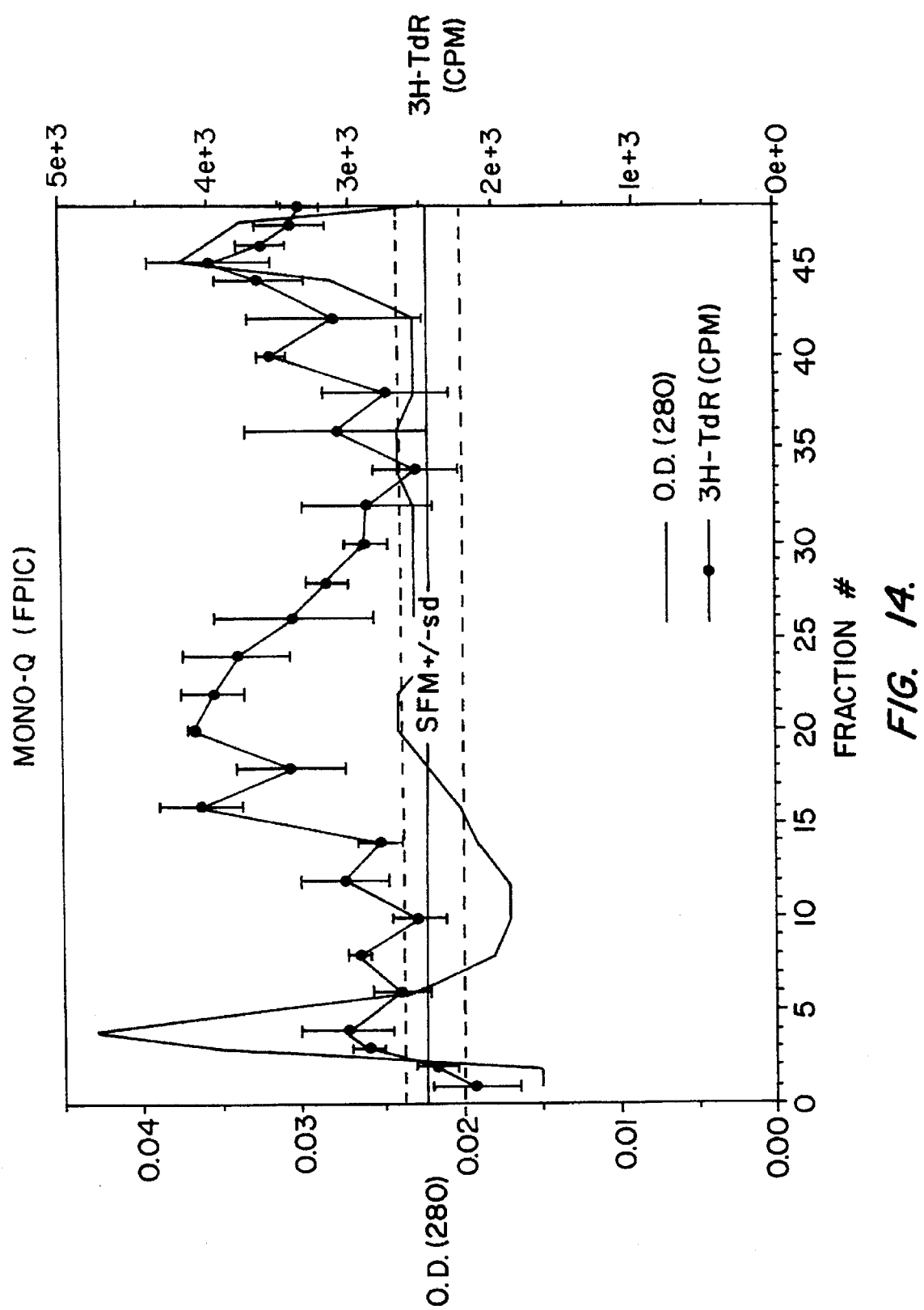
FIG. 14. Biological activity of fractions obtained by anion exchange chromatography of fractions 63 through 71 obtained from the gel filtration step described in FIG. 13. Active fractions 63 through 71 from the gel filtration chromatography were pooled, concentrated with a Filtron filter unit, equilibrated in a 25 mM Tris buffer, pH 7.5, and loaded onto a Mono-Q column. Elution was performed with a gradient using 25 mM Tris, pH 7.48 plus 0.50 M sodium chloride. Protein concentration, measured as absorbance at 280 nm, is plotted on the same graph.

Active fractions (fractions 63–71 in FIG. 13) were concentrated, equilibrated in a 25 mM Tris buffer, pH 7.58, and loaded onto an anion exchange column (Mono-Q, Pharmacia LKB, Piscataway, N.J., U.S.A.). Elution was performed with a gradient using 25 mM Tris, pH 7.48, plus 0.50 M sodium chloride. An elution profile is shown in FIG. 14. The purification through the gel filtration step resulted in a 771 fold increase in the purity of Oncoimmunin-L (see Table 4).

Figure 15A:
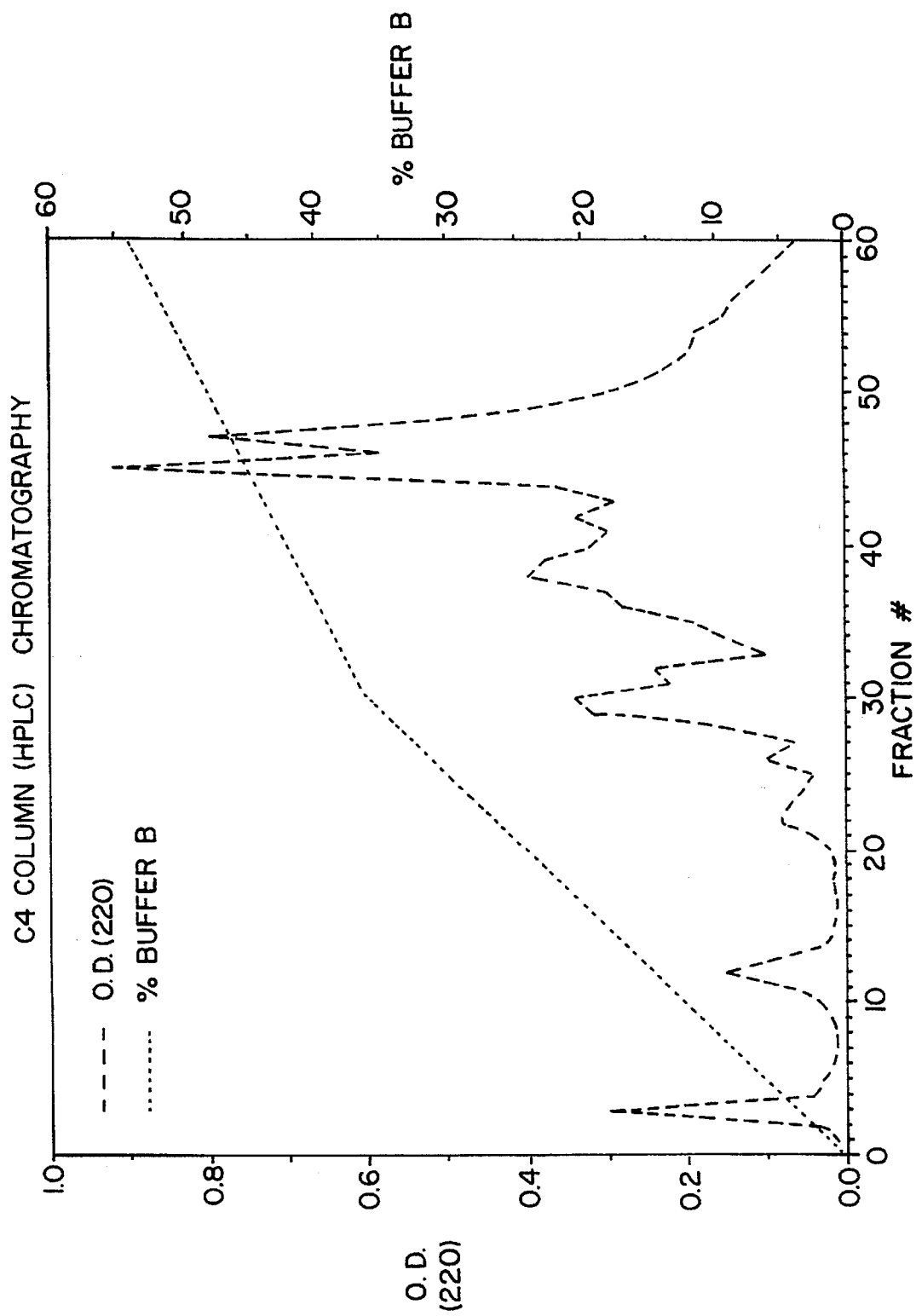
FIG. 15A. Protein elution profile of material obtained from reverse phase high performance liquid chromatography (HPLC) of the active fractions (fractions 19 to 23) obtained from the anion exchange chromatography step described in FIG. 14. A $C_4$ reverse phase HPLC column was equilibrated with water containing 0.05% trifluoroacetic acid (TFA). Elution was performed with an increasing gradient of buffer B (acetonitrile containing 0.05% TFA). With a flow rate of 1 ml/minute throughout the following gradient was run: at time(t)=0 minute, 0%B; at t=30, 36%B; at t=70, 60%B; at t=80, 90%B. All segments of the gradient were linear. The elution profile (absorbance at 220 nm) is shown by the dashed line, while the acetonitrile gradient is indicated by the dotted line. The fractions containing bioactive material (fractions 49 through 51) are indicated by a solid bar. While Oncoimmunin-L elutes maximally at fraction 47, the Oncoimmunin-L containing fractions were selected from the "back side" of the peak to avoid possible contamination with materials eluting in the peak at fraction 45.

Active fractions from the Mono-Q column (fractions 19 through 23 in FIG. 14) were injected onto a $C_4$ reverse phase HPLC column equilibrated with water containing a 0.05% trifluoroacetic acid (TFA). Elution was performed with an increasing gradient of acetonitrile containing 0.05% TFA. With a flow rate of 1 ml/minute throughout the following gradient was run: at time (t)=0 minute, 0%; at t=30, 36%; at t=70, 60%; at t=80, 90% acetonitrile/TFA. All segments of the gradient were linear. An elution profile from the reverse phase HPLC is shown in FIG. 15A. The purification through the reverse phase HPLC step resulted in a 6842 fold increase in the purity of Oncoimmunin-L (see Table 4).

Figure 15B:
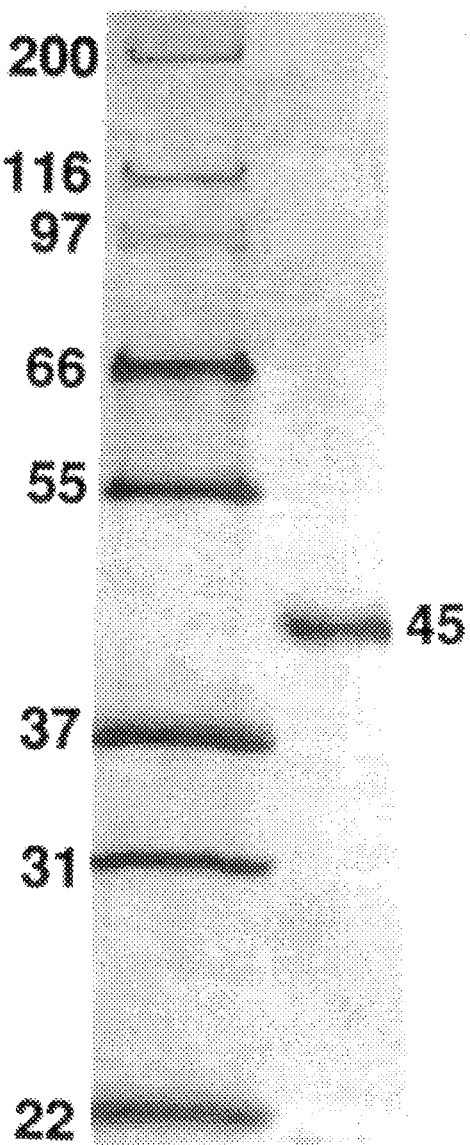
FIG. 15B. SDS-PAGE (12%) gel of the pooled fractions 49 through 51 obtained from the reverse phase high performance liquid chromatography (HPLC) described in FIG. 15A. The purified material (Oncoimmunin-L) has an approximate molecular weight of 45 KDa as seen in the silver stained SDS-PAGE gel.
Figure 16:
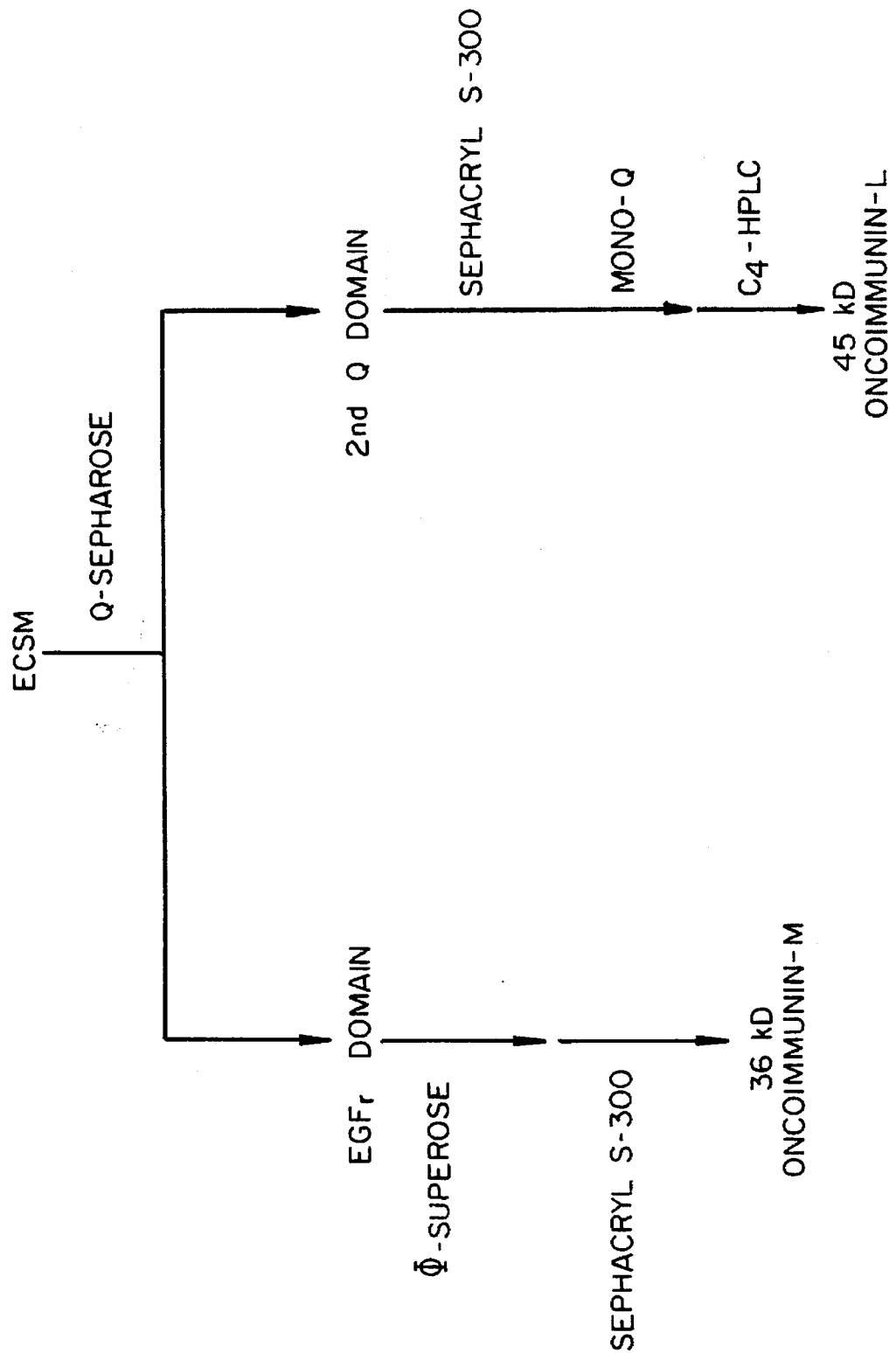
FIG. 16. Purification Flowchart. The general purification methods described herein for use in obtaining Oncoimmunin-L and Oncoimmunin-M of the present invention are shown.

The bioactive fractions (indicated by a solid bar over fractions 48 to 51 in FIG. 15A) were pooled. This purified Oncoimmunin-L was electrophoresed on a 12% acrylamide gel which was developed by silver stain. The gel showed a single band migrating with the apparent molecular mass of 45 kDa (FIG. 15B) indicating that Oncoimmunin-L was purified to homogeneity.

In vitro data which show this factor to be a T-cell mitogen, and also show it is useful as an immunotherapeutic agent. Specifically, it allows ex vivo expansion of T-cells with retention of biologic characteristics for therapeutic usage. In addition, administration of this factor to patients may enhance immunologic response and maintenance of immunosurveillance of patients.

TABLE 4

Degree of purification of Oncoimmunin-L obtained at each stage of the purification. Data are provided showing the loading volume, total protein loaded, specific activity ($EC_{50}$), protein yield and degree of purification for each purification stage. $EC_{50}$ was calculated as the amount of material required to provide 50% of the maximum biological activity (induction of T-cell mitogenesis) inducible by the material at the given stage of purification.

| Purification Stage | Loading volume ml | Total protein loaded mg | $EC_{50}$ | Protein Yield mg | Purif. fold |
| --- | --- | --- | --- | --- | --- |
| ECSM | 200 | 168 | 650 | — | |
| Q-Sepharose | 2000 | 168 | 125 | 8.6 | 7.4 |
| Sephacryl S-300 | 5 | 8.6 | 33.3 | 0.740 | 38.6 |
| Mono-Q | 35 | 0.740 | 1.76 | 0.720 | 771 |
| $C_4$ | 5 | 0.720 | 0.95 | 0.008 | 6842 |

[a]ND, not determined.

Example 10

Sequencing of Oncoimmunin-M

In order to determine the amino terminal amino acid sequence of the 36 kDa Oncoimmunin-M protein, two hundred picomoles of the protein was subjected to automated Edman degradation using an Applied Biosystem's model 430 and a Hewlett-Packard protein sequencer. No signal above background (less than 15 picomoles per degradation cycle) was detectable which strongly suggested that the N-terminus was blocked. Hence, the purity of the isolated protein was determined to be greater than 98% since the background PHT-amino acid peaks detected in the N-terminal amino acid sequence analysis were less than 10 pmoles derived from at least 10 distinct degredation cycles. The purified material was then treated with trypsin in order to obtain fragments for internal sequence determination.

Five hundred pmoles of the 36-kDa protein was dried down using a speed vac concentrator. Transferrin (500 pmoles) was used as a positive control, and a blank tube was used as a negative control. To each sample 25 μl of 8 M urea in 0.4 M NH$_4$HCO$_3$ was added. The pH for each sample and two controls was between 7.5 and 8.5. The samples were then reduced with 5 μl of 45 mM dithiothreitol and incubated at 50° C. for 15 minutes. After cooling to room temperature, the reduced samples were alkylated by the addition of 5 μl of 100 mM iodoacetamide. This was followed by a 15 minute incubation. After the addition of 60 μl water, trypsin was added to each tube at a molar ratio of 1:25 with 0.72 μg to the blank. The samples were then incubated at 37° C. for 24 hours after which the tryptic digest solutions were applied to a Vydac C$_{18}$ column (4.6×250 mm) for analysis and tryptic fragment isolation using a 0.1% trifluoroacetic acid (TFA) water/acetonitrile solvent system.

Two isolated tryptic peptide fragments from the 36 kDa protein were subjected to N terminal amino acid sequence determination. The sequences obtained were: sixteen residues for peptide 1 (Seq. Id. No. 1: Gly-Val-His-Pro-Leu-Ser-Cys-His-Gly-Xaa-Val-Leu-Gly-Glu-His-Gly) and ten residues for peptide 2 (Seq. Id. No. 2, Ser-Ala-Asp-Thr-Leu-Trp-Gly-Ile-Gln-Lys) where Xaa is an unidentified residue. Comparison of the amino acid sequences of these two tryptic fragments matched with two from the M chain of human lactate dehydrogenase (LDH)(179–194 and 319–328) with the exception of tryptophan at position 188 which was not determined.

Example 11

Comparison of Oncoimmunin-M with L-LDH-M$_4$

A) Electrophoresis

Figure 17:
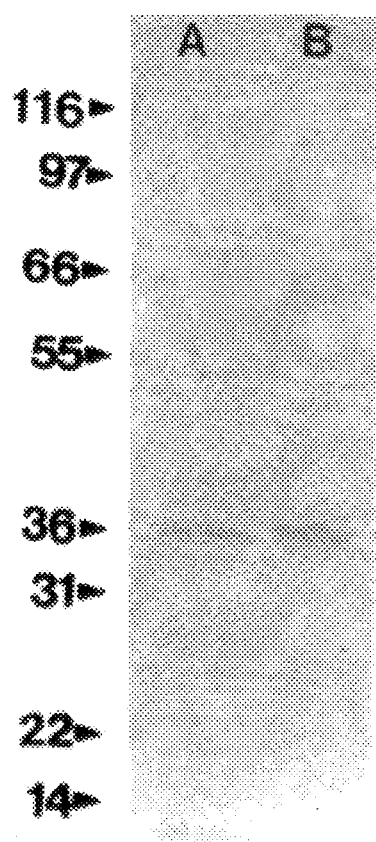
FIG. 17. Comparison of human L-LDH-$M_4$ (lane A) with the purified 36 kDa Oncoimmunin-M protein of this invention (lane B) by SDS-PAGE analysis (8%–16% gradient gel) under reducing conditions. The gel was developed by silver stain. The band in lane B shows a slight, but significant difference in its apparent molecular weight from the human L-LDH-$M_4$ standard protein (lane A) purchased from Sigma Chemical Co. (St. Louis, Mo., U.S.A.).

The 36 kDa Oncoimmunin-M and L-LDH-M$_4$ were compared by SDS-PAGE. The results are shown in FIG. 17 which shows a silver-stained SDS-PAGE 8%–16% gradient gel in which the 36 KDa protein (lane B) migrates with virtually the same R$_f$ value as human L-LDH-M$_4$ (lane A), however, the purified material has a slightly higher molecular weight as indicated by a slight, but significant and reproducible difference between the band in lane A and B.

B) Western Blot

After electrophoresis, the samples were electroblotted onto nitrocellulose. The factor was probed with a mouse monoclonal antibody raised against human L-LDH-M$_4$. A horse radish peroxidase labeled sheep anti-mouse antibody was used for detection. While the LDH band was quite intense when probed with antibody raised against human L-LDH-M$_4$, the 36 KDa band was found to be only slightly positive. This weak cross-reactivity suggested amino acid sequence similarity, but not identity with the amino acid sequence of L-LDH-M$_4$. This weak antibody cross-reactivity suggests that the antibody epitopes' conformation in native L-LDH-M$_4$ and Oncoimmunin-M differ significantly due to either the difference in the antibody epitopes' amino acid sequences or the conformational effects of the different amino acid sequences distal to the antibody epitopes in the Oncoimmunin-M molecule.

C) Bioassay of Human L-LDH-M$_4$

Figure 18:
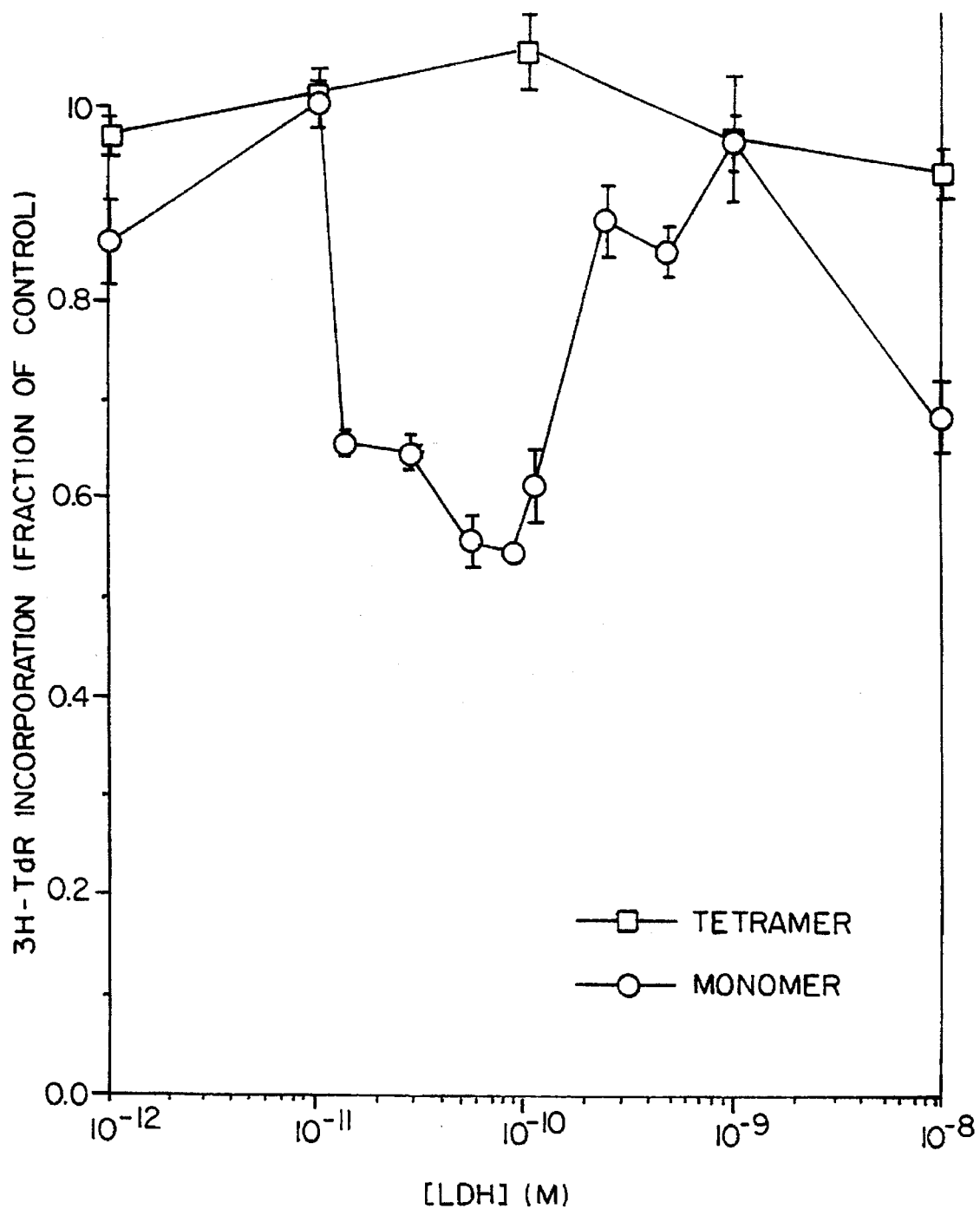
FIG. 18. $[^3H]$-thymidine incorporation into HL-60 cells induced by L-lactic dehydrogenase $M_4$ (L-LDH-$M_4$), a tetrameric form, and mild acid treated L-LDH-$M_4$, a monomeric form. Native tetrameric L-LDH-$M_4$ (open squares) is shown to be totally inactive in inducing Oncoimmunin-M activity over a wide range of concentrations. In contrast, the acid treated L-LDH-$M_4$ (open circles) exhibited Oncoimmunin-M like bioactivity at a lower concentration.

In order to confirm the identify of the purified 36 KDa Oncoimmunin-M factor as a protein related to L-LDH-M$_4$, biological activity of L-LDH-M$_4$ toward HL-60 target cells was determined. Brief exposure of L-LDH-M$_4$ to acid (pH 5) is known to destabilize the tetrameric oligomer of L-LDH-M$_4$ and to yield monomeric and dimeric forms of LDH-M. [$^3$H]-Thymidine incorporation into the DNA of HL-60 cells as a function of L-LDH in both the tetrameric and monomeric forms over a wide LDH concentration range was measured and the results are plotted in FIG. 18.

The tetramer did not exhibit any effects on the [$^3$H]-thymidine incorporation into the DNA of the target cells. However, after the tetramer was dissociated into a predominantly monomoeric form in a pH 5 buffer, [$^3$H]-thymidine incorporation in the DNA of HL-60 cells was inhibited at concentrations ranging from $10^{-11}$ to $10^{-10}$ M. Thus only the monomer and not the tetramer showed bioactivity in this assay, and the bioactivity of even the monomer vanished at high LDH concentrations. Normal monomeric LDH tends to polymerize into a tetrameric form at high, but not physiological concentrations, explaining the observed loss of activity. In contrast, Oncoimmunin-M does not appear to polymerize and there is no loss of Oncoimmunin-M activity at high concentrations.

D) Differences from L-LDH-M

These experiments indicate relatedness rather than identity of the 36 kDa protein with L-LDH-M for several reasons: First, complete biological activity cannot be induced. As the concentration of the acid treated L-LDH-M$_4$ increases, the observed bioactivity decreases (see FIG. 18), due to its natural tendency to form a tetrameric oligomer which shows no Oncoimmunin-M activity. Second, using native PAGE analysis, unlike the human L-LDH-M$_4$ which retains the potential to re-aggregate to the tetrameric state following dissociation into monomeric units, the purified 36 KDa protein does not show any tendency to tetramerize, however, the formation of a dimer or trimer is possible. Third, by Western blot analysis only weak cross-reactivity was found with the purified protein. Thus the amino acid sequence of the purified protein may differ from LDH significantly in parts of the molecule not sequenced.

Example 12

Oncoimmunin-M Induced Differentiation of Leukemic Cell Lines

A) Inhibition of Thymidine Incorporation

HL-60, K562, and HEL cells were removed from RPMI medium containing 10% fetal calf serum and washed twice in the serum-free medium. They were incubated for two days in this medium. The bioassay was run under the following conditions: 0.6–2.4×10$^5$ cells/200λ/well of a 96-well flat-bottomed cell culture plate were incubated with active fractions in the serum-free medium for 48 hours. (with fractions from Q-Sepharose columns, 10–15% of volume/well is from the column fraction.) During the last 4 hours of this incubation, 0.5 μCi of tritiated thymidine was added per well. Cells were harvested and the number of counts in cultures containing active material were decreased by 30–90%.

Figure 6:
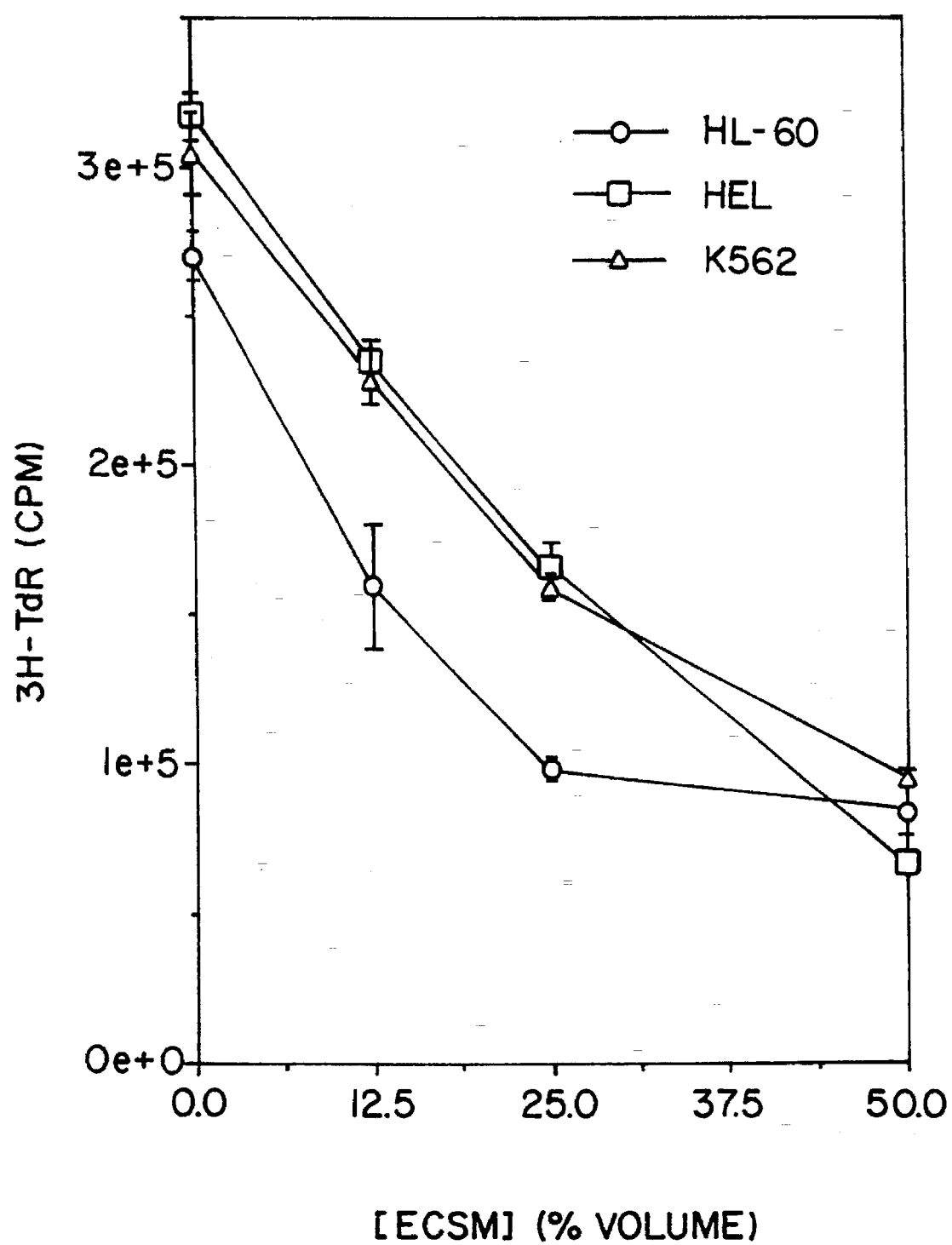
FIG. 6. [$^3$H]-thymidine incorporation by myeloid cell lines HL-60, HEL, and K562 as a function of percent of extracapillary space medium (ECSM). The ECSM used in this assay was taken from the bioreactor at day #300 when the protein concentration was 1.5 mg/ml. The inhibition of [$^3$H]-thymidine incorporation with increasing ECSM concentration reveals characteristic Oncoimmunin-M biological activity.

A reduction of [$^3$H]-thymidine incorporation into the DNA of HL-60, HEL, and K562 cells as a function of increasing percent concentration (v/v) of the serum-free condition medium (ECSM) in which A431 cells were grown, is shown in FIG. 6. The decrease in [$^3$H]-thymidine incorporation apparently did not represent a cytotoxic response of the target cells to the factors in ESCM, as their viability, as monitored by trypan blue exclusion, was found to be greater than 95%.

In order to determine whether the observed antiproliferative activity was due to one of the known cytokines, proliferation assays were performed in the presence of ECSM (50% v/v) and the following cytokines at the indicated concentrations: M-CSF (1 ng/ml), GM-CSF (1 ng/ml), IL-2

Figure 7:
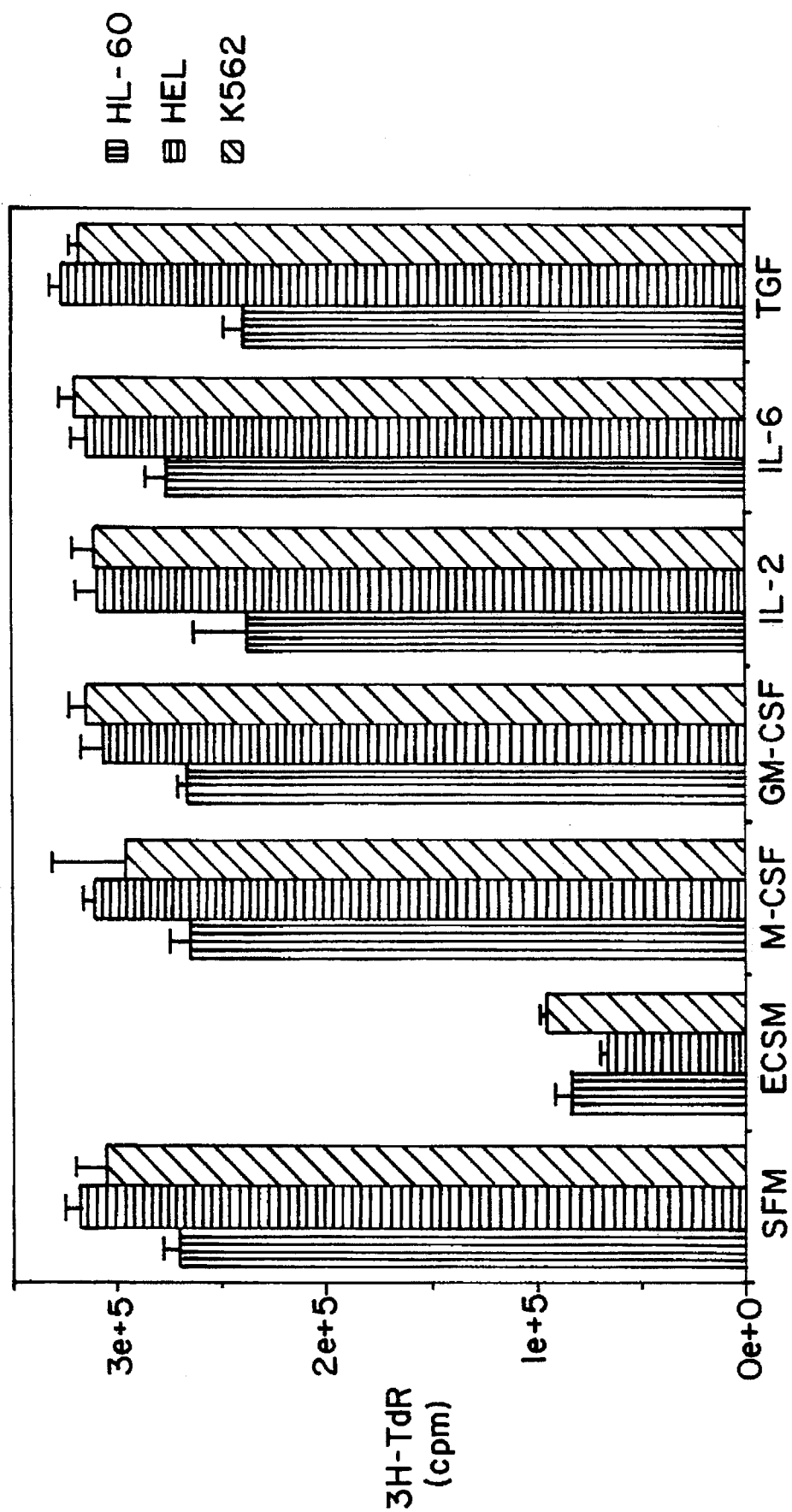
FIG. 7. [$^3$H]-thymidine incorporation into myeloid cell lines (⫶) HL-60, (--) HEL, and (//) K562 in serum-free medium (SFM) and in the presence of ECSM (50% v/v), M-CSF (1 ng/ml), GM-CSF (1 ng/ml), IL-2 (100 U/ml), IL-6 (10 U/ml) and TGF$_\beta$ (100 pM). The data indicate that the Oncoimmunin-M activity present in ECSM is not due to the screened cytokines including those known to be secreted by A431 cells (e.g. IL-6 and TGF$_\beta$).

(100 U/ml), IL-6 (10 U/ml) and TGF$_{\beta 1}$ ((100 pM). The results are shown in FIG. 7. None of the cytokines significantly reduced [$^3$H]-thymidine incorporation as the 50% (v/v) of ESCM did.

Additionally, no effects on the incorporation of [$^3$H]-thymidine into the DNA of the three cell lines were observed at the following concentrations: M-CSF (10.0, 1.0, and 0.1 ng/ml); GM-CSF (10, 1.0, and 0.1 ng/ml; IL-2 (1000, 100, 10.0, 0.1, and 0.01 U/ml); IL-6 (1000, 100, and 10 U/ml); TGF$_{\beta 1}$ (1000, 100, 10, 1, 0.1, 0.01 and 0.001 pM). Similarly, LIF did not affect the rate of [$^3$H]-thymidine uptake into HL-60 cells at 100, 10.0 or 1.0 ng/ml. The absence of IL-4 and TNF$_\alpha$ activity in this supernatant has been previously reported (Packard, B. S. pp. 293–303 In: *Progress in Regional Cancer Therapy*. Jakcez, et al., eds., Springer, Heidelberg, (1990)).

In contrast to lymphoid cells which proliferate upon recognition of foreign targets, when myeloid cells are activated or are induced to differentiate their rates of proliferation decrease. In the myelopoietic hierarchy as a cell differentiates, its mitotic potential decreases with endstage myeloid cells completely lacking mitotic capability (Packard, *Trends Biochem. Sci.*, 10:378–379 (1985)). Accordingly, as a myeloid leukemic cell which exists in a preterminally differentiated state is induced to differentiate, its rate of cell division is programmatically reduced. Thus, the decreased rates of [$^3$H]-thymidine incorporation into the DNA of three myeloid leukemic cell lines, HL-60, HEL, and K562 (FIGS. 6 and 7), can be considered as a marker of myeloid differentiation or activation.

B) Induced Expression of Cell Surface Markers

Myeloid cell differentiation induced by treatment with Oncoimmunin-M was determined by (a) staining of cells on microscope slide with Wright's stain and nonspecific and chloroesterase stains and (b) antibody binding detected by flow cytometry as described above under phenotyping.

Figure 19:
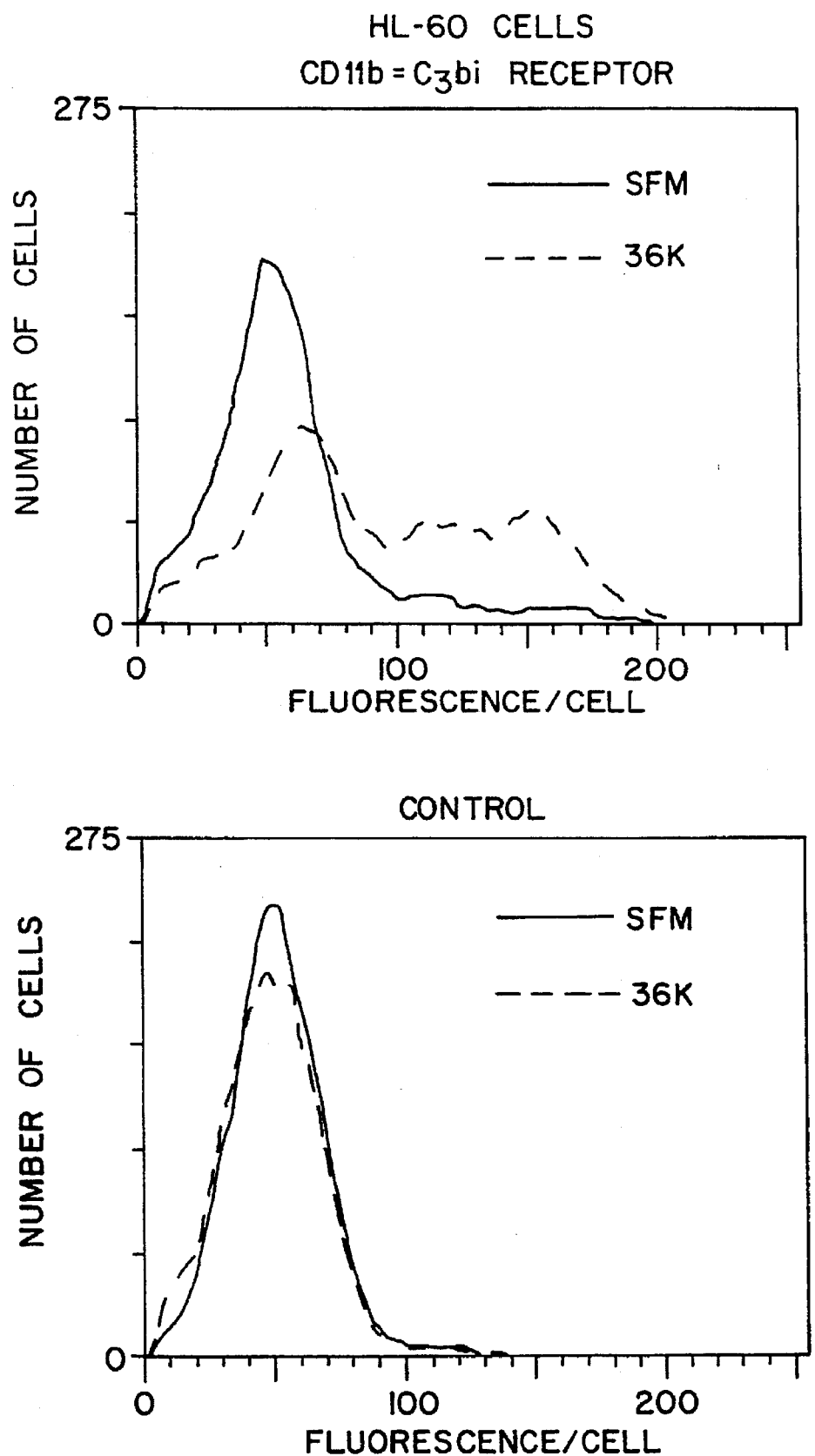
FIG. 19. Flow cytometric analysis of induced expression of the CD11b surface marker on HL-60 cells by Oncoimmunin-M. Cells were incubated with the 36 kDa Oncoimmunin-M for two days. Prior to staining the cells, 10 μg of human IgG was added to the culture and then the cells were labeled with CD11b-phycoerythrin. Data from cells incubated in serum free medium without Oncoimmunin-M are indicated by the dotted lines and data from cells that had been incubated in serum free medium with Oncoimmunin-M (2 nM) for 2 days are indicated by the dashed lines. Cells were removed from serum containing media and placed in serum free medium for two days prior to the assay. (A) HL-60 cells stained with CD11b-phycoerythrin (mean and peak channel numbers are 79 and 28 respectively); (B) HL-60 cells which are unstained, but tagged with unlabeled IgG to provide a control for autofluorescence.

For HL-60 the following antigens were found to be elevated: major histocompatibility-class II and CD11b (see FIG. 19).

Figure 20A:
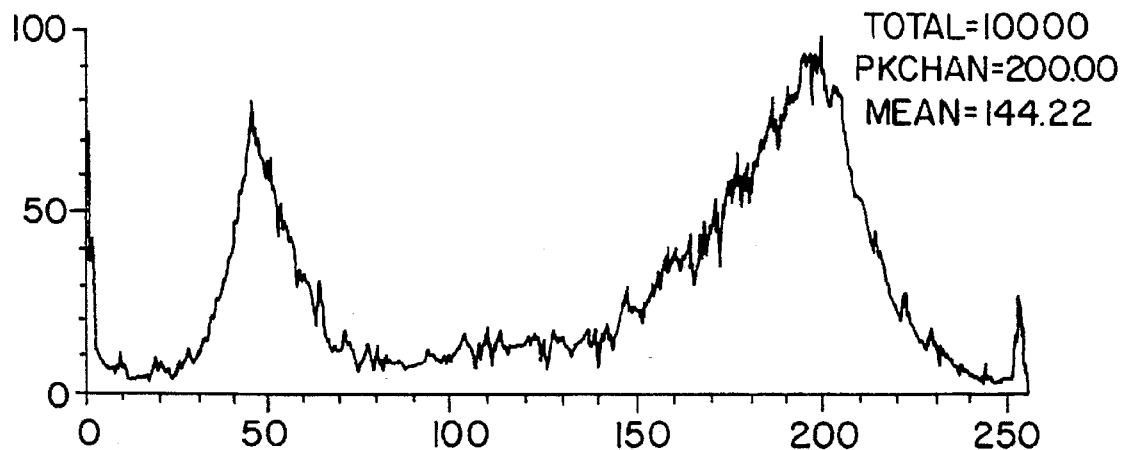
FIG. 20. Flow cytometry FACScan histogram of HL-60 cells treated with Oncoimmunin-M (2 nM) using anti CD41
Figure 20B:
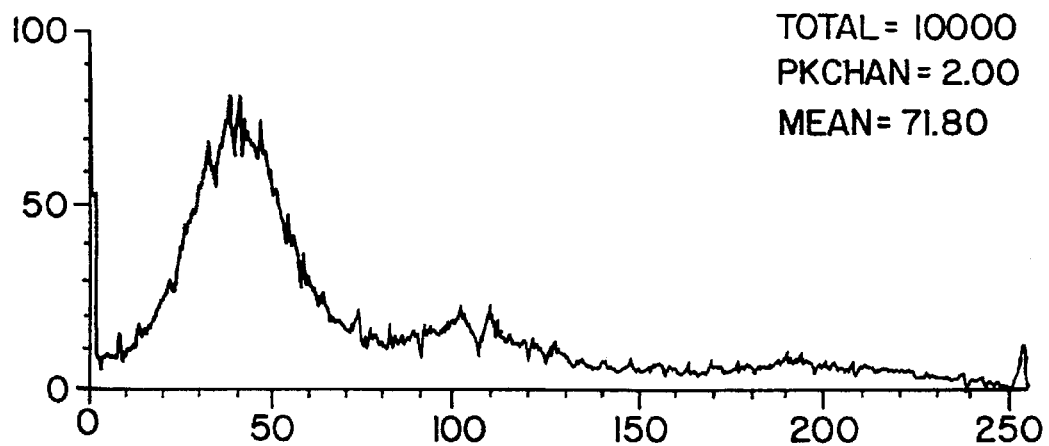

After two days treatment with Oncoimmunin-M, HL-60 cells showed an increase in CD-41 expression, as evidenced by increased CD-41-FITC binding to these cells (FIG. 20(a)) over the control (FIG. 20(b)).

Figure 21A:
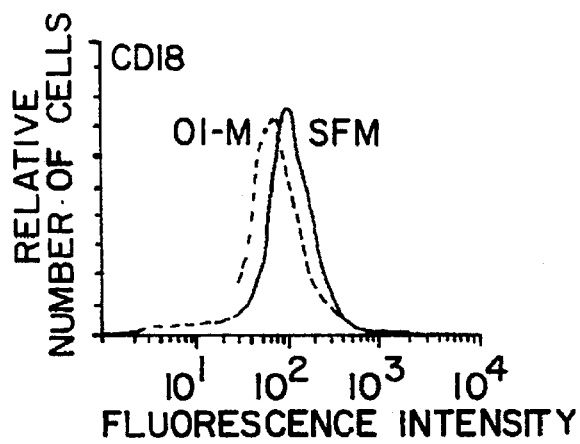
Figure 21B:
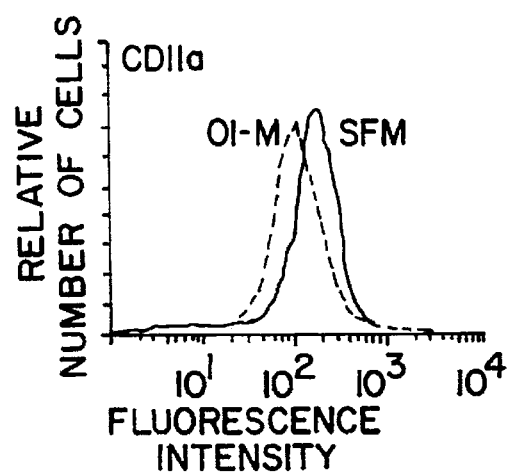
Figure 21C:
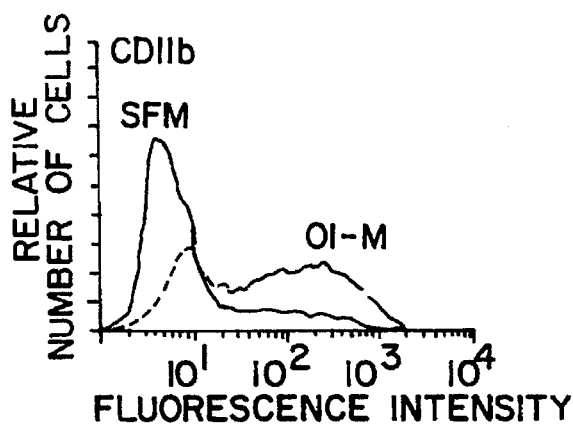
Figure 21D:
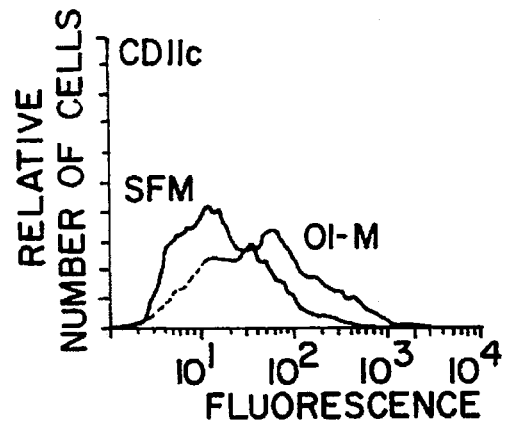
Figure 21E:
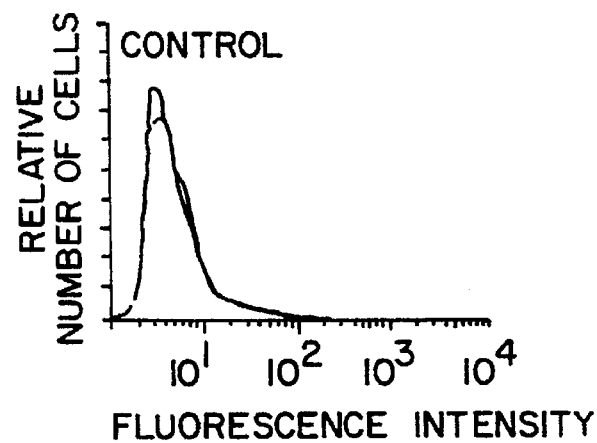

HL-60 cells were similarly cultured in the presence of the Oncoimmunin-M, 36 kDa protein for 2 days and then stained with CD18-FITC, CD11a-FITC, CD11b-PE, and CD11c, and fluorescein-conjugated monoclonals to CD18 and CD11b. The level of cell surface expression of CD18, the molecule thought to be the β chain for all three myeloid integrins, decreased slightly (<10%) on the Oncoimmunin-M treated cells compared with the control (FIGS. 21A and 21E, respectively). Similarly, the level of CD11a, the α chain of the integrin LFA-1, decreased by about the same amount (FIG. 21B). In contrast the distribution of CD11b became bimodal (FIG. 21C) and the mean level of CD11c, the α chain of integrin p150,95 was increased (FIG. 21D).

Example 13

Chemotaxis Induced By Oncoimmunin-M

To assess whether the Oncoimmunin-M induced alterations in integrin expression are associated with the induction of a biologic activity which could serve a role in antitumor or antimicrobial function, HL-60 cells that had been exposed to Oncoimmunin-M (2 nM) for two days were assayed for chemotactic ability. Specifically, the treated cells were placed in a multiwell microchemotaxis chamber and assayed for their ability to migrate in response to a gradient of the chemoattractant recombinant human C5a (rHuC5a), recombinant interleukin-8, and the peptide f-Met-Leu-Phe.

Cells were suspended in the serum-free medium (SFM) at a concentration of $5 \times 10^5$ cells/ml. Assays in which the total number of cells migrating through the polyvinylpyrrolidone-free polycarbonate membranes (5 µm pores; Nucleopore Corp., Pleasanton, Calif.) were performed for 3 hr in a 37° C. incubator containing 5% $CO_2$. After incubation, nonmigrated cells were wiped off the filters which were then fixed in methanol and stained with Diff-Quik (Dade Diagnostics, Inc., Aguada, Puerto Rico). Migrated cells were counted with an Optomax System 40-10 Image Analyzer (Optomax, Inc., Hollis, N.H., U.S.A.). Random migration was determined by quantifying cell migration to serum-free medium alone.

Figure 22A:
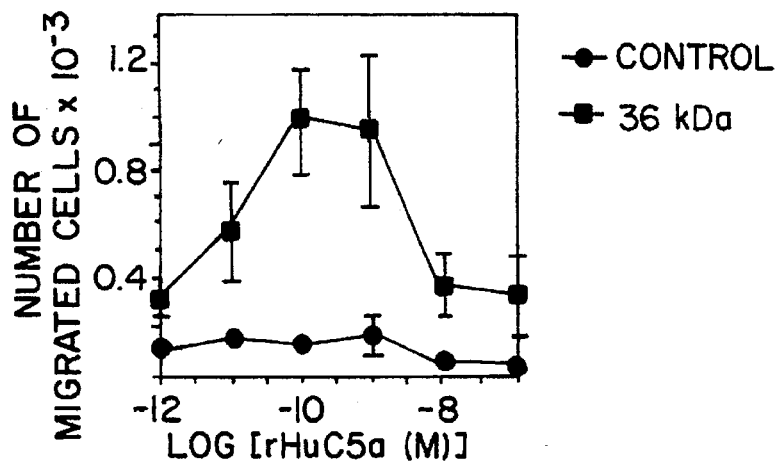
Figure 22B:
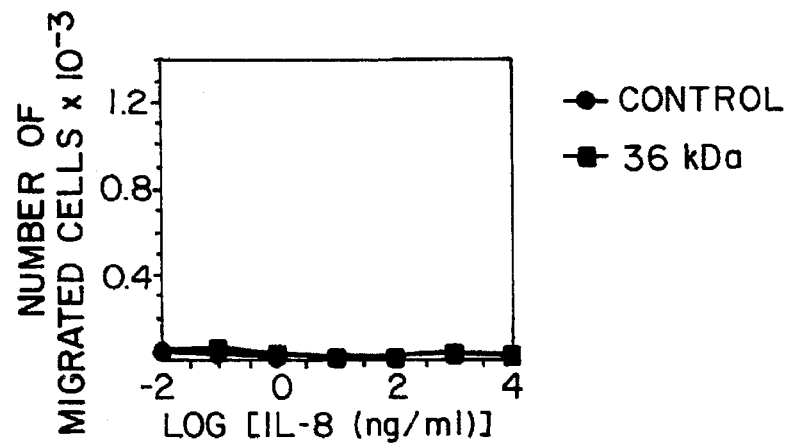
Figure 22C:
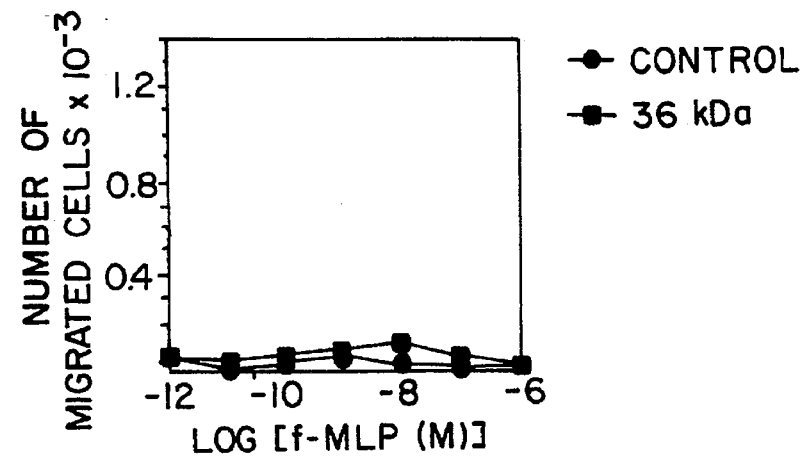
Figure 23A:
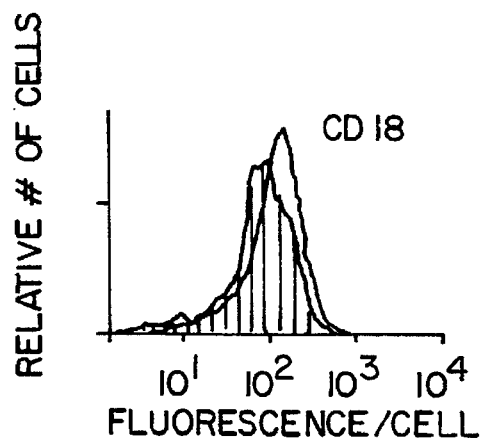
Figure 23B:
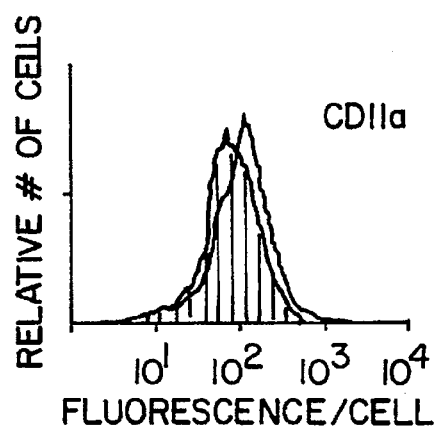
Figure 23C:
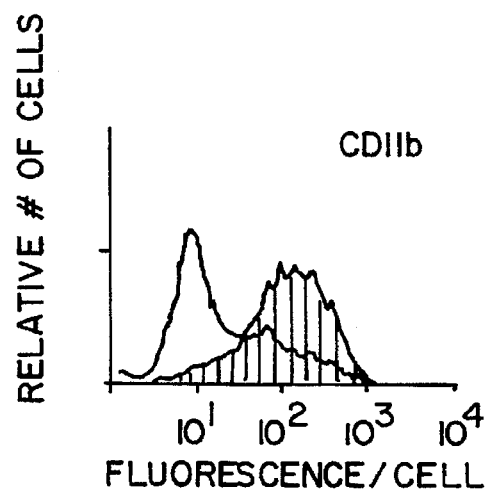
Figure 23D:
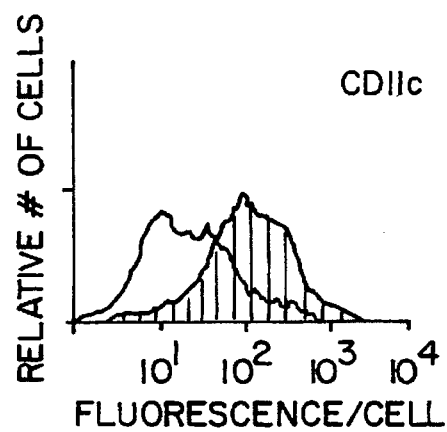
Figure 23E:
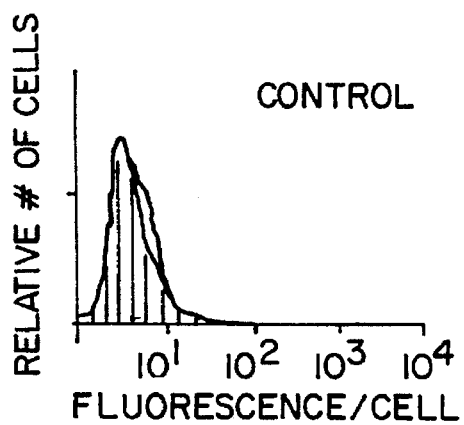

Oncoimmunin-M treated HL-60 cells showed a chemotactic ability in response to a rHuC5a gradient, as shown in FIG. 22A, with a maximum response observed in the concentration range of $10^{-10}$ to $10^{-9}$ M. Oncoimmunin-M treated HL-60 cells showed no significant response to either IL-8 (FIG. 22B) or to f-Met-Leu-Phe (FIG. 22C). The control cells (closed circles) were unresponsive to all three chemoattractants (FIG. 22A, B, and C).

Chemokinetic migration (chemokinesis) was assayed by placing equal concentrations of the chemoattractants in the upper and lower wells of the chamber. Oncoimmunin-M-treated HL-60 motile responses to rHuC5a were primarily chemotactic, not chemokinetic (data not shown).

Since the bulk population of Oncoimmunin-M treated HL-60 cells showed heterogeneity with respect to both chemotaxis and integrin expression, a correlation between motile responsiveness to rHuC5a and altered surface expression of these receptors was sought. Thus the motile and nonmotile subpopulations were physically isolated after exposure to rHuC5a in a chemotaxis separation chamber and flow cytometric evaluation of CD18, CD11a, CD11b, and CD11c was performed (see FIG. 23). The nonmotile population exhibited heterogeneous expression of CD11b and CD11c and homogeneous distributions of CD11a and CD18 (FIG. 23).

In contrast, the motile subpopulation (shaded profiles in FIG. 23) exhibited homogeneous, high expression of CD11b and CD11c and slightly decreased (<10%) homogeneous CD11a and CD18 levels. These findings suggest that expression levels of the two myeloid integrin subunits or the conformational determinants of epitopes for the antibodies used in this study are differentially modulated on motile and nonmotile cells as a function of Oncoimmunin-M treatment.

The significance of Oncoimmunin-M induced HL-60 migration toward a chemoattractant gradient and the associated alterations in myeloid integrin surface expression may lie in the latter's function as an element of the immunosurveillance network. Correlation between the cytokine-induced upregulation of two myeloid integrin proteins on the surface of nonterminally differentiated cells and cellular responsiveness to a chemoattractant points toward the bone marrow as a reservoir for potential antitumor cellular agents. These results support the idea that unleashing the immunotherapeutic potential of the bone marrow may be possible by using the contents of the tumor itself, e.g. Oncoimmunin-M, for recruitment of uncommitted myeloid elements via ex vivo activation.

Example 14

Amino Acid Composition of Oncoimmunin-L

The amino acid composition of the purified Oncoimmunin-L was determined by placing 10 µl aliquots of the Oncoimmunin-L containing fractions in KIMAX glass tubes. The contents of the tubes were dried, the tubes evacuated, and the samples were hydrolyzed in 6 N HCL with a trace of phenol for 20 hours. In order to determine the cysteine content, some samples were oxidized with performic acid at 4° C. for 3 hours before hydrolysis. AccQ Tag amino acid analyses were then performed on the samples (Cohen et al., *Anal. Biochem.*, 211: 279–287 (1993)) using AccQ Tag reagent kits Water's Associates (Milford, Conn., U.S.A.).

The results of the amino acid analysis are shown in Table 5. About 25% of the Oncoimmunin-L is composed of the acidic residues aspartic and glutamic acid and thamide residues whereas the basic residues contribute only 13%. Other notable compositional features include about 30% aliphatic hydrophobic amino acids and a relative low cysteine contend (determined from the performic oxidized samples) for a protein of this size.

TABLE 5

Amino Acid Composition of Oncoimmunin-L.

| Amino Acid | mole % ± s.d. | mole % ± s.d. |
|---|---|---|
| ASX | 11.6 ± 0.1 | 43.5 ± 0.4 |
| SER | 5.9 ± 0.1 | 22.1 ± 0.4 |
| GLX | 13.9 ± 0.4 | 52.1 ± 1.5 |
| GLY | 5.9 ± 0.2 | 22.1 ± 0.8 |
| HIS | 1.5 ± 0.1 | 5.6 ± 0.4 |
| ARG | 3.2 ± 0.2 | 12.0 ± 0.8 |
| THR | 5.0 ± 0.1 | 18.8 ± 0.4 |
| ALA | 9.3 ± 0.1 | 34.9 ± 0.4 |
| PRO | 3.1 ± 0.1 | 11.6 ± 0.4 |
| CYS | 1.1 ± 0.1 | 4.1 ± 0.4 |
| TYR | 2.4 ± 0.2 | 9.0 ± 0.8 |
| VAL | 5.4 ± 0.1 | 10.3 ± 0.4 |
| MET | 2.8 ± 0.2 | 10.5 ± 0.8 |
| LYS | 9.7 ± 0.3 | 36.4 ± 1.2 |
| ILE | 5.0 ± 0.1 | 18.8 ± 0.1 |
| LEU | 11.1 ± 0.5 | 41.6 ± 1.9 |
| PHE | 5.2 ± 0.4 | 19.5 ± 1.5 |
| TRP | ND | ND |

Example 15

Sequencing of Oncoimmunin-L

To determine the amino-terminal amino acid sequence, 200 picomoles of the purified 45 kDa Oncoimmunin-L protein was subjected to automated Edman degradation using an Applied Biosystems model 430 protein sequence (Applied Biosystems, Foster City, Calif., U.S.A.). No signal above background (more than 15 pmol/cycle) was detectable, which strongly suggested that the amino terminus was blocked. In addition this provided further evidence that the protein was purified to homogeneity since any contaminants would be expected to contribute a signal in the degradation.

The purified protein was then subjected to a trypsin digest (227 pmoles) to obtain fragments for internal sequence determination as described by Packard and Komoriya (Packard and Komoriya, *J. Biol. Chem.*, 268:6356–6363 (1993)). Five hundred pmol of the 45 kDa protein was dried down using a Speed Vac concentrator (Savant Instruments Inc., Farmingdale, N.Y., U.S.A.). A blank tube and 500 pmol of transferrin were used as controls. To each sample 25 μl of 8 M urea in 0.4 M $NH_4HCO_3$ was added. The pH for each of the three was between 7.5 and 8.5. The samples were then reduced with 5 μl of 45 mM dithiothreitol and incubated at 50° C. for 15 minutes. After cooling to room temperature, the reduced samples were alkylated by the addition of 5 μl of 100 mM iodoacetamide. This was followed by a 15 minute incubation. After the addition of 60 μl of water, trypsin was added to each tube at a molar ration of 1:25 with 0.72 μg to the blank. The samples were then incubated at 37° C. for 24 hours after which the tryptic digest solutions were applied to a Vydac $C_{18}$ column (4.6×250 mm, Vydac, Hesperia, Calif., U.S.A.) for analysis and tryptic fragment isolation using a 0.1% trifluoroacetic acid (TFA)/water/acetonitrile solvent system.

Seven well-resolved tryptic peptide fragments were collected from the $C_{18}$ reverse phase HPLC and then subjected to amino-terminal amino acid sequence determination (W. M. Keck Foundation Biotechnology Resource Laboratory at Yale University, New Haven, Conn., U.S.A.). The identified sequences are shown in Table 6. Comparison of six tryptic fragments with proteins in the GenBank at the National Institutes of Health indicated identity with sequences 57–69, 97–110, 111–129, 204–213, and 291–301 of human leukocyte elastase inhibitor (hLEI), a serine protease inhibitor found in monocytes, macrophages, and neutrophils (Remold-O'Donnell et al., *J. Exp. Med.*, 162:2142–2155 (1985)). These six tryptic fragments correspond to 65 amino acid residues out of about 375 residues predicted from a protein with a molecular weight of 45 kda (i.e., ca. 17% of the total residues).

TABLE 6

Sequences of 7 tryptic fragments of Oncoimmunin-L.

| Sequence ID Number | Amino Acid Sequence |
|---|---|
| 3 | Thr—Phe—His—Phe—Asn—Thr—Val—Glu—Glu—Val—His—Ser—Arg |
| 4 | Thr—Tyr—Asn—Phe—Leu—Pro—Glu—Phe—Leu—Val—Ser—Thr—Gln—Lys |
| 5 | Thr—Tyr—Gly—Ala—Asp—Leu—Ala—Ser—Val—Asp—Phe—Gln—His—Ala—Glu—Asp—Ala—Arg |
| 6 | Phe—Ala—Tyr—Gly—Tyr—Ile—Glu—Asp—Leu—Lys |
| 7 | Val—Leu—Glu—Leu—Pro—Tyr—Gln—Gly—Glu—Glu—Leu—Ser—Met—Val—Ile—Leu—Leu—Pro—Asp—Asp—Ile—Glu—Asp—Glu—Ser—Thr—Gly—Leu—Lys |
| 8* | Leu—His—Glu—Trp—Thr—Lys—Pro—Glu—Asn—Leu—Asp—Phe—Ile—Glu—Val—Asn—Val—Xaa—Leu—Pro |
| 9 | Leu—Gly—Val—Gln—Asp—Leu—Phe—Asn—Ser—Ser—Lys |

*Xaa designates an unidentified amino acid residue.

In a seventh fragment, a total of nineteen cycles were analyzed. The amino acids determined for eighteen cycles matched eighteen of the amino acids in sequence 256–274 of hLEI. The amino acid present in hLEI at position number 18 of this tryptic fragment is serine. However, the signal levels for serine and dehydroserine were similar to the background signal in this cycle. Since no amino acid was unequivocally recognizable, an assignment could not be made. The amino acid residue for this cycle may be a cysteine. This possibility may be consistent with the amino acid composition data which show a higher cysteine content than that found in hLEI.

It is expected that further internal amino acid sequence analysis will provide additional sequence mismatching between the 45 kDa Oncoimmunin-L protein and hLEI. For example, when sequences from regions common to other serpin family members are aligned and compared, percent sequence identity ranges from 29.7% to 57.9%. Therefore, the sequencing results strongly suggest that the purified Oncoimmunin-L is a member of the serpin superfamily of proteins and bears a similarity to human leukocyte elastase inhibitor.

All publications, patents and patent applications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An antibody or binding fragment thereof, that specifically binds a substantially pure oncoimmunin-myeloid (OI-M) factor, said factor comprising the polypeptide sequences of SEQ ID No. 1 and SEQ ID No. 2, wherein said factor is derived from a tumor cell line, and said factor has a molecular weight of about 36 kDa by SDS-PAGE analysis and said factor has the ability to inhibit growth in a myeloid cell line or induce differentiation of a myeloid cell line in an interleukin-2 and interleukin-4 free, serum-free medium, and wherein said antibody or binding fragment thereof is derived from a mammal immunized with said oncoimmunin-myeloid factor.

2. The antibody according to claim 1, wherein said antibody is monoclonal.

3. A method of detecting Oncoimmunin-myeloid factor in a target sample, said method comprising contacting the target sample with the antibody or binding fragment thereof according to claim 1, and detecting the specific binding between the antibody and the target sample.

* * * * *